(12) United States Patent
Kosaka et al.

(10) Patent No.: US 8,194,235 B2
(45) Date of Patent: Jun. 5, 2012

(54) SAMPLE ANALYZER

(75) Inventors: Tokihiro Kosaka, Kakogawa (JP);
Koichi Okubo, Kobe (JP)

(73) Assignee: Sysmex Corporation, Kobe (JP)

( * ) Notice: Subject to any disclaimer, the term of this patent is extended or adjusted under 35 U.S.C. 154(b) by 317 days.

(21) Appl. No.: 12/462,118

(22) Filed: Jul. 28, 2009

(65) Prior Publication Data

US 2010/0066996 A1  Mar. 18, 2010

(30) Foreign Application Priority Data

Aug. 1, 2008 (JP) ................................. 2008-200179

(51) Int. Cl.
*G01N 33/48* (2006.01)
*G01N 21/01* (2006.01)

(52) U.S. Cl. ......................................... 356/39; 356/244

(58) Field of Classification Search ............... 356/39–42
See application file for complete search history.

(56) References Cited

U.S. PATENT DOCUMENTS 7,760,340 B2 * 7/2010 Hoshiko et al. .................. 356/39
2007/0229830 A1 * 10/2007 Yamamoto et al. ........... 356/414

FOREIGN PATENT DOCUMENTS

| JP | 10-115620 | 5/1998 |
| JP | 2004-226065 | 8/2004 |
| JP | 2005-017245 A | 1/2005 |

* cited by examiner

*Primary Examiner* — Michael P Stafira
(74) *Attorney, Agent, or Firm* — Brinks Hofer Gilson & Lione

(57) ABSTRACT

The present invention is to present a sample analyzer, comprising: an imaging device for imaging a sample container which has translucency and contains a sample; a measuring device for aspirating the sample contained in the sample container and measuring the aspirated sample; a transporting device for transporting the sample container to a supply position for supplying the sample contained in the sample container to the measuring device; a sample volume obtainer for obtaining sample volume information relating to volume of the sample in the sample container, based on an image obtained by imaging the sample container by the imaging device; and a transport controller for controlling the transporting device to perform a transport operation in accordance with the sample volume information obtained by the sample volume obtainer.

21 Claims, 38 Drawing Sheets

7 SYSTEM CONTROL APPARATUS

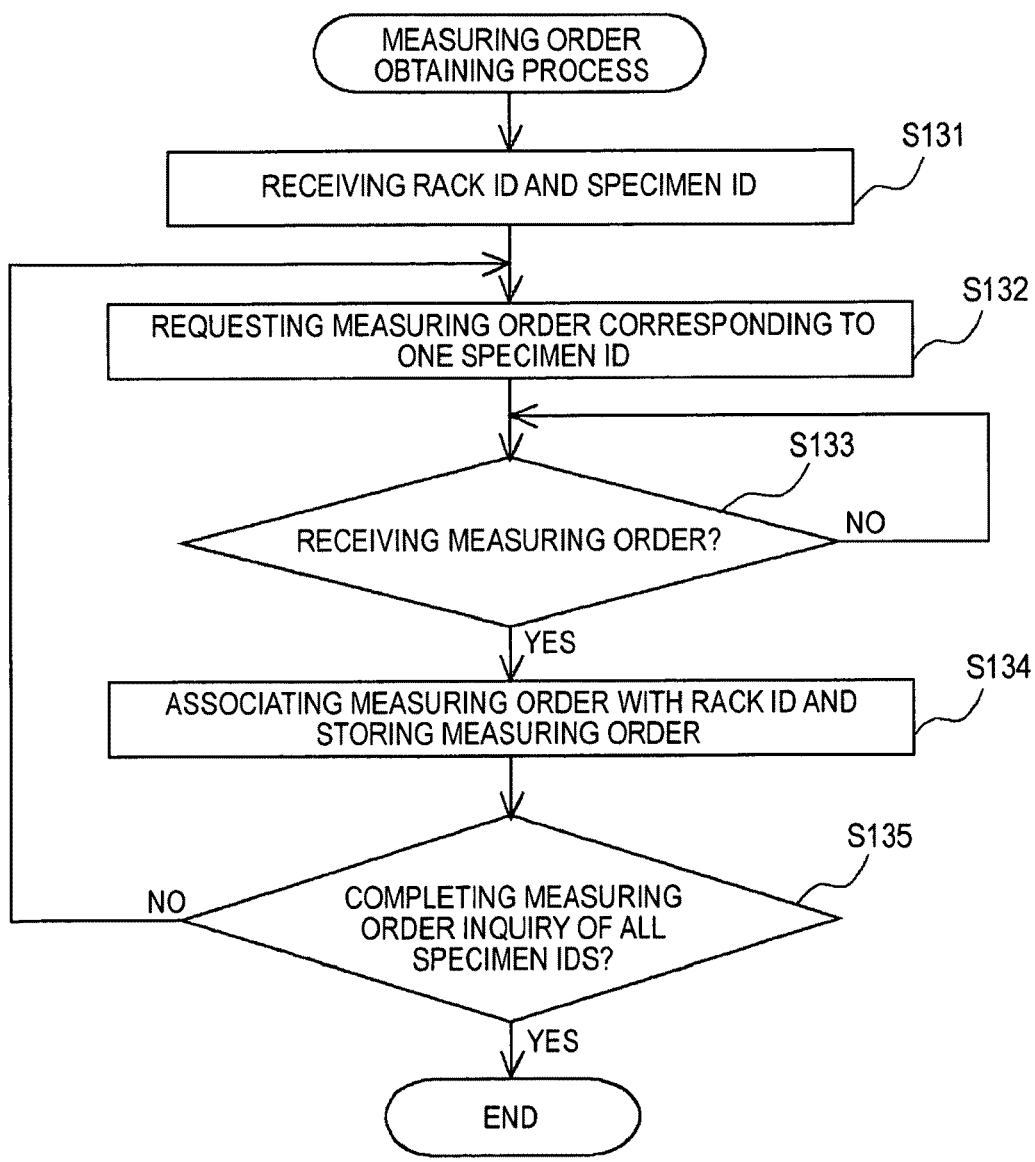

FIG.27

| RACK ID | SR0001 | | |
|---|---|---|---|
| 1 | ×××1 | CBC,DIFF | |
| 2 | ×××2 | CBC,DIFF | |
| 3 | | | |
| 4 | ×××4 | CBC,DIFF,NRBC | |
| 5 | ×××5 | CBC,DIFF | |
| 6 | ×××6 | CBC,DIFF | MICRO-MEASUREMENT MODE |
| 7 | ×××7 | CBC,DIFF,RET | |
| 8 | ×××8 | CBC | |
| 9 | | | |
| 10 | ××10 | CBC,DIFF | |

HOLDING POSITION INFORMATION | SPECIMEN ID | ANALYSIS ITEM DATA | MICRO-MEASUREMENT MODE INSTRUCTION DATA

MEASURING ORDER

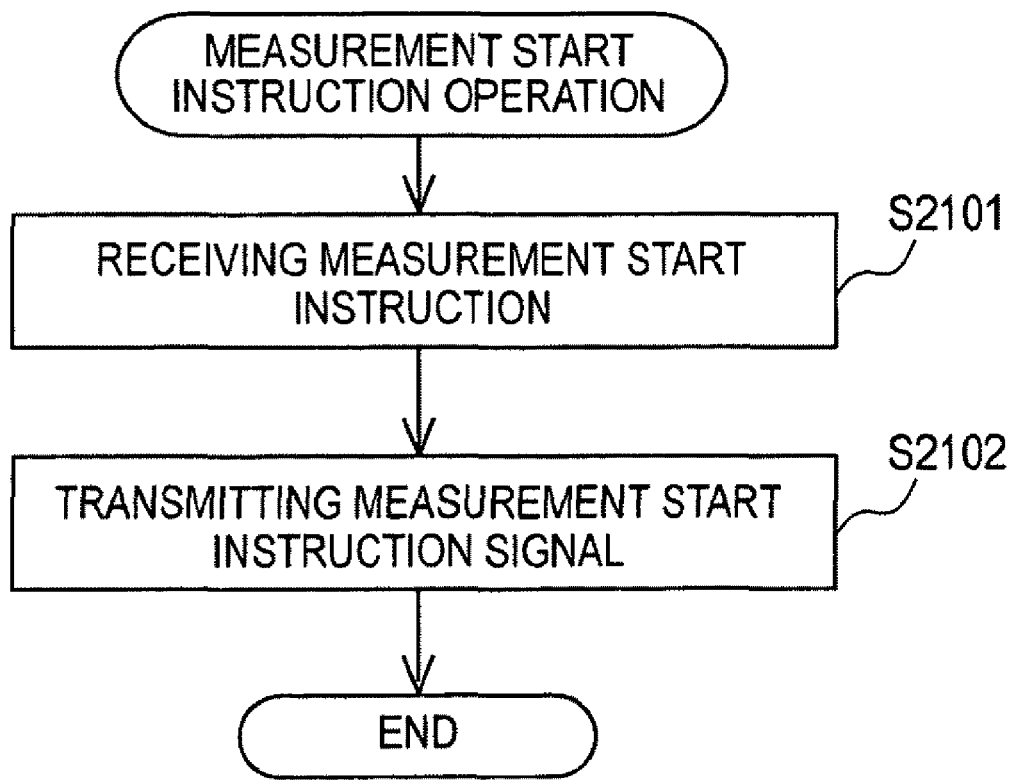

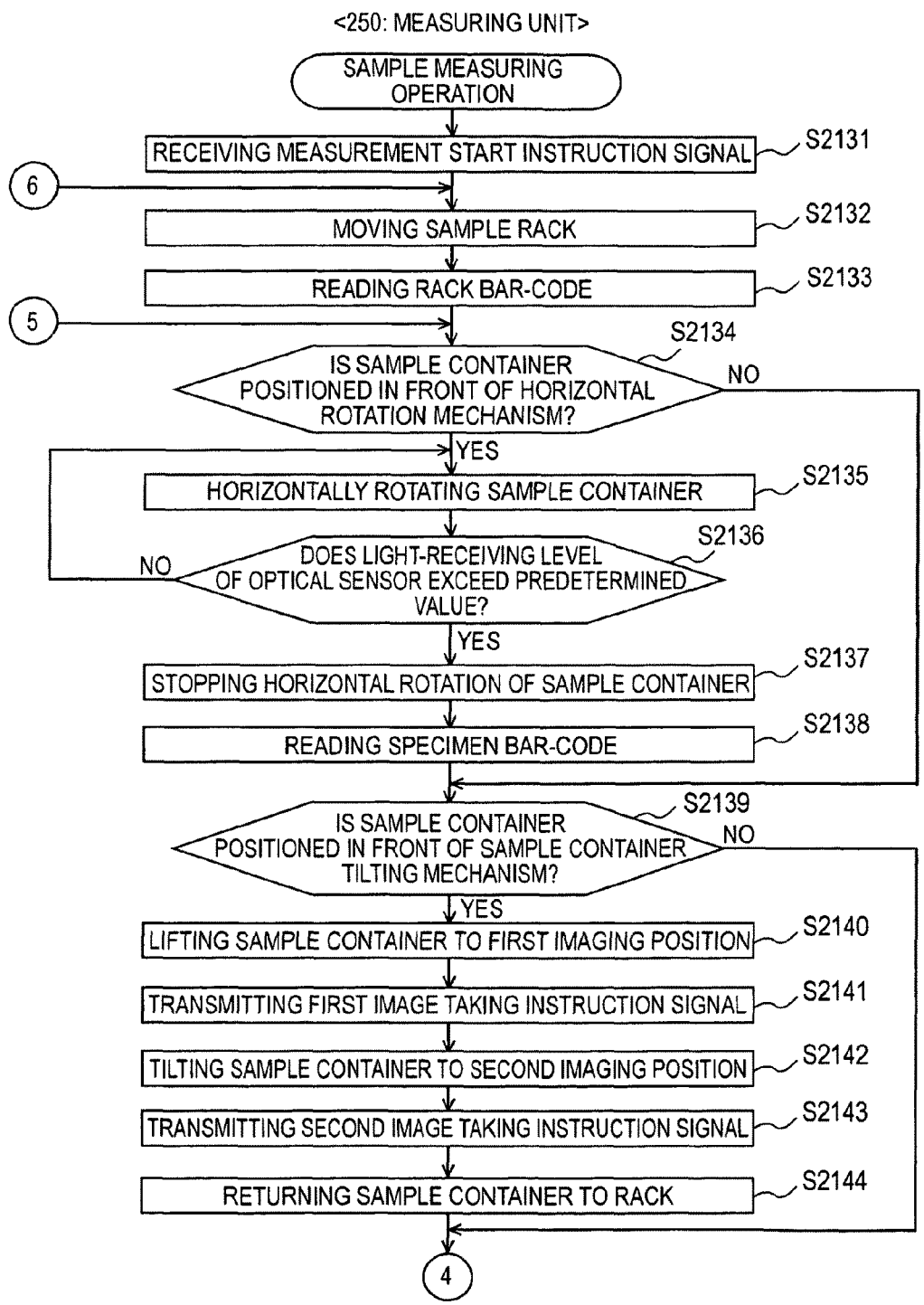

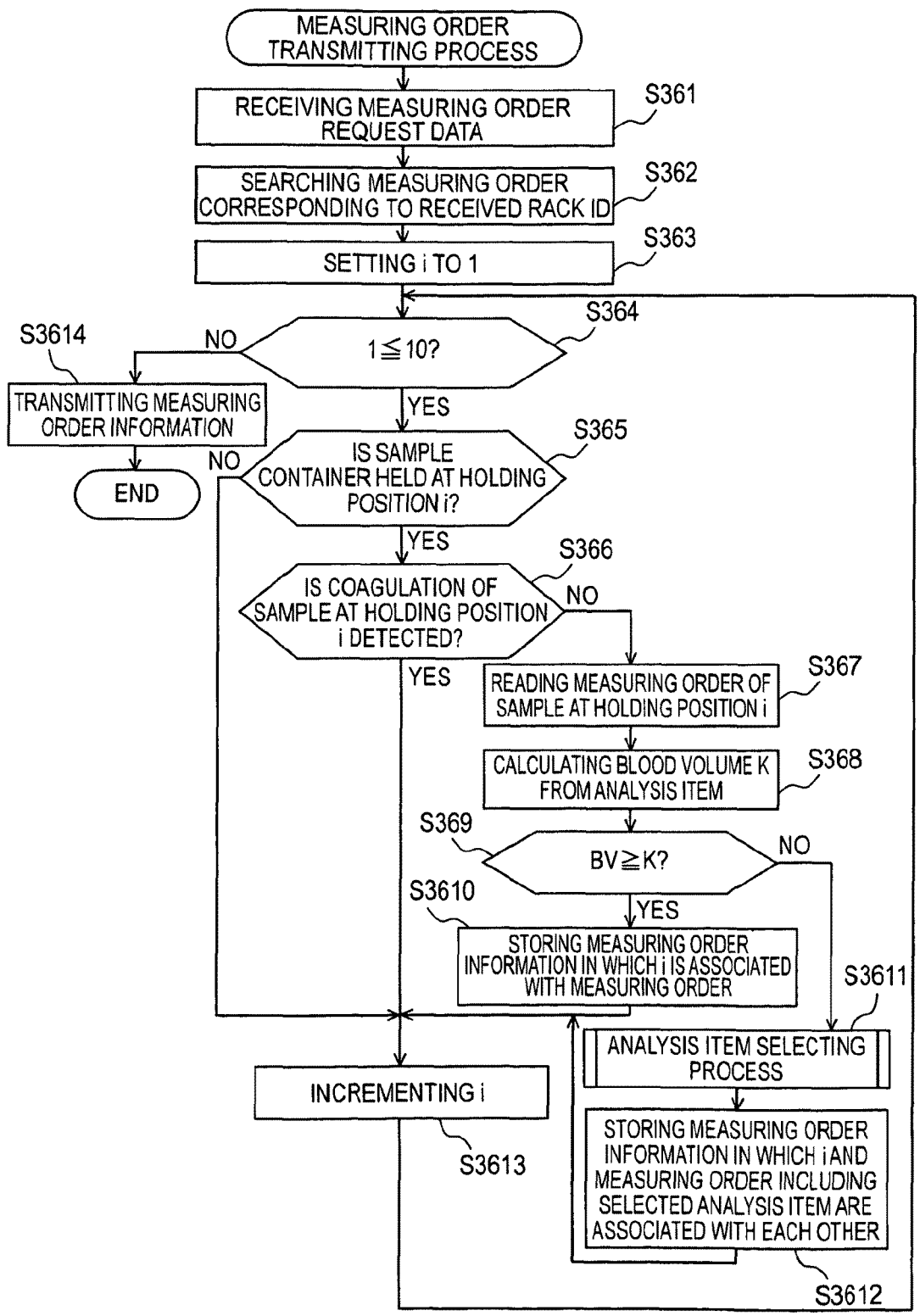

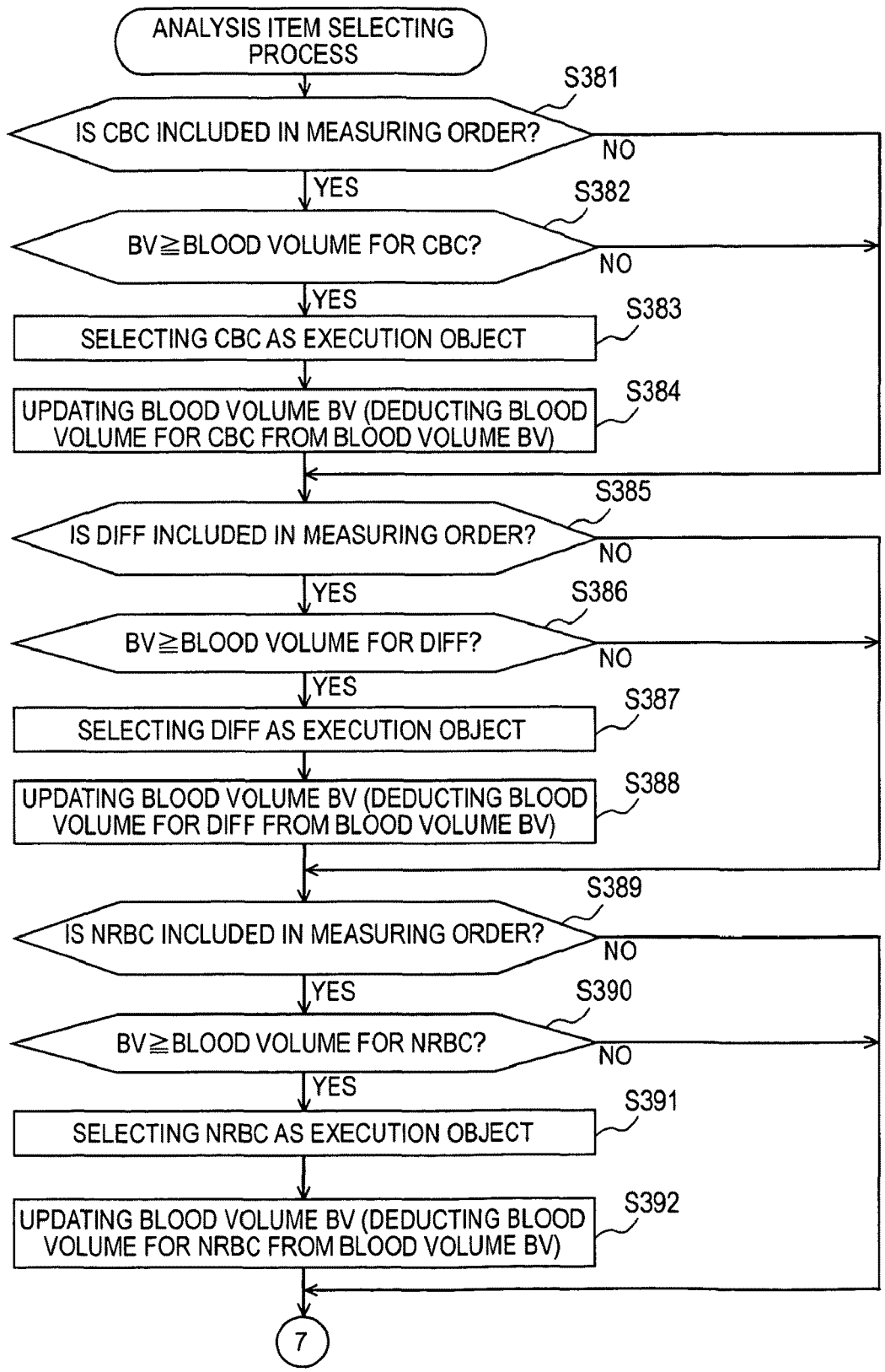

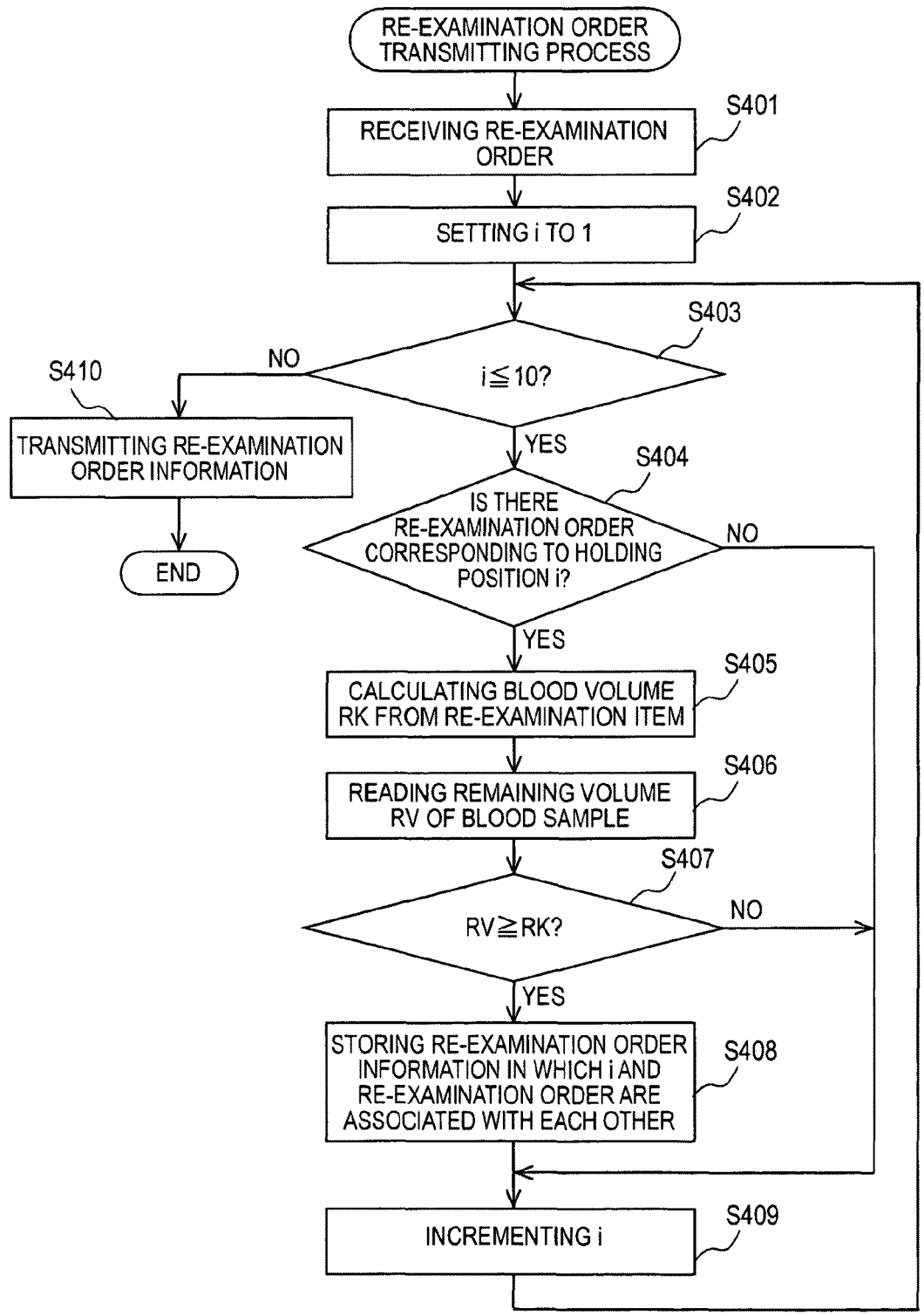

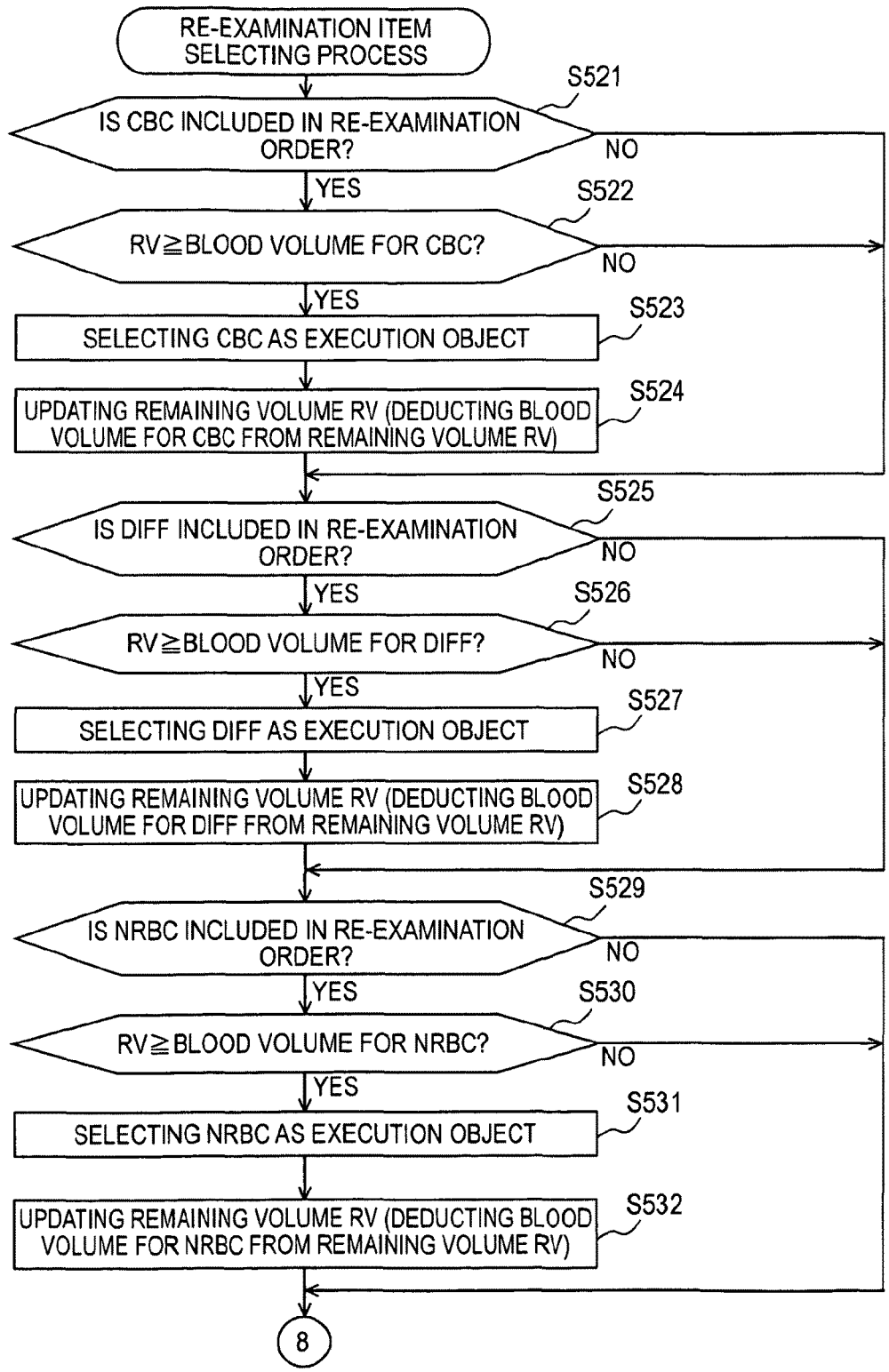

SAMPLE ANALYZER

RELATED APPLICATIONS

This application claims priority under 35 U.S.C. §119 to Japanese Patent Application No. 2008-200179 filed on Aug. 1, 2008, the entire content of which is hereby incorporated by reference.

FIELD OF THE INVENTION

The present invention relates to a sample analyzer which transports a sample container containing a sample such as blood and urine and measures the transported sample to analyze the sample.

BACKGROUND

In the past, there has been known a sample analyzer which aspirates a sample collected from a patient and contained in a sample container and analyzes the aspirated sample. In such a sample analyzer, when the volume of a sample contained in a sample container was insufficient for analysis, a problem occurred in that the analysis could not be performed in a normal manner or the analysis was stopped.

Japanese Laid-Open Patent Publication No. H10-115620 discloses a clinical autoanalyzer which calculates a specimen volume to be dispensed in a specimen container in advance and detects a specimen shortage before analyzing the specimen by comparing the specimen volume in the specimen container obtained by the height of the liquid surface of the specimen contained in the specimen container, the height of the specimen container and the kind of the specimen container with the specimen volume calculated in advance. This clinical autoanalyzer displays the specimen shortage on a display section to give a user a warning when the specimen shortage is detected.

However, in the clinical autoanalyzer disclosed in Japanese Laid-Open Patent Publication No. H10-115620, the user can recognize the specimen shortage by confirming the display of the display section, but it is necessary that the user performs a manual operation such as preparation of an additional specimen. Accordingly, a problem occurs in that user's time and effort is required.

BRIEF SUMMARY

The first aspect of the present invention is a sample analyzer, comprising: an imaging device for imaging a sample container which has translucency and contains a sample; a measuring device for aspirating the sample contained in the sample container and measuring the aspirated sample; a transporting device for transporting the sample container to a supply position for supplying the sample contained in the sample container to the measuring device; a sample volume obtainer for obtaining sample volume information relating to volume of the sample in the sample container, based on an image obtained by imaging the sample container by the imaging device; and a transport controller for controlling the transporting device to perform a transport operation in accordance with the sample volume information obtained by the sample volume obtainer.

The second aspect of the present invention is a sample analyzer, comprising: an imaging device for imaging a sample container which has translucency and contains a sample; a measuring device for aspirating the sample contained in the sample container and measuring the aspirated sample; a transporting device for transporting the sample container to a supply position for supplying the sample contained in the sample container to the measuring device; a sample volume obtainer for obtaining sample volume information relating to volume of the sample in the sample container, based on an image obtained by imaging the sample container by the imaging device; a controller for controlling the measuring device based on the sample volume information obtained by the sample volume obtainer.

BRIEF DESCRIPTION OF THE DRAWINGS

FIG. 15 is a flowchart showing the procedure of a measuring order obtaining process of a system control apparatus according to the first embodiment;

FIG. 27 is a schematic diagram showing the data structure of measuring order information;

FIG. 30A is a flowchart showing the flow of a measurement start instruction operation of an information processing unit according to the second embodiment;

FIG. 30B is a flowchart (first half) showing the flow of a sample measuring operation of a measuring unit according to the second embodiment;

FIG. 31A is a flowchart showing the procedure of a measuring order transmitting process of a system control apparatus according to a third embodiment;

FIG. 31B is a flowchart (first half) showing the procedure of an analysis item selecting process of the system control apparatus according to the third embodiment;

FIG. 32 is a flowchart showing the procedure of a re-examination order transmitting process of a system control apparatus according to a fourth embodiment;

FIG. 33B is a flowchart (first half) showing the procedure of a re-examination item selecting process of the system control apparatus according to the fifth embodiment.

DETAILED DESCRIPTION OF THE PREFERRED EMBODIMENTS

Hereinafter, preferred embodiments of the invention will be described with reference to the drawings.

First Embodiment

[Configuration of Blood Sample Analyzing System]

Figure 1:
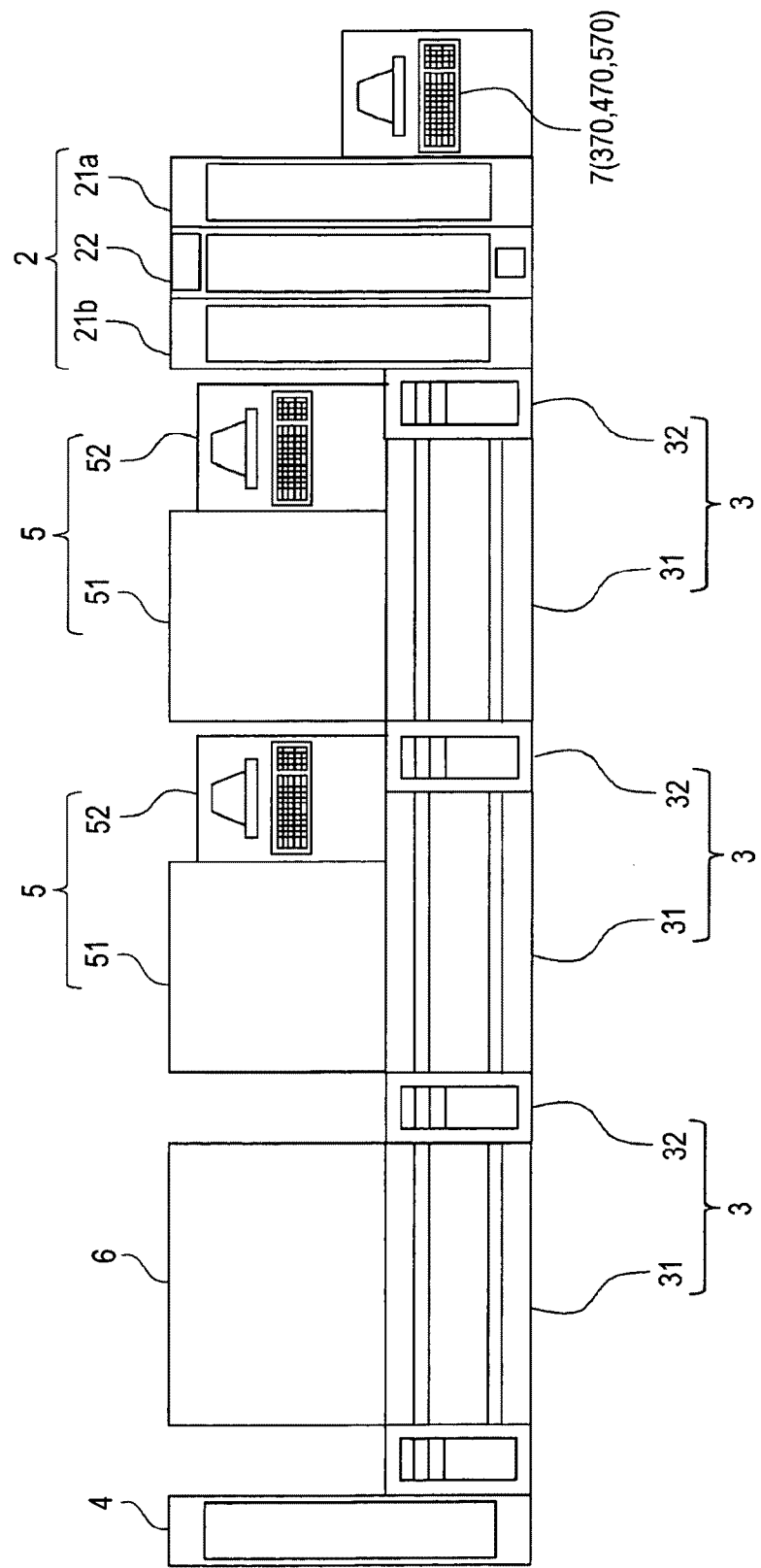
FIG. 1 is a schematic plan view showing the entire configuration of a blood sample analyzing system according to a first embodiment.

FIG. 1 is a schematic plan view showing the entire configuration of a blood sample analyzing system according to this embodiment. As illustrated in FIG. 1, a blood sample analyzing system 1 includes a sample putting apparatus 2, sample transport apparatuses 3, a sample storing apparatus 4, blood cell analyzing apparatuses 5, a smear preparing apparatus 6 and a system control apparatus 7.

<Configuration of Sample Putting Apparatus 2>

The sample putting apparatus 2 includes two sample delivery units 21a and 21b and a sample check unit 22 disposed between the two sample delivery units 21a and 21b. Sample racks storing plural sample containers can be placed in the sample putting apparatus 2. The sample putting apparatus performs coagulation determination and blood volume detection on a blood sample in a sample container stored in a sample rack. In addition, the sample putting apparatus 2 reads a bar-code of a bar-code label adhered to the sample container to obtain a specimen ID and to transmit the specimen ID, a coagulation determination result, and blood volume data to the system control apparatus 7.

Figure 2:
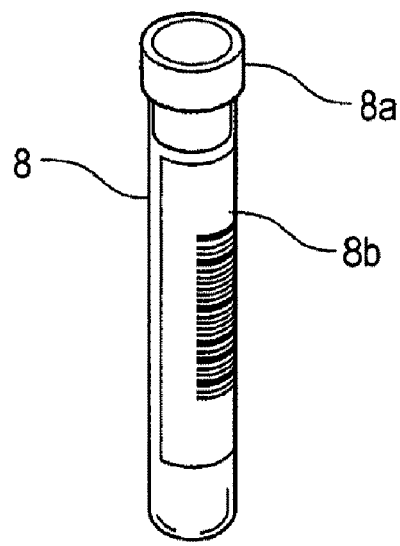
FIG. 2 is a perspective view showing the appearance of a sample container.
Figure 3:
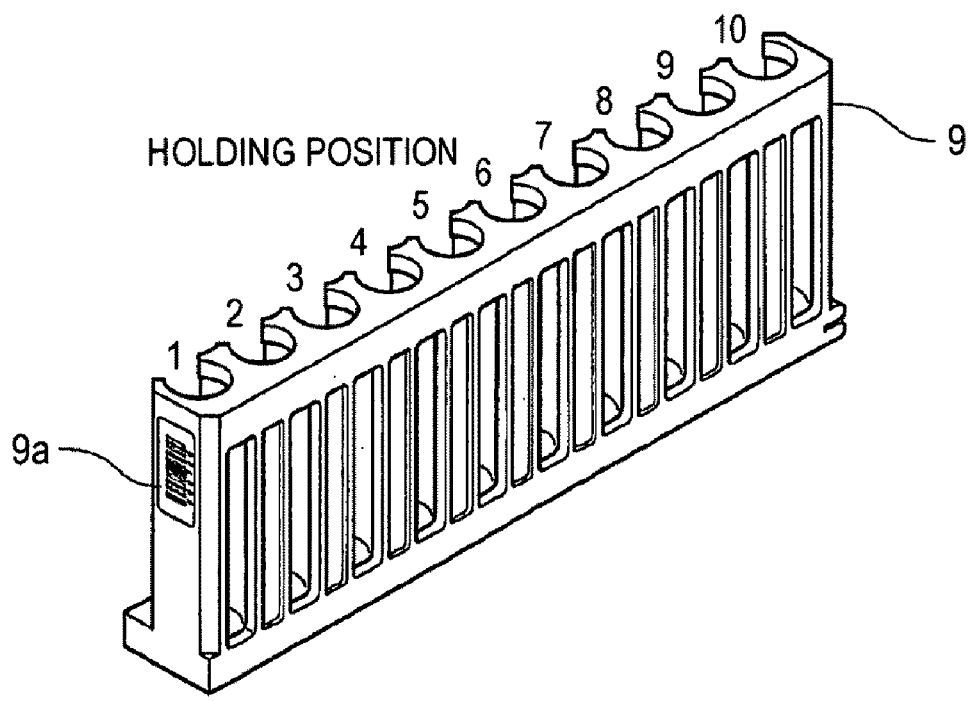
FIG. 3 is a perspective view showing the appearance of a sample rack.

FIG. 2 is a perspective view showing the appearance of the sample container and FIG. 3 is a perspective view showing the appearance of the sample rack. As shown in FIG. 2, a tube-shaped sample container 8 is open at a top end thereof. A blood sample collected from a patient is contained in the sample container 8 and the opening at the top end is sealed by a cap section 8a. The sample container 8 is made of translucent glass or synthetic resin and the blood sample therein can be visually confirmed. A bar-code label 8b is adhered to a side face of the sample container 8 and a bar-code indicating a specimen ID is printed on the bar-code label 8b. A sample rack 9 can hold ten of the sample containers 8 in parallel. In the sample rack 9, the sample containers 8 are held in a vertical state (erect state). A bar-code label 9a is adhered to a side face of the sample rack 9 and a bar-code indicating a rack ID is printed on the bar-code label 9a.

Figure 4:
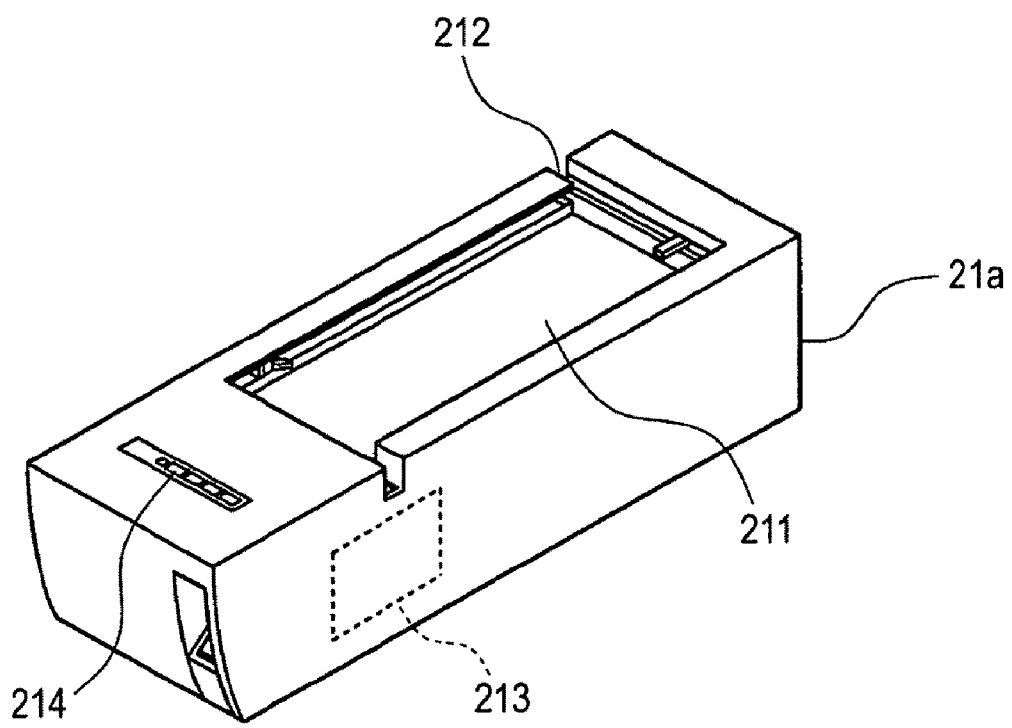
FIG. 4 is a perspective view showing the appearance configuration of a sample delivery unit.

FIG. 4 is a perspective view showing the appearance configuration of the sample delivery unit 21a. As shown in FIG. 4, the sample delivery unit 21a has a concave rack placing section 211 for placing the sample rack 9 storing the sample containers 8. The rack placing section 211 has a rectangular shape and the plural sample racks 9 can be simultaneously placed. At this time, the sample racks 9 are placed so that the sample containers 8 line up in a transverse direction. The rack placing section 211 is provided with an engaging section (not shown). The engaging section moves in a front-back direction while engaging with the sample rack 9 so as to move the sample rack 9 on the rack placing section 211. The sample delivery unit 21b is provided with a controller 213 composed of a CPU and a memory. The controller 213 controls the operating mechanisms such as the engaging section.

The sample delivery unit 21a is disposed on the right side of the sample check unit 22 (see FIG. 1 for reference). A left wall section on the inner side of the rack placing section 211 of the sample delivery unit 21a is missing and this missing portion serves as a rack delivery port 212. The sample rack 9 placed in the rack placing section 211 is moved in a direction toward the inner side from the front side, that is, in a backward direction to reach a position on the innermost side of the rack placing section 211, and is then conveyed toward the sample check unit 22 on the left side of the rack delivery port 212. In the sample delivery unit 21b disposed on the left side of the sample check unit 22, a right wall section on the inner side of a rack placing section 211 is missing so as to form a rack feed port (not shown) and the sample rack 9 is fed from the sample check unit 22 by the rack feed port. A left wall section on the front side (front face-side) of the rack placing section 211 of the sample delivery unit 21b is also missing (not shown) and this portion serves as a rack delivery port. The sample rack 9 fed from the rack feed port is moved to the front by the rack placing section 211 to reach the foremost position, and is then delivered to the left from the rack delivery port.

As shown in FIG. 4, the sample delivery unit 21a is provided with an operating panel 214. A user operates the operating panel 214 to issue an instruction to start analysis or an instruction to complete analysis to the blood sample analyzing system 1.

Figure 5:
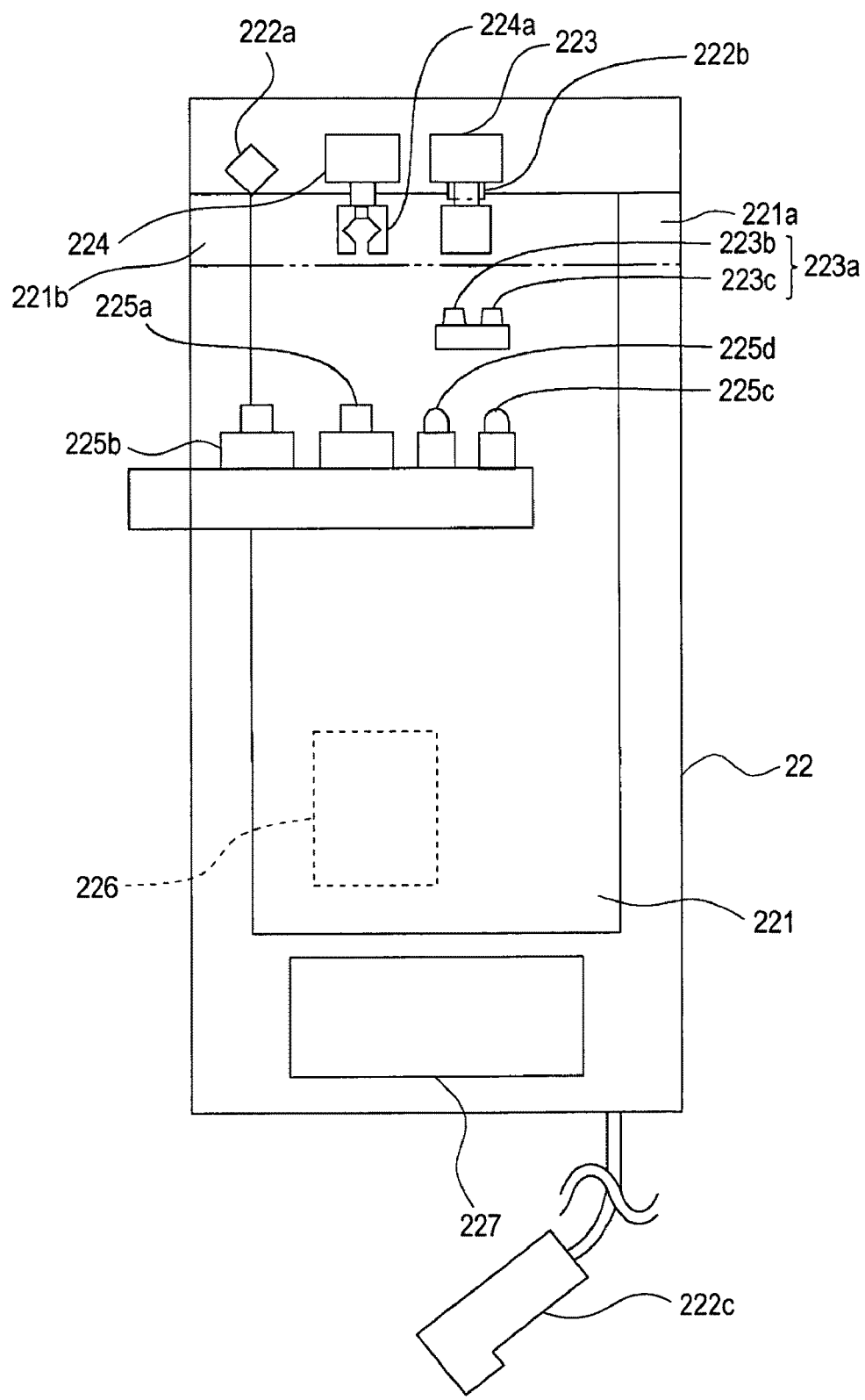
FIG. 5 is a plan view showing the configuration of a sample check unit.

FIG. 5 is a plan view showing the configuration of the sample check unit 22. As shown in FIG. 5, the sample check unit 22 includes a rack placing section 221 for placing the sample rack 9 fed from the sample delivery unit 21a, a bar-code reader 222a for reading a bar-code (rack bar-code) of the sample rack 9 on the rack placing section 221, a bar-code reader 222b for reading a bar-code (specimen bar-code) of the sample container 8 stored in the sample rack 9, a handy bar-code reader 222c which is manually operated by the user, a horizontal rotation mechanism 223 for horizontally rotating the sample container 8, an optical sensor 223a for detecting the presence or absence of the bar-code label 8b on the sample container 8, a sample container tilting mechanism 224 for taking out the sample container 8 from the sample rack 9 and tilting the sample container, two cameras 225a and 225b for imaging the sample container 8, a controller 226 which includes a CPU and a memory for controlling the operating mechanisms such as the horizontal rotation mechanism 223 and the sample container tilting mechanism 224, and a liquid crystal display section 227. The sample check unit 22 is connected to the system control apparatus 7 to perform data communication therewith, and is configured to transmit to the system control apparatus 7 the data read by the bar-code readers 222a, 222b and 222c and images captured by the cameras 225a and 225b.

The rack placing section 221 is rectangular in a plan view and is hollowed in a concave shape. A rack feed port 221a for feeding the sample rack 9 from the sample delivery unit 21a is provided in a right wall section at the inner end of the rack placing section 221. In addition, a rack delivery port 221b for delivering the sample rack 9 from the rack placing section 221 is provided in a left wall section at the inner end of the rack placing section 221. A portion on the innermost side of the rack placing section 221 (in the drawing, a portion shown by the two-dot chain line) is used as a transport path for transporting the sample rack 9 and a portion other than this portion is used to store the sample rack 9.

The bar-code reader 222a is provided with a light-emitting section and a light-receiving section (line sensor) (not shown), and is positioned so as to read the rack bar-code of the sample rack 9 on the transport path. The sample rack 9 fed from the rack feed port 221a is held by a holding means (not shown) and moved on the above-described transport path. The bar-code reader 222a reads the rack bar-code of the sample rack 9 on the transport path. Once read, the rack ID is transmitted to the system control apparatus 7.

The bar-code reader 222b is provided with a light-emitting section and a light-receiving section (line sensor) (not shown), and is positioned so as to read the specimen bar-code of the sample container 8 stored in the sample rack 9 on the transport path. The horizontal rotation mechanism 223 is provided above the bar-code reader 222b.

Figure 6:
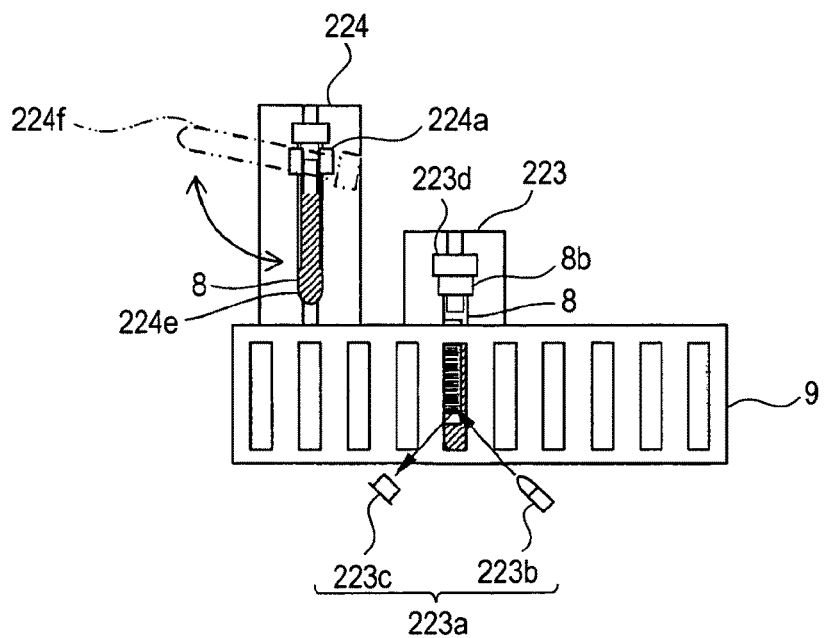
FIG. 6 is a front view schematically showing the configuration of a part of the sample check unit.

FIG. 6 is a front view schematically showing the configuration of a part of the sample check unit 22. As shown in FIG. 6, the horizontal rotation mechanism 223 has a contacting section 223d which is brought into contact with the upper end of the sample container 8 on the sample rack 9, and the contacting section 223d is configured to be horizontally rotated by a motor. When the contacting section 223d is horizontally rotated while brought into contact with the cap section 8a of the sample container 8, the sample container 8 is horizontally rotated in the sample rack 9. In addition, the optical sensor 223a is disposed in front of the horizontal rotation mechanism 223. The optical sensor 223a is composed of a light-emitting element 223b and a light-receiving element 223c. While the sample container 8 is horizontally rotated by the horizontal rotation mechanism 223, the sample container 8 is irradiated with light from the light-emitting element 223b and the light reflected is received by the light-receiving element 223c. When the bar-code label is disposed on the face reflecting the light of the light-emitting element 223b, a light-receiving level of the light-receiving element 223c exceeds a predetermined value, and when the bar-code label is not disposed on the face reflecting the light of the light-emitting element 223b, the light-receiving level is less than the predetermined value. The controller 226 checks the light-receiving level of the light-receiving element 223c of the optical sensor 223a while horizontally rotating the sample container 8, and stops the horizontal rotation operation of the horizontal rotation mechanism 223 at a position where the light-receiving level is equal to or less than the predetermined value. Accordingly, an angle of the sample container 8 is adjusted so that the face on which the bar-code label 8b is not disposed faces the front side.

As described above, when the face on which the bar-code label 8b is not disposed faces the front side, the bar-code reader 222b in the rear of the sample container 8 is opposed to the bar-code label 8b of the sample container 8. Herein, the bar-code reader 222b reads the specimen ID from the bar-code label 8b.

Furthermore, the optical sensor 223a can be vertically moved by a vertical driving mechanism (not shown). The optical sensor 223a is disposed in front of the sample rack 9 when the sample rack 9 is on the transport path of the rack placing section 221. When the sample rack 9 is moved to the front side of the rack placing section 221, the optical sensor 223a is lifted by the vertical driving mechanism up to a position which does not interfere with the movement of the sample rack 9.

Figure 7:
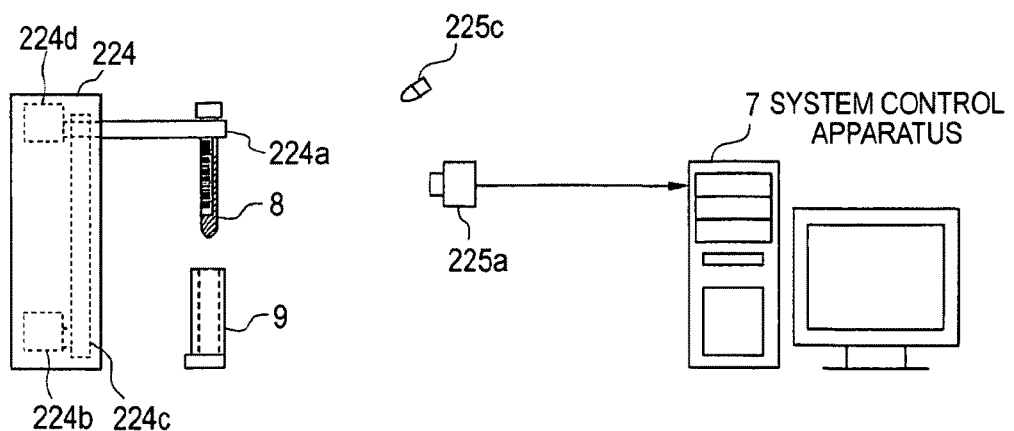
FIG. 7 is a side view showing the schematic configuration of a sample container tilting mechanism.

On the transport path of the rack placing section 221, the sample rack 9 is intermittently moved to the left in a pitch feeding manner in which the gap between the neighboring sample containers 8 is set as one pitch. The above-described sample container tilting mechanism 224 is provided so as to be positioned on the left side of the horizontal rotation mechanism 223 by a predetermined pitch. FIG. 7 is a side view showing the schematic configuration of the sample container tilting mechanism 224. The sample container tilting mechanism 224 includes a grasping section 224a for grasping the vicinity of the top end of the sample container from both the right and left sides, a motor 224b, and a belt 224c for connecting a rotation shaft of the motor 224b with the grasping section 224a, and the grasping section 224a can be vertically moved by the rotation of the motor 224b. Furthermore, the grasping section 224a is connected to a rotation shaft of a motor 224d and the grasping section 224a can be rotated around a center axis extending in a front-back direction by the rotation of the motor 224d.

The sample container 8, which is rotated by the horizontal rotation mechanism 223 so that the bar-code label 8b is not disposed on the front face, reaches the position of the sample container tilting mechanism 224 by moving the sample rack 9 to the left. Herein, when the grasping section 224a of the sample container tilting mechanism 224 grasps the vicinity of the top end of the sample container 8 and is lifted in such a state, the sample container 8 is taken out from the sample rack 9. When the sample container 8 is completely separated from the sample rack 9 and reaches a first imaging position 224e, the lift operation of the grasping section 224a is stopped. The camera 225a is disposed in front of the sample container 8 positioned at the first imaging position 224e. A white LED 225c is disposed at a predetermined position with respect to the camera 225a and the sample container 8 is illuminated by the white LED 225c.

Figure 8:
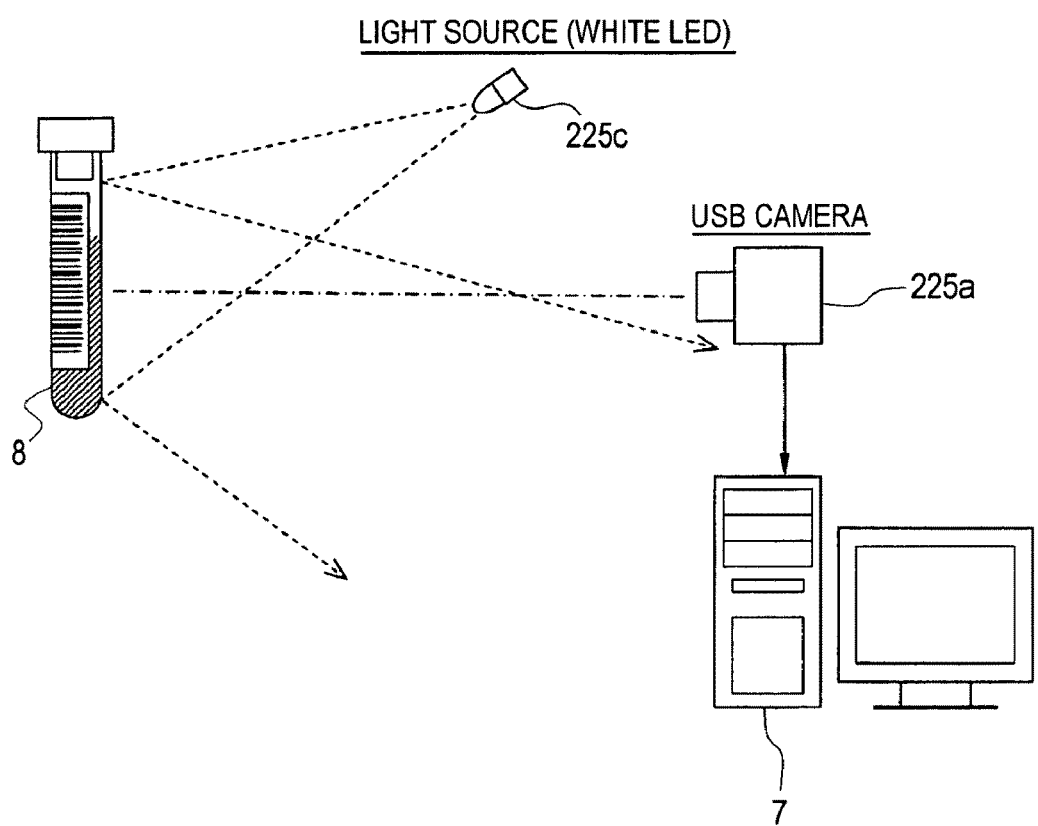
FIG. 8 is a schematic diagram for illustrating a positional relationship among a camera, a white LED and the sample container in the sample check unit, and a direction of the light emitted from the white LED.

FIG. 8 is a schematic diagram for illustrating a positional relationship among the camera 225a, the white LED 225c and the sample container 8, and a direction of the light emitted from the white LED. As shown in FIG. 8, the white LED 225c is disposed, so that the light is emitted toward the sample container 8 positioned at the first imaging position 224e and the light reflected from the sample container 8 does not directly enter the camera 225a positioned in front of the sample container 8. Accordingly, the camera 225a is not directly exposed to the reflected light and so-called halation by overexposure can be prevented.

The sample container 8 grasped at the first imaging position 224e by the grasping section 224a is imaged by the camera 225a while being in an erect state (vertical state), and the image data obtained in this manner is transmitted to the system control apparatus 7. After that, the grasping section 224a is vertically rotated by the motor 224d to tilt the sample container 8. As shown by the two-dot chain line in FIG. 6, the grasping section 224a is turned by a predetermined angle so that a bottom portion of the sample container 8 reaches a second imaging position 224f positioned higher than the cap section 8a. The camera 225b (see FIG. 5 for reference) is disposed in front of the sample container 8 positioned at the second imaging position 224f. A white LED 225d (see FIG. 5 for reference) is disposed at a predetermined position with respect to the camera 225b and the sample container 8 is illuminated by the white LED 225d. A relative positional relationship between the white LED 225d and the camera 225b is the same as a relative positional relationship between the white LED 225c and the camera 225a. That is, the white LED 225d is disposed, so that the light is emitted toward the sample container 8 positioned at the second imaging position 224f, and the light reflected from the sample container 8 does not directly enter the camera 225b positioned in front of the sample container 8.

The sample container 8 grasped at the second imaging position 224f by the grasping section 224a is imaged by the camera 225a while being tilted as described above, and the image data obtained in this manner is transmitted to the system control apparatus 7. The sample rack 9 in which all the sample containers 8 have been imaged is delivered from the rack delivery port 221b.

The bar-code reader 222c is provided with a light-emitting section and a light-receiving section (line sensor) (not shown), and is connected to a main body of the sample check unit 22 by a flexible cable for transmitting an electric signal. The bar-code reader 222c is operated when the user manually re-reads a bar-code which cannot be read by the bar-code reader 222b.

<Configuration of Sample Transport Apparatus 3>

Next, the configuration of the sample transport apparatus 3 will be described. As shown in FIG. 1, the blood sample analyzing system 1 is provided with the three sample transport apparatuses 3. The sample transport apparatuses 3 are disposed in front of the blood cell analyzing apparatuses 5 and the smear preparing apparatus 6, respectively. The neighboring sample transport apparatuses 3 are connected to each other and can deliver the sample rack 9. The rightmost sample transport apparatus 3 is connected to the above-described sample putting apparatus 2 to feed the sample rack 9 conveyed from the sample putting apparatus 2. The leftmost sample transport apparatus 3 is connected to the sample storing apparatus 4 to convey the sample rack 9 toward the sample storing apparatus 4.

Figure 9:
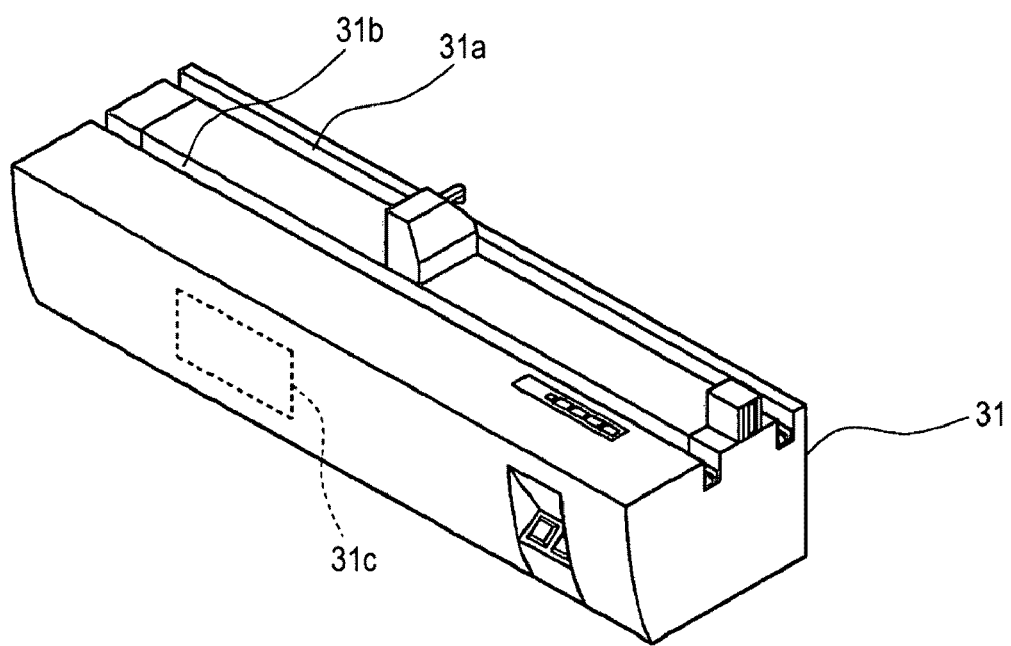
FIG. 9 is a perspective view showing the configuration of a conveyor.
Figure 10:
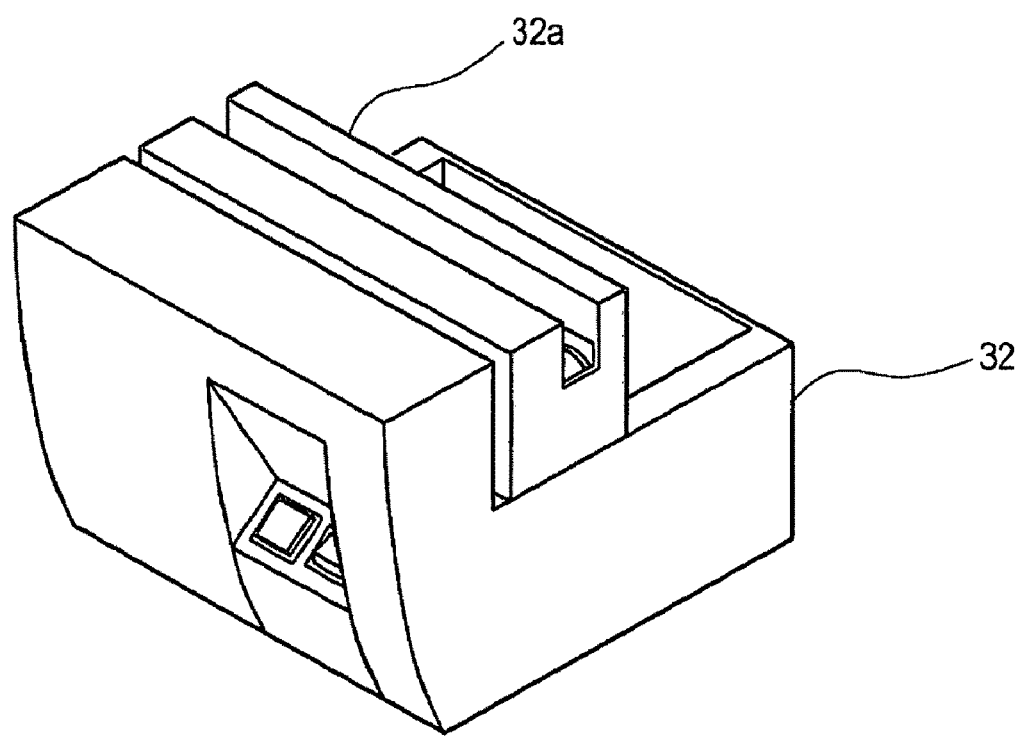
FIG. 10 is a perspective view showing the configuration of a rack slider.

The respective sample transport apparatuses 3 are provided with a conveyor 31 and a rack slider 32. FIG. 9 is a perspective view showing the configuration of the conveyor 31 and FIG. 10 is a perspective view showing the configuration of the rack slider 32. As shown in FIG. 9, the conveyor 31 is provided with two rack transport paths 31a and 31b extending in a horizontal direction. The rack transport path 31a at the rear side is a measuring line for transporting the sample rack 9 containing a sample to be supplied to the blood cell analyzing apparatus 5 or the smear preparing apparatus 6. The rack transport path 31b at the front side is a skip line for transporting the sample rack 9 not containing a sample to be supplied to the blood cell analyzing apparatus 5 or the smear preparing apparatus 6. In addition, the conveyor 31 is provided with a controller 31c including a CPU and a memory and controlling the operating mechanism.

The rack slider 32 is disposed on the right side of the conveyor 31 to sort and put the sample racks 9 into the measuring line 31a and the skip line 31b of the conveyor 31. The rack slider 32 is provided with one movable transport path 32a and the movable transport path 32a can be moved in a front-back direction by a motor (not shown). The above-described controller 31c controls the operation of the movable transport path 32a.

In addition, the respective sample transport apparatuses 3 are provided with a rack bar-code reader (not shown) and the rack IDs read by the bar-code reader are provided to the controller 31c. Moreover, the sample transport apparatus 3 is connected to the system control apparatus 7 to communicate therewith and is configured to receive a measuring order from the system control apparatus 7. The controller 31c determines whether a sample to be supplied to the blood cell analyzing apparatus 5 or the smear preparing apparatus 6 is contained in the sample rack 9 on the basis of the measuring order provided from the system control apparatus 7 and the rack ID read by the bar-code reader. When the sample rack 9 containing the sample to be supplied to the blood cell analyzing apparatus 5 or the smear preparing apparatus 6 is fed to the rack slider 32, the movable transport path 32a is moved to the back to deliver the sample rack 9 to the measuring line 31a. When the sample rack 9 not containing the sample to be supplied to the blood cell analyzing apparatus 5 or the smear preparing apparatus 6 is fed to the rack slider 32, the movable transport path 32a is moved to the front to deliver the sample rack 9 to the skip line 31b. That is, the sample rack 9 containing only a sample which is not an analysis target of the blood cell analyzing apparatus 5 is transported to the skip line 31b in the sample transport apparatus 3 disposed in front of the blood cell analyzing apparatus 5. The sample rack 9 containing only a sample which is not a target for preparing a smear by the smear preparing apparatus 6 is transported to the skip line 31b in the sample transport apparatus 3 disposed in front of the smear preparing apparatus 6. When the sample rack 9 contains a sample, which is an analysis target of the blood cell analyzing apparatus 5, the sample rack 9 is transported to the measuring line 31a in the sample transport apparatus 3 disposed in front of the blood cell analyzing apparatus 5.

When the sample rack 9 is delivered to the measuring line 31a, the controller 31c repeats an operation of: moving the sample container which is a target of analysis (smear preparing process) to an aspiration position where the blood cell analyzing apparatus 5 (smear preparing apparatus 6) aspirates the sample; and moving the sample container which is the next analysis target (target for smear preparing process) to the aspiration position after the blood cell analyzing apparatus 5 (smear preparing apparatus 6) completes the aspiration of the sample.

<Configuration of Sample Storing Apparatus 4>

The sample storing apparatus 4 receives the sample rack 9, in which the analysis or smear preparing is completed, from the sample transport apparatus 3, and stores the sample rack. Since the configuration of the sample storing apparatus is the same as those of the sample delivery units 21a and 21b, a description thereof will be omitted.

<Configuration of Blood Cell Analyzing Apparatus 5>

The blood cell analyzing apparatus 5 as an optical flow cytometry type multiple blood cell analyzing apparatus obtains the fluorescent intensity, the side-scattered light intensity and the like of blood cells included in a blood sample, classifies the blood cells included in the sample on the basis of the above intensities, and counts the number of blood cells for each type. Moreover, the blood cell analyzing apparatus 5 creates and displays a scattergram in which the classified blood cells are color-coded for each type. The blood cell analyzing apparatus 5 includes a measuring unit 51 for measuring a blood sample and an information processing unit 52 for processing measuring data output from the measuring unit 51 and displaying an analysis result of the blood sample.

Figure 11:
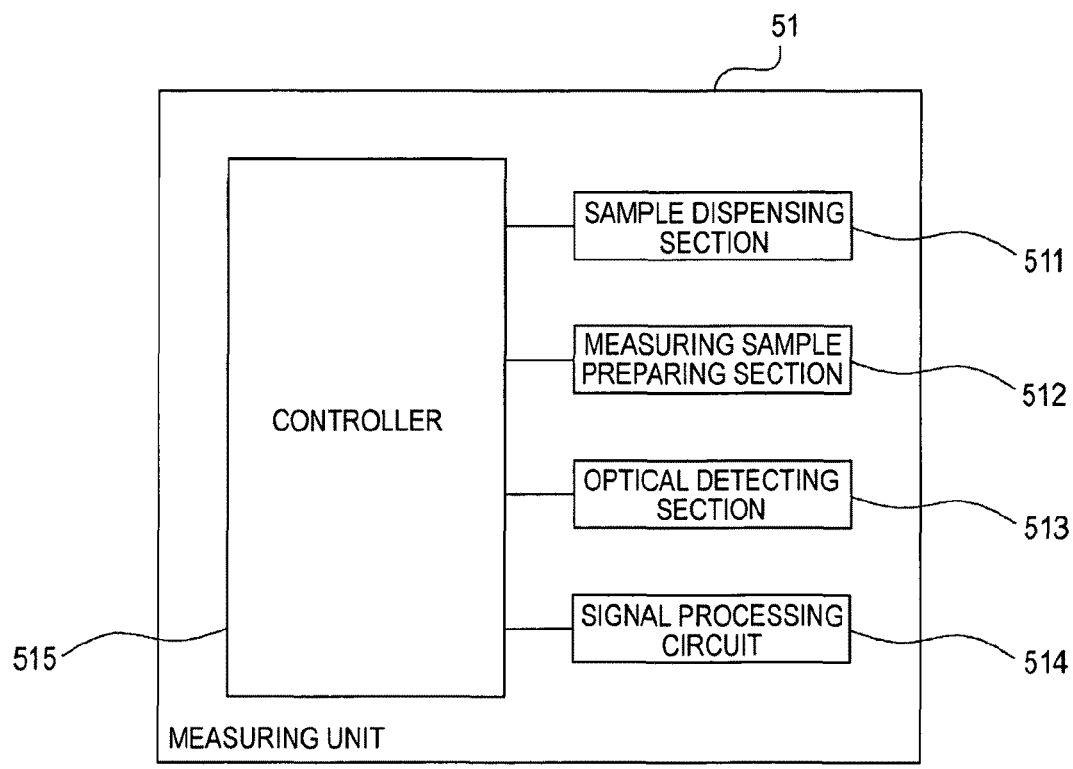
FIG. 11 is a block diagram showing the schematic configuration of a measuring unit according to the first embodiment.

FIG. 11 is a block diagram showing the schematic configuration of the measuring unit 51. The measuring unit 51 includes a sample dispensing section 511, a measuring sample preparing section 512, an optical detecting section 513, a signal processing circuit 514 and a controller 515.

The sample dispensing section 511 is provided with an aspiration tube (not shown) and the aspiration tube is stuck into the cap section 8a of the sample container 8 in the sample rack 9 transported on the measuring line 31a of the sample transport apparatus 3 to aspirate a blood sample from the sample container 8. The measuring sample preparing section 512 is provided with a mixing container (not shown) to mix and stir the blood sample dispensed by the sample dispensing section 511 with a reagent and a diluent and prepare a measuring sample.

The optical detecting section 513 is provided with a flow cell (not shown) to form a narrow flow of the measuring sample by supplying the measuring sample to the flow cell and exposing the measuring sample to light to obtain a side-scattered light signal, a forward-scattered light signal and a fluorescent signal by an optical sensor. These signals are output to the signal processing circuit 514. The signal processing circuit 514 processes an electric signal output from the optical detecting section 513. The signal processing circuit 514 obtains parameters such as peaks and pulse widths of the side-scattered light signal, the forward-scattered light signal and the fluorescent signal.

The controller 515 is provided with a CPU and a memory, and is connected to the sample transport apparatus 3 to perform data communication therewith. The controller 515 controls the sample dispensing section 511, the measuring sample preparing section 512, the optical detecting section 513 and the signal processing circuit 514 in accordance with an analysis item provided from the sample transport apparatus 3, and performs a measuring operation corresponding to the analysis item. In addition, the controller is configured to transmit measuring data including the parameters obtained by the signal processing circuit 514 to the information processing unit 52.

The measuring unit 51 can be operated in two operating modes which are a normal-measurement mode and a micro-measurement mode. In the micro-measurement mode, a smaller volume of a blood sample than in the normal-measurement mode is aspirated by the sample dispensing section 511, a measuring sample of a higher dilution ratio than in the normal-measurement mode is prepared by the measuring sample preparing section 512, and the measuring sample is optically measured by the optical detecting section 513. When the measurement in the micro-measurement mode is performed by the measuring unit 51, an analysis result obtained by the information processing unit 52 is corrected in accordance with the dilution ratio of the measuring sample. Accordingly, even when a slight volume of blood is measured, an analysis result can be obtained with excellent accuracy.

Figure 12:
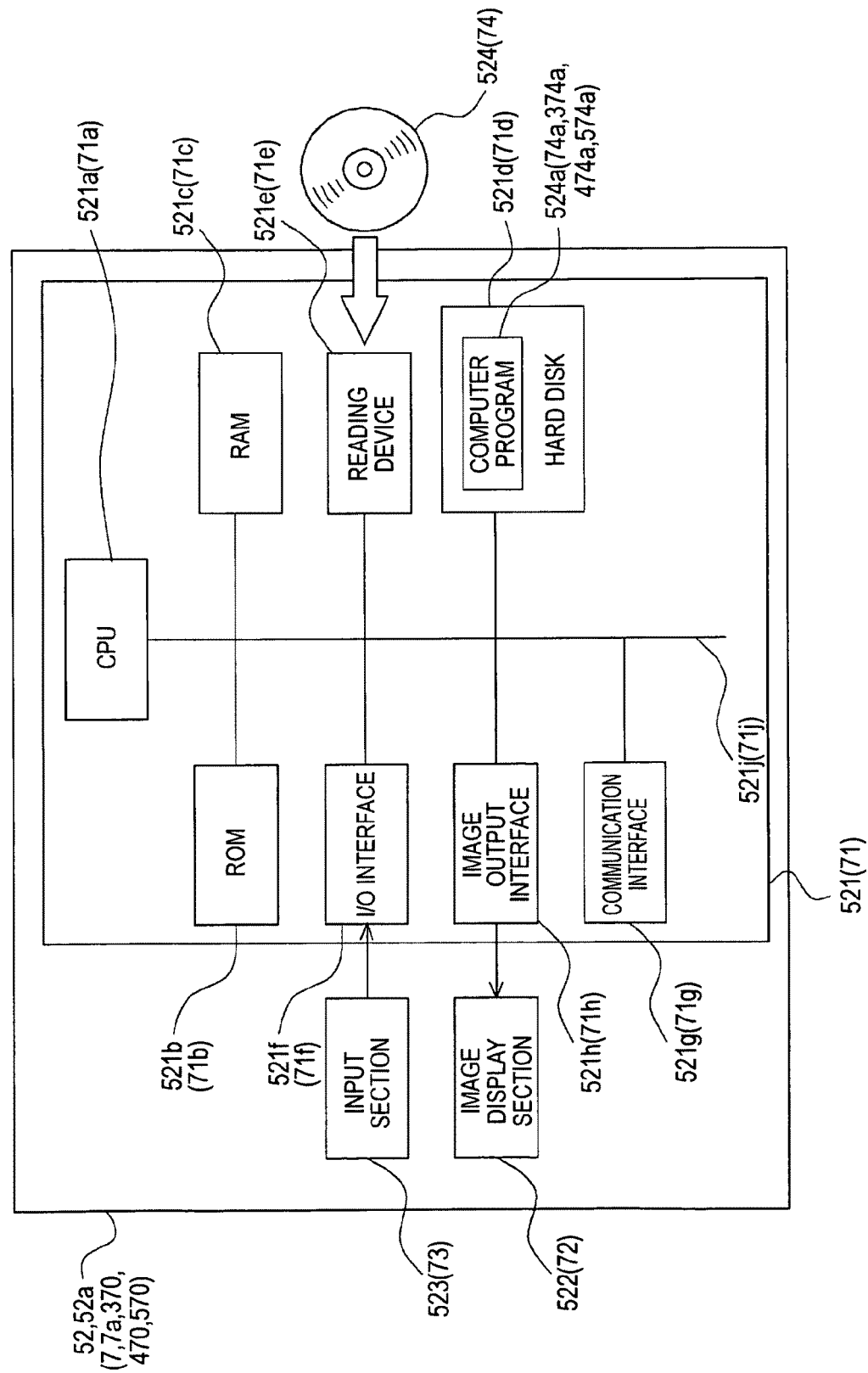
FIG. 12 is a block diagram showing the configuration of an information processing unit according to the first embodiment.

Next, the configuration of the information processing unit 52 will be described. The information processing unit 52 is composed of a computer. FIG. 12 is a block diagram showing the configuration of the information processing unit 52. The information processing unit 52 is realized by a computer 52a. As shown in FIG. 12, the computer 52a includes a main body 521, an image display section 522 and an input section 523. The main body 521 includes a CPU 521a, a ROM 521b, a RAM 521c, a hard disk 521d, a reading device 521e, an I/O interface 521f, a communication interface 521g and an image output interface 521h. The CPU 521a, ROM 521b, RAM 521c, hard disk 521d, reading device 521e, I/O interface 521f, communication interface 521g and image output interface 521h are connected to each other by a bus 521j.

The CPU 521a can execute a computer program loaded to the RAM 521c. The CPU 521a executes an analysis program 524a to be described later, so that the computer 52a functions as the information processing unit 52.

The ROM 521b is composed of a mask ROM, a PROM, an EPROM an EEPROM or the like and the computer program executed by the CPU 521a and data used for the computer program are recorded in the ROM.

The RAM 521c is composed of a SRAM, a DRAM or the like. The RAM 521c is used to read the analysis program 524a recorded in the hard disk 521d. Moreover, the RAM is used as an operating area of the CPU 521a when the CPU 521a executes a computer program.

In the hard disk 521d, various computer programs for execution by the CPU 521a, such as an operating system and an application program, and data which are used to execute the computer programs are installed. The analysis program 524a to be described later is also installed in the hard disk 521d.

The reading device 521e is composed of a flexible disk drive, a CD-ROM drive, a DVD-ROM drive or the like and can read the computer program or data recorded in a portable recording medium 524. In the portable recording medium 524, the analysis program 524a for prompting the computer to function as the information processing unit 52 is stored. The computer 52a can read the analysis program 524a from the portable recording medium 524 and install the analysis program 524a in the hard disk 521d.

The analysis program 524a is provided by the portable recording medium 524 and can be also provided from an external device, which is connected to the computer 52a by an electric communication line (which may be wired or wireless) to communicate therewith, through the electric communication line. For example, the analysis program 524a is stored in a hard disk of a server computer on the internet and the computer 52a accesses the server computer to download the computer program and install the computer program in the hard disk 521d.

Furthermore, in the hard disk 521d, for example, a multi-tasking operating system such as Windows (registered trade name), which is made and distributed by Microsoft corporation in America, is installed. In the following description, the analysis program 524a according to this embodiment operates on the above operating system.

The I/O interface 521f is composed of, for example, a serial interface such as USB, IEEE1394 or RS-232C, a parallel interface such as SCSI, IDE or IEEE1284, and an analog interface including a D/A converter and an A/D converter. The input section 523 composed of a keyboard and a mouse is connected to the I/O interface 521f and the user uses the input section 523 to input data to the computer 52a.

The communication interface 521g is an Ethernet (registered trade name) interface. The communication interface 521g is connected to the measuring unit 51 via a LAN. Thanks to the communication interface 521g, the computer 52a sends and receives data to and from the measuring unit 51 connected to the LAN by using a predetermined communication protocol.

The image output interface 521h is connected to the image display section 522 composed of a LCD or a CRT to output a picture signal corresponding to the image data provided from the CPU 521a to the image display section 522. The image display section 522 displays an image (screen) in accordance with an input picture signal.

<Configuration of Smear Preparing Apparatus 6>

The smear preparing apparatus 6 aspirates a blood sample so as to deliver drops of it onto a slide glass, spreads and dries the blood sample on the slide glass, and supplies a stain solution to the slide glass to stain the blood on the slide glass. In this manner, the smear preparing apparatus prepares a smear.

Figure 13:
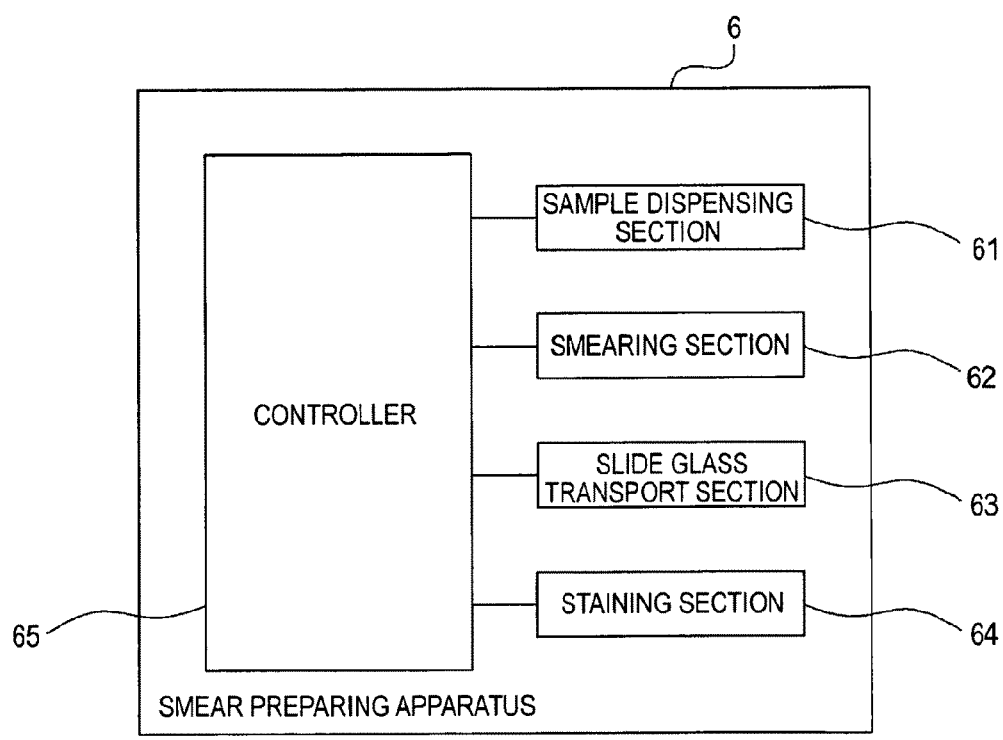
FIG. 13 is a block diagram showing the schematic configuration of a smear preparing apparatus.

FIG. 13 is a block diagram showing the schematic configuration of the smear preparing apparatus 6. As shown in FIG. 13, the smear preparing apparatus 6 includes a sample dispensing section 61, a smearing section 62, a slide glass transport section 63, a staining section 64 and a controller 65.

The sample dispensing section 61 is provided with an aspiration tube (not shown) and the aspiration tube is stuck into the cap section 8a of the sample container 8 in the sample rack 9 transported on the measuring line 31a of the sample transport apparatus 3 to aspirate a blood sample from the sample container 8. The sample dispensing section 61 is configured to drip the aspirated blood sample onto a slide glass. The smearing section 62 is configured to smear and dry the blood sample dripped onto the slide glass and perform printing on the slide glass.

The slide glass transport section 63 is provided to receive the slide glass on which the blood sample is smeared by the smearing section 62 in a cassette (not shown) and to transport the cassette. The staining section 64 supplies a stain solution to the slide glass in the cassette transported to a staining position by the slide glass transport section 63. The controller 65 controls the sample dispensing section 61, the smearing section 62, the slide glass transport section 63 and the staining section 64 in accordance with a smear preparing instruction issued from the sample transport apparatus 3 so as to perform the above smear preparing operation. When the smear preparation is completed, the controller 65 transmits a notification of the completion of the preparation of the smear to the sample transport apparatus 3.

<Configuration of System Control Apparatus 7>

The system control apparatus 7 is composed of a computer and controls the entire blood sample analyzing system 1. The system control apparatus 7 receives a specimen ID and a rack ID from the sample putting apparatus 2 so as to obtain a measuring order from a host computer (not shown) by the specimen ID as a key. Furthermore, the system control apparatus 7 performs image processing of the images captured by and output from the cameras 225a and 225b to determine whether a blood sample in a storing container is coagulated and to detect the volume of the blood sample in the sample container. Moreover, the system control apparatus 7 transmits the measuring order to the sample transport apparatus 3.

The system control apparatus 7 is realized by a computer 7a. As shown in FIG. 12, the computer 7a includes a main body 71, an image display section 72 and an input section 73. The main body 71 includes a CPU 71a, a ROM 71b, a RAM 71c, a hard disk 71d, a reading device 71e, an I/O interface 71f, a communication interface 71g and an image output interface 71h. The CPU 71a, ROM 71b, RAM 71c, hard disk 71d, reading device 71e, I/O interface 71f, communication interface 71g and image output interface 71h are connected to each other by a bus 71j.

In the hard disk 71d, various computer programs for execution by the CPU 71a, such as an operating system and an application program, and data which are used to execute the computer programs are installed. A system control program 74a to be described later is also installed in the hard disk 71d.

The reading device 71e is composed of a flexible disk drive, a CD-ROM drive, a DVD-ROM drive or the like and can read the computer program or data recorded in a portable recording medium 74. In the portable recording medium 74, the system control program 74a for prompting the computer to function as the system control apparatus 7 is stored. The computer 7a can read the system control program 74a from the portable recording medium 74 to install the system control program 74a in the hard disk 71d.

The I/O interface 71f is composed of, for example, a serial interface such as USB, IEEE1394 or RS-232C, a parallel interface such as SCSI, IDE or IEEE1284, and an analog interface including a D/A converter and an A/D converter. The input section 73 composed of a keyboard and a mouse is connected to the I/O interface 71f and the user uses the input section 73 to input data to the computer 52a. In addition, the cameras 225a and 225b provided in the above-described sample check unit 22 are connected to the I/O interface 71f to take the images captured by the cameras 225a and 225b.

The communication interface 71g is an Ethernet (registered trade name) interface. The communication interface 71g is connected to the sample putting apparatus 2, the sample transport apparatus 3, the sample storing apparatus 4 and the host computer (not shown) via a LAN. Via the communication interface 71g, the computer 7a sends and receives data to and from the above respective apparatuses connected to the LAN by using a predetermined communication protocol.

Since the other configurations of the system control apparatus 7 are the same as the configurations of the above-described information processing unit 52, a description thereof will be omitted.

[Operation of Blood Sample Analyzing System]

Hereinafter, an operation of the blood sample analyzing system 1 according to this embodiment will be described.

<Operation of Sample Putting Apparatus 2>

Figure 14A:
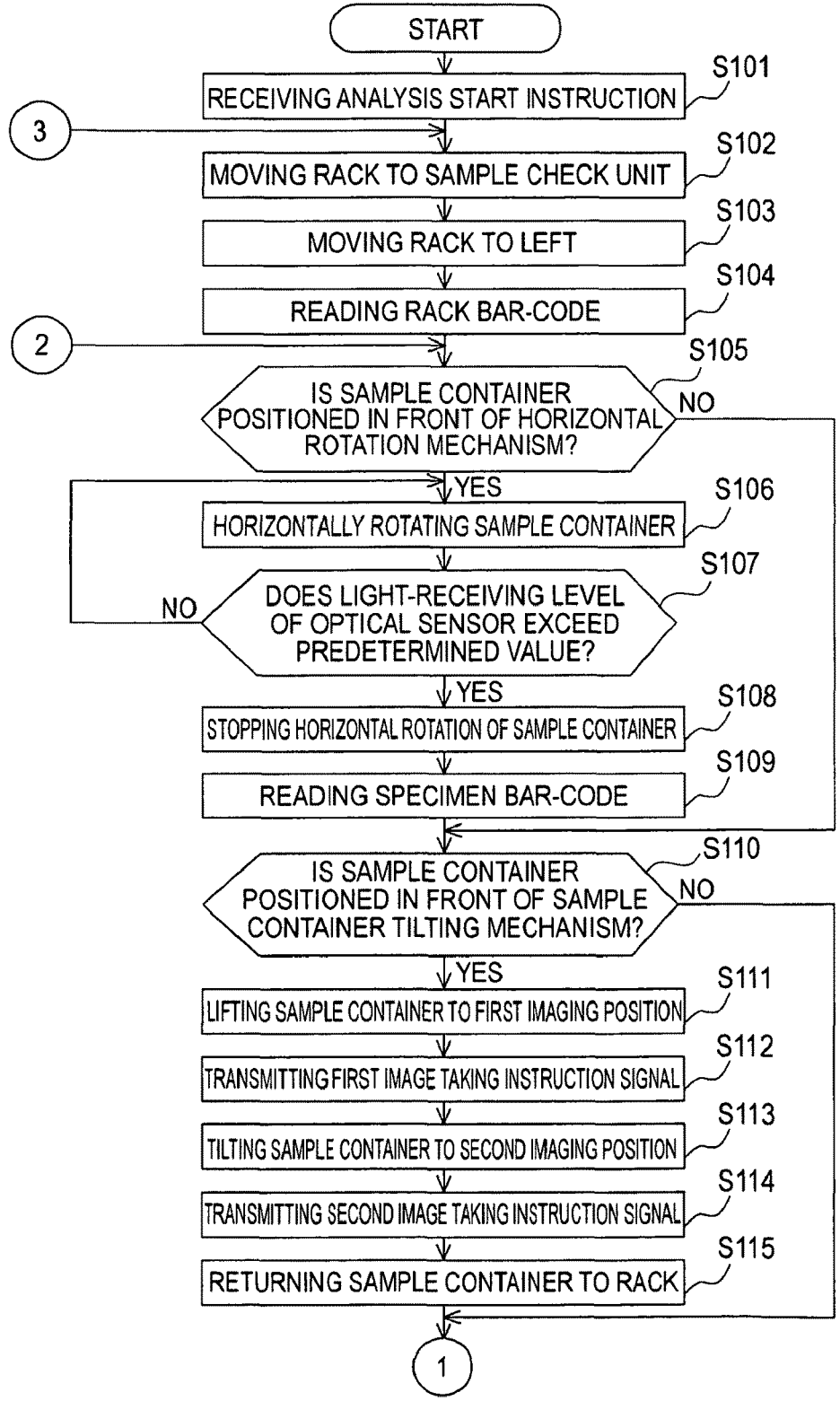
FIG. 14A is a flowchart (first half) showing the flow of an operation of a sample putting apparatus according to the first embodiment.
Figure 14B:
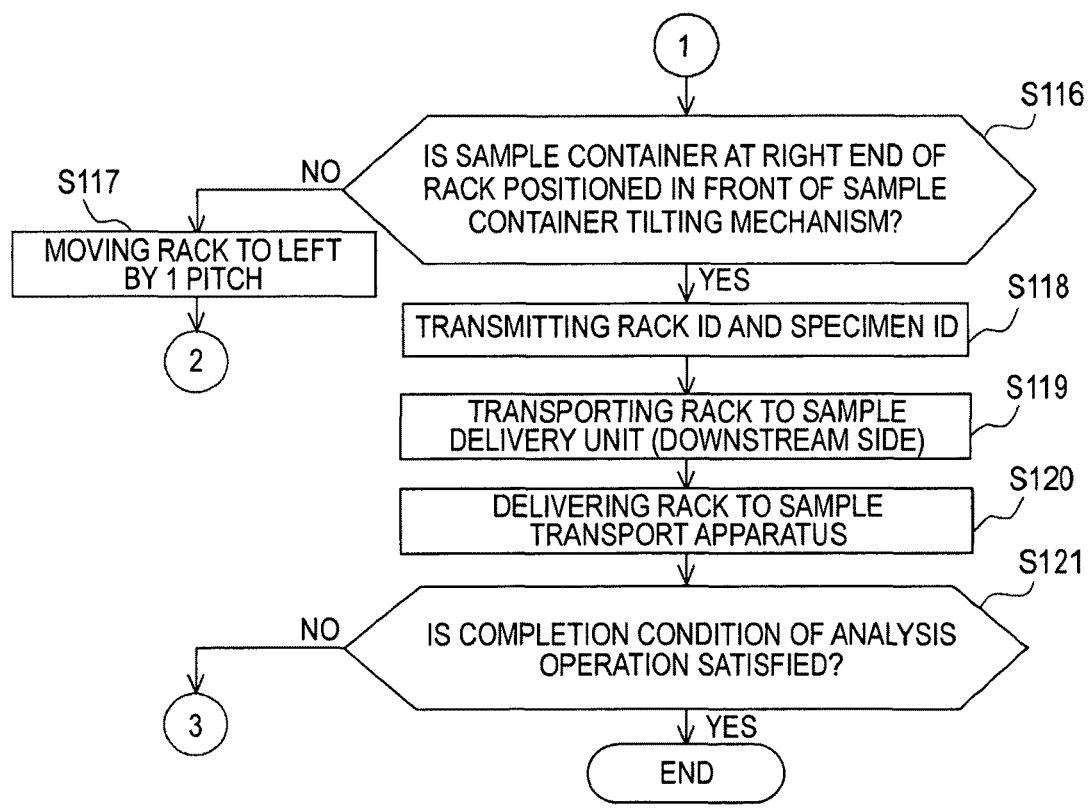
FIG. 14B is a flowchart (second half) showing the flow of the operation of the sample putting apparatus according to the first embodiment.

FIGS. 14A and 14B are flowcharts showing the flow of an operation of the sample putting apparatus 2. The user places the sample rack 9 storing the sample container 8 in the rack placing section 211 of the sample delivery unit 21a and operates the operating panel 214 of the sample delivery unit 21a to issue an instruction to start analysis to the blood sample analyzing system 1. The controller 213 of the sample delivery unit 21a receives the instruction to start analysis (Step S101) and starts movement of the sample rack 9 in accordance with the instruction (Step S102). The sample rack 9 placed in the rack placing section 211 of the sample delivery unit 21a is moved to the back on the rack placing section 211. Then, the sample rack 9 is moved to the left to be transferred to the sample check unit 22.

By the controller 226 of the sample check unit 22, the sample rack 9 fed to the sample check unit 22 is moved for every pitch to the left on the transport path of the rack placing section 221 (Step S103). A rack bar-code of the sample rack 9 is read by the bar-code reader 222a and provided to the controller 226 (Step S104). The controller 226 determines whether the sample container 8 is positioned in front of the horizontal rotation mechanism 223 (Step S105). This process is performed, by referring to, for example, a light-receiving level of the light-receiving element 223c of the optical sensor 223a. When the sample container 8 is not positioned in front of the horizontal rotation mechanism 223 (No in Step S105), the controller 226 returns the process to Step S110. On the other hand, when the sample container 8 is positioned in front of the horizontal rotation mechanism 223 (Yes in Step S105), the controller 226 compares the light-receiving level of the light-receiving element 223c of the optical sensor 223a with a predetermined value (Step S107), while bringing the contacting section 223d into contact with the cap section 8a of the sample container 8 and rotating the contacting section (Step S106). When the light-receiving level is equal to or less than the predetermined value (No in Step S107), the controller returns the process to Step S106 and thus the horizontal rotation of the sample container 8 is continued. On the other hand, when the light-receiving level exceeds the predetermined value (Yes in Step S107), the controller 226 stops the horizontal rotation of the contacting section 223d (Step S108) and causes the bar-code reader 222b to read the specimen bar-code (Step S109).

Subsequently, the controller 226 determines whether the sample container 8 is disposed in front of the sample container tilting mechanism 224 (Step S110). This process is performed by, for example, determining how many times the sample container 8 disposed in front of the horizontal rotation mechanism 223 has been subjected to pitch feeding. When the sample container 8 is not disposed in front of the sample container tilting mechanism 224 (No in Step S110), the controller 226 performs a process of Step S116. When the sample container 8 is disposed in front of the sample container tilting mechanism 224 (Yes in Step S110), the controller 226 grasps the sample container 8 by the grasping section 224a to lift the sample container to the first imaging position on the upper side (Step S111), and transmits a first image taking instruction signal to the system control apparatus 7 (Step S112). As described later, the system control apparatus 7 takes an image captured by the camera 225a when receiving the first image taking instruction signal, and then performs image processing on the image and detects the blood volume in the sample container 8.

Next, the controller 226 vertically turns the grasping section 224a by a predetermined angle to tilt the sample container 8 to the second imaging position (Step S113) and transmits a second image taking instruction signal to the system control apparatus 7 (Step S114). As described later, the system control apparatus 7 takes an image captured by the camera 225b when receiving the second image taking instruction signal, and then performs image processing on the image and determines the presence or absence of blood coagulation in the sample container 8.

Next, the controller 226 turns the grasping section 224a in the counter direction to return the sample container 8 to the vertical state again, and moves the grasping section 224a downward to store the sample container 8 in the sample rack 9 (Step S115).

Herein, in order to simplify the description, the processes of Steps S105 to S109 and the processes of Steps S110 to S115 have been described so as to be sequentially performed. However, actually, the processes are performed in parallel. That is, for example, while one sample container 8 stored in the sample rack 9 is horizontally rotated, a different sample container 8 is pulled from the sample rack 9 of the sample containers 8.

The controller 226 determines whether all the sample containers 8 stored in the sample rack 9 have been subjected to the above processes, or more precisely, whether a sample container storing section at the right end of the sample rack 9 is positioned in front of the sample container tilting mechanism 224 (Step S116). When the right end of the sample rack 9 is not yet positioned in front of the sample container tilting mechanism 224 (No in Step S116), the controller moves the sample rack 9 to the left by one pitch (Step S117) and returns the process to Step S105.

When the right end of the sample rack 9 is positioned in front of the sample container tilting mechanism 224 (Yes in Step S116), the controller 226 transmits the rack ID of the sample rack 9 and specimen IDs of all the sample containers 8 stored in the sample rack 9 to the system control apparatus 7 (Step S118). In the data transmitted in Step S118, holding positions (1 to 10) of the sample containers 8 in the sample rack 9 correspond to the specimen IDs of the held sample containers. When the specimen ID cannot be obtained due to failure to read the specimen bar-code, data indicating the reading failure of the specimen bar-code associated with the holding position is transmitted. Next, the controller 226 further moves the sample rack 9 to the left to deliver the sample rack 9 to the sample delivery unit 21b (Step S119). The controller 213 of the sample delivery unit 21b moves the received sample rack 9 (Step S120). The sample rack 9 is moved on the rack placing section 211 of the sample delivery unit 21b and then moved to the left to be transferred to the sample transport apparatus 3.

The controller 213 of the sample delivery unit 21a determines whether the conditions for completion of the analysis operation (an analysis completion instruction is issued from the user, or the sample rack 9 is not on the rack placing section 211 of the sample delivery unit 21a) are satisfied (Step S121). When the conditions are not satisfied (No in Step S121), the controller returns the process to Step S102, and when the conditions are satisfied (Yes in Step S121), the controller completes the process.

<Measuring Order Obtaining Operation of System Control Apparatus 7>

Next, an operation of the system control apparatus 7 will be described. The system control apparatus 7 obtains a measuring order of a specimen (blood sample) from the specimen ID received from the sample putting apparatus 2. Herein, the measuring order is data indicating the instruction of the analysis item for blood sample analysis, and includes attribute information of the specimen, such as the specimen ID, patient ID and name of the patient, and information of the analysis item.

FIG. 15 is a flowchart showing the procedure of a process of obtaining a measuring order. As shown in FIG. 15, when the system control apparatus 7 receives the rack ID and specimen IDs transmitted from the sample putting apparatus 2 (Step S131), an interrupt request is generated for the CPU 71*a* of the system control apparatus 7 and a process of Step S132 is invoked.

In Step S132, the CPU 71*a* transmits one of the received specimen IDs and requests a measuring order corresponding to the specimen ID from a host computer (not shown) (Step S132). The CPU 71*a* stands by to receive the measuring order (No in Step S133), and when the system control apparatus 7 receives the measuring order transmitted from the host computer (Yes in Step S133), the CPU associates the received measuring order with the rack ID and stores the measuring order in the hard disk 71*d* (Step S134). The CPU 71*a* determines whether the specimen IDs corresponding to the rack ID, that is, all the specimen IDs of all the sample containers 8 stored in the sample rack 9 having the rack ID have been subjected to a measuring order inquiry (Step S135). When there is a specimen ID yet to be subjected to a measuring order inquiry (No in Step S135), the CPU 71*a* returns the process to Step S132 and requests a measuring order corresponding to the specimen ID not yet subjected to the measuring order inquiry from the host computer.

On the other hand, when all the specimen IDs have been subjected to the measuring order inquiry (Yes in Step S135), the CPU 71*a* completes the process.

<Blood Volume Detecting Operation of System Control Apparatus 7>

In addition, the system control apparatus 7 takes an image captured by the camera 225*a* and performs image processing of the image to detect a blood volume in the sample container 8.

Figure 16:
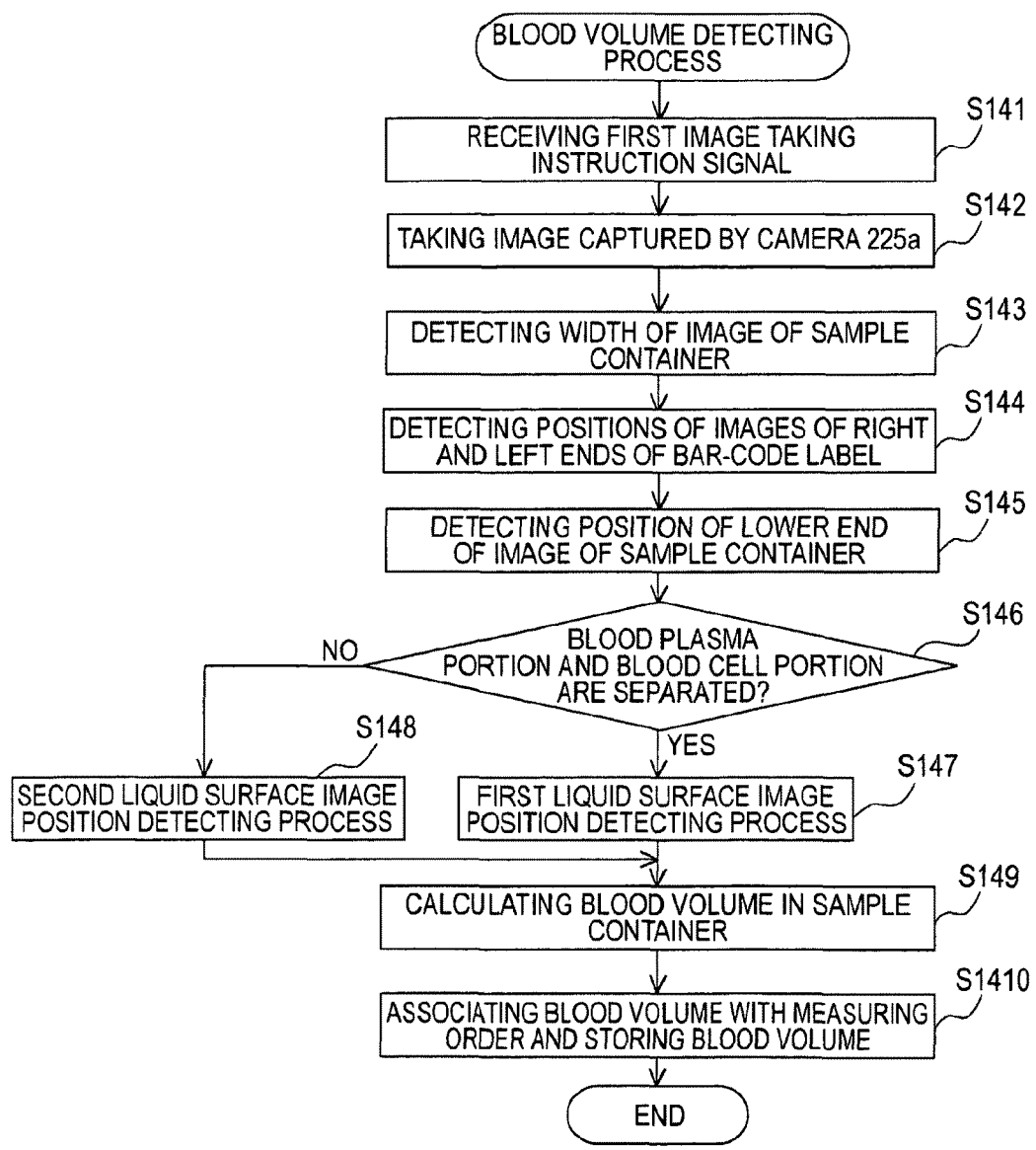
FIG. 16 is a flowchart showing the procedure of a blood volume detecting process of the system control apparatus according to the first embodiment.

FIG. 16 is a flowchart showing the procedure of a blood volume detecting process. As shown in FIG. 16, when the system control apparatus 7 receives the first image taking instruction signal transmitted from the sample putting apparatus 2 (Step S141), an interrupt request is generated for the CPU 71*a* of the system control apparatus 7 and a process of Step S142 is invoked.

Figure 17:
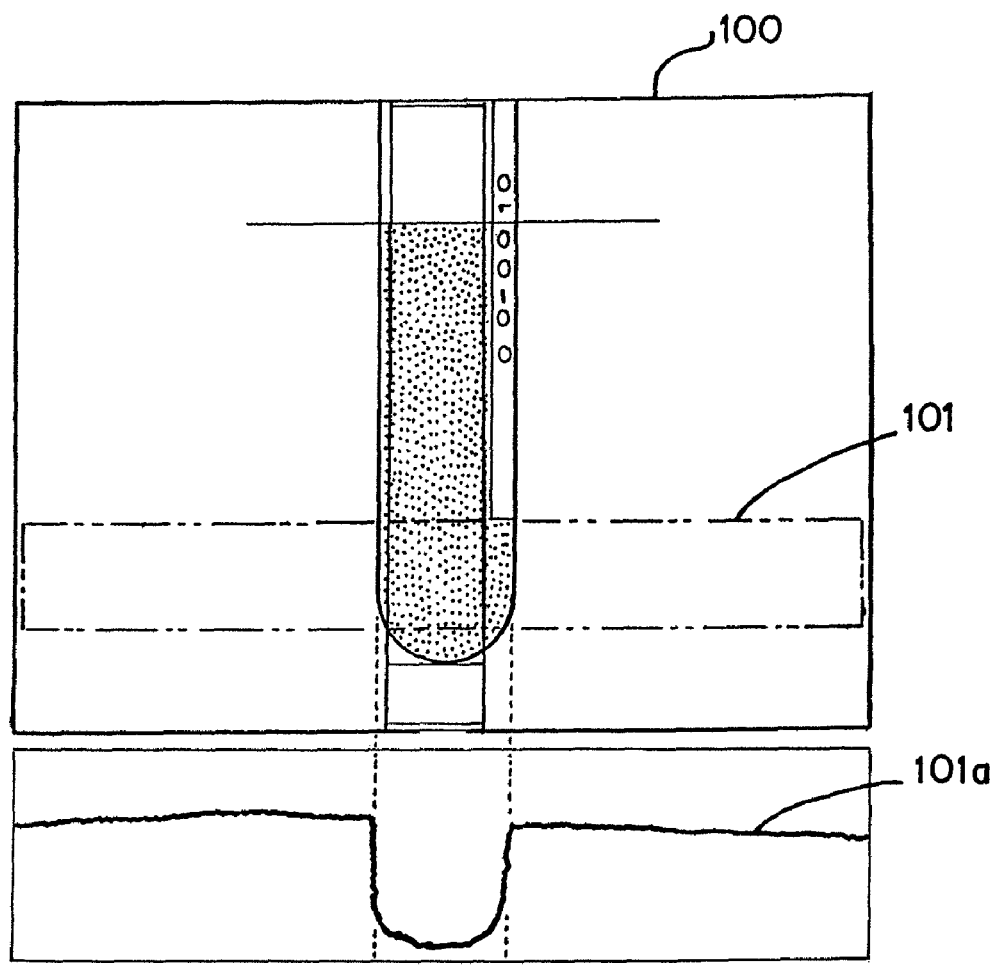
FIG. 17 is a schematic diagram for illustrating a process of detecting a width of the sample container.

In Step S142, the CPU 71*a* takes the image captured by the camera 225*a* at that time (Step S142). Next, the CPU 71*a* detects the width of an image of the sample container 8 in the taken image (Step S143). This process will be described in detail. FIG. 17 is a schematic diagram for illustrating a process of detecting the width of the image of the sample container 8. An image 100 is a color image and has luminance information of RGB of respective pixels. A processing area 101 for obtaining the width of the sample container 8 in the image 100 is subjected to the following process by the CPU 71*a*. The processing area 101 is a predetermined area, which includes an image of the vicinity of the bottom portion of the sample container 8 and does not include an image of the bar-code label. For each X coordinate in the processing area 101, the CPU 71*a* accumulates B (blue) luminance values (hereinafter, referred to as "B value") of the pixels in a Y direction in the processing area 101. That is, an accumulation value (hereinafter, referred to as "B luminance accumulation value") of the B values of the pixels in a column of pixel groups at the left end included in the processing area 101 is calculated, and the B luminance accumulation value of a column of pixel groups on the right side thereof is calculated. This operation is repeated while incrementing an X coordinate value until the right end of the processing area 101 is reached.

In FIG. 17, a graph of the B luminance accumulation value obtained as described above in the processing area 101 is denoted by reference numeral 101*a*. The B luminance accumulation value related to the processing area 101 is high in a background image and is low in the image of the sample container 8. Accordingly, the CPU 71*a* differentiates the B luminance accumulation value in an X direction and detects a portion in which the B luminance accumulation value is sharply lowered and a portion in which the B luminance accumulation value sharply increases. In this manner, the width of the sample container 8 is detected.

Figure 18:
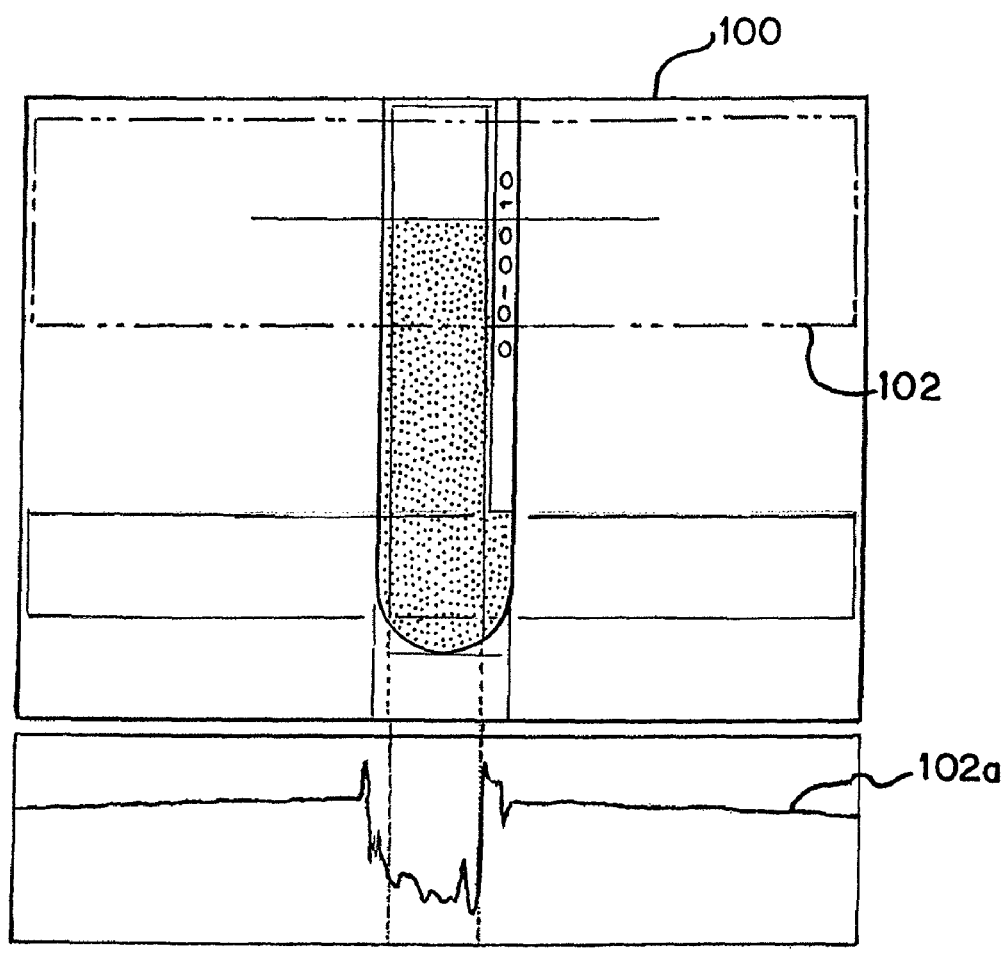
FIG. 18 is a schematic diagram for illustrating a process of detecting positions of the right and left ends of a bar-code label.

Next, the CPU 71*a* detects positions of images of the right and left ends of the bar-code label 8*b* (Step S144). This process will be described in detail. FIG. 18 is a schematic diagram for illustrating a process of detecting the positions of the right and left ends of an image of the bar-code label 8*b*. A processing area 102 for detecting the positions of the right and left ends of the image of the bar-code label 8*b* in the image 100 is subjected to the following process by the CPU 71*a*. The processing area 102 is a predetermined area, which is an upper portion in the image and includes the image of the bar-code label. For each X coordinate value in the processing area 102, the CPU 71*a* calculates a B luminance accumulation value. In the drawing, a graph of the B luminance accumulation value in the processing area 102 is denoted by reference numeral 102*a*. As shown by the graph 102*a*, the B luminance accumulation value related to the image of the bar-code label is higher than the B luminance accumulation value related to the background image and the image of the sample container. Accordingly, the CPU 71*a* scans the B luminance accumulation value from left to right and detects as the position of the image of the left end of the bar-code label a position where the B luminance accumulation value becomes high and is then sharply lowered. Then, the CPU scans the B luminance accumulation value from the right to the left and detects as the position of the image of the right end of the bar-code label a position where the B luminance accumulation value becomes high and is then sharply lowered.

Figure 19:
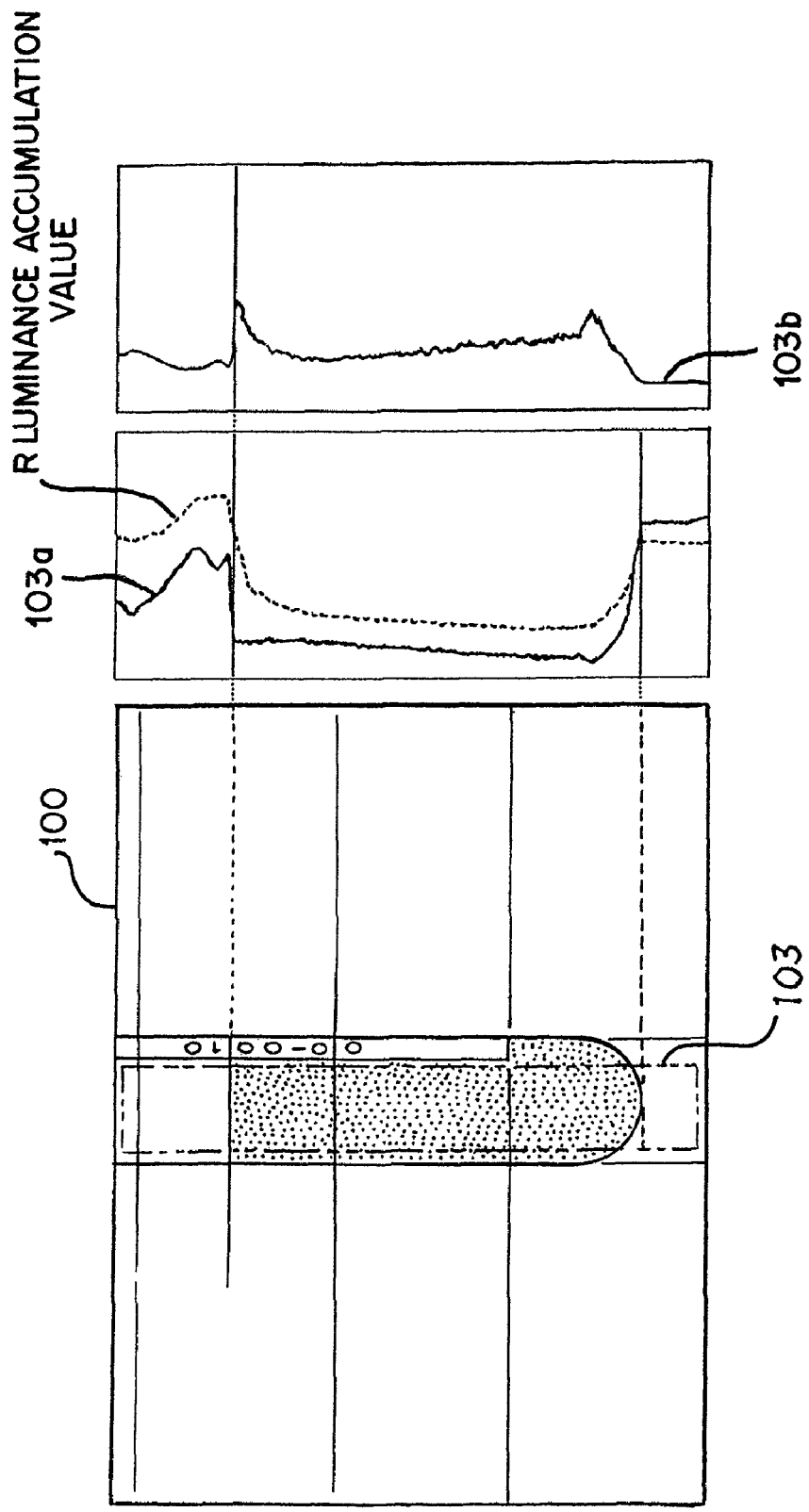
FIG. 19 is a schematic diagram for illustrating a process of detecting a position of the lower end of the sample container.

Next, the CPU 71*a* detects a position of the lower end of the image of the sample container (Step S145). This process will be described in detail. FIG. 19 is a schematic diagram for illustrating a process of detecting the position of the lower end of the image of the sample container. First, the CPU 71*a* determines a processing area 103 for detecting the position of the lower end of the image of the sample container and the position of an image of a liquid surface of the blood sample in the image 100. The processing area 103 is an area at the slightly inner side of an area surrounded by the positions of the images of the right and left ends of the bar-code label detected in Step S144. This is because the image of the bar-code label does not exist in the area between the image of the left end and the image of the right end of the bar-code label.

For each Y coordinate value in the processing area 103, the CPU 71*a* calculates a B luminance accumulation value by accumulating B values in an X direction, and calculates an R luminance accumulation value by accumulating R values. In addition, for each Y coordinate, the CPU 71*a* calculates a value (hereinafter, referred to as "R/B accumulation luminance ratio") which is obtained by dividing the R luminance accumulation value by the B luminance accumulation value. In the drawing, a graph of the B luminance accumulation value in the processing area 103 is denoted by reference numeral 103*a* and a graph of R/B in the processing area 103 is denoted by reference numeral 103*b*. As shown by the graph 103*a*, the B luminance accumulation value of the image of the blood sample in the sample container is lower than the B luminance accumulation values of the background image and an image of a portion in which the blood sample in the sample container does not exist. Moreover, in the image of the blood sample, the R/B accumulation luminance ratio is higher than in the other portion. Accordingly, the CPU 71*a* differentiates the B luminance accumulation value in a Y direction, and detects as the position of the lower end of the image of the sample container a position where the B luminance accumulation value is sharply lowered in a direction toward the upper side from the lower end of the processing area 103.

Next, the CPU 71*a* determines whether a blood plasma portion and a blood cell portion are separated in the blood sample (Step S146). In this process, it is determined that the blood plasma portion and the blood cell portion are separated, when the B luminance accumulation value and the R luminance accumulation value of the processing area 103 are scanned from the position of the lower end of the image of the sample container to the upper side and only the R luminance accumulation value is large.

When the blood plasma portion and the blood cell portion are separated (Yes in Step S146), the CPU 71*a* performs a first liquid surface image position detecting process of detecting the position of the image of the liquid surface of the blood sample (Step S147). When the blood plasma portion and the blood cell portion are not separated (No in Step S146), the CPU performs a second liquid surface image position detecting process of detecting the position of the image of the liquid surface of the blood sample (Step S148). In the first liquid surface image position detecting process, a position, where the B luminance accumulation value becomes large sharply in a direction toward the upper side from the lower end of the image of the sample container and the R/B accumulation luminance ratio is equal to or less than a predetermined value, is detected as the position of the image of the liquid surface. In the second liquid surface image position detecting process, a position, where the B luminance accumulation value becomes large sharply in a direction toward the upper side from the lower end of the image of the sample container, is detected as the position of the image of the liquid surface.

Next, the CPU 71*a* calculates the blood volume in the sample container 8 (Step S149). In this process, the CPU 71*a* calculates a blood volume BV by the following expressions (1) and (2).

$$R=(k \cdot W-2T)/2 \qquad (1)$$

$$BV=\pi R^2 \times (k \cdot H-R)+2\pi R^3/3 \qquad (2)$$

R denotes a radius of an inner face of a sample container, k denotes a coefficient determined by scale of a captured image, W denotes a width of an image of a sample container, T denotes a thickness of a sample container and H denotes a height (the difference between a position of an image of a liquid surface and a position of an image of the lower end of a sample container) of an image of a blood sample.

When calculating the blood volume BV, the CPU 71*a* associates the blood volume with the measuring order having the specimen ID of the blood sample as a target of imaging process, stores the blood volume in the hard disk 71*d* (Step S1410), and then completes the process.

<Blood Coagulation Determining Operation of System Control Apparatus 7>

The system control apparatus 7 takes an image captured by the camera 225*b* and performs image processing of the image to determine whether the blood sample in the sample container 8 is coagulated.

Figure 20:
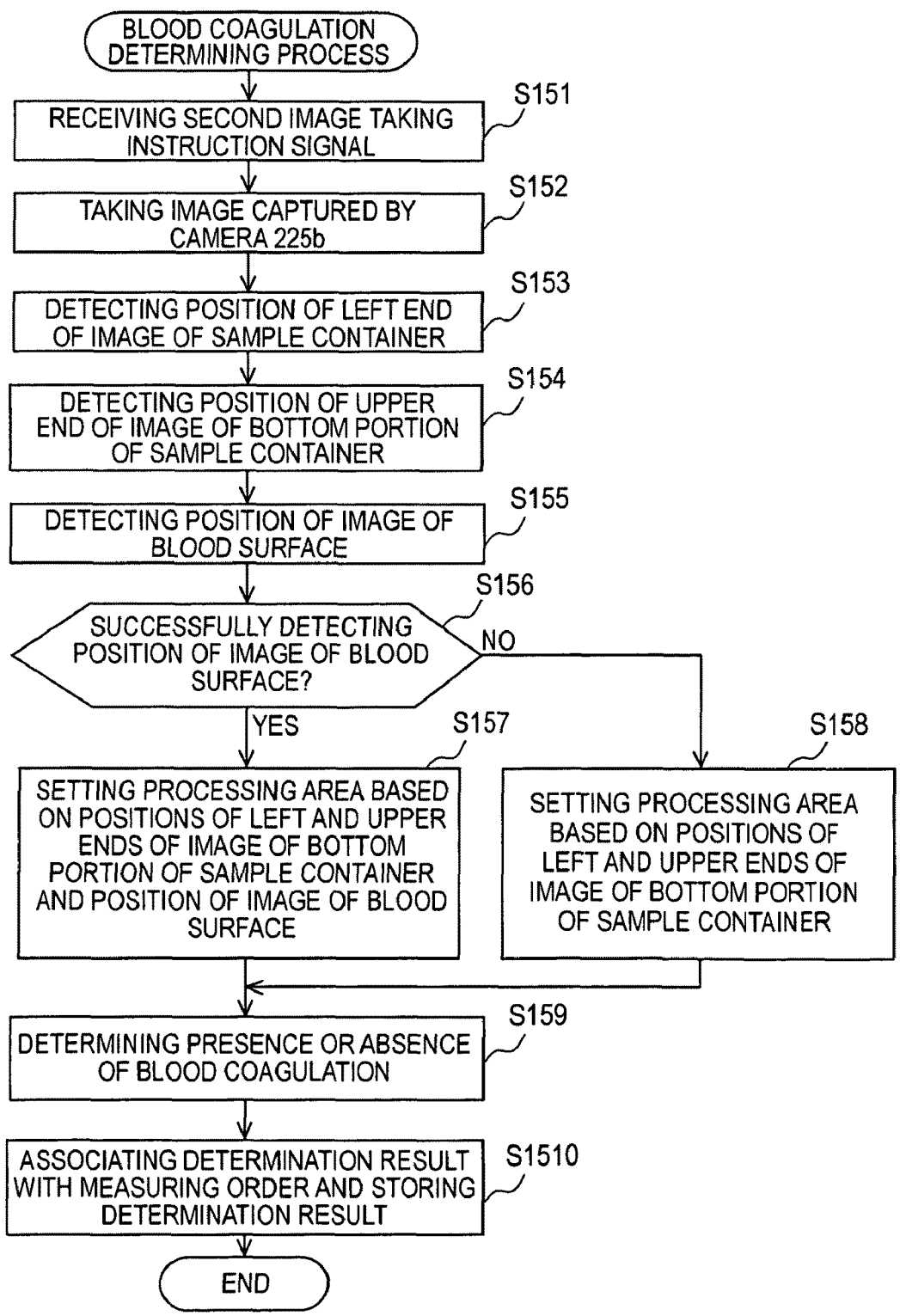
FIG. 20 is a flowchart showing the procedure of a blood coagulation determining process of the system control apparatus according to the first embodiment.

FIG. 20 is a flowchart showing the procedure of a blood coagulation determining process. As shown in FIG. 20, when the system control apparatus 7 receives the second image taking instruction signal transmitted from the sample putting apparatus 2 (Step S151), an interrupt request is generated for the CPU 71*a* of the system control apparatus 7 and a process of Step S152 is invoked.

Figure 21:
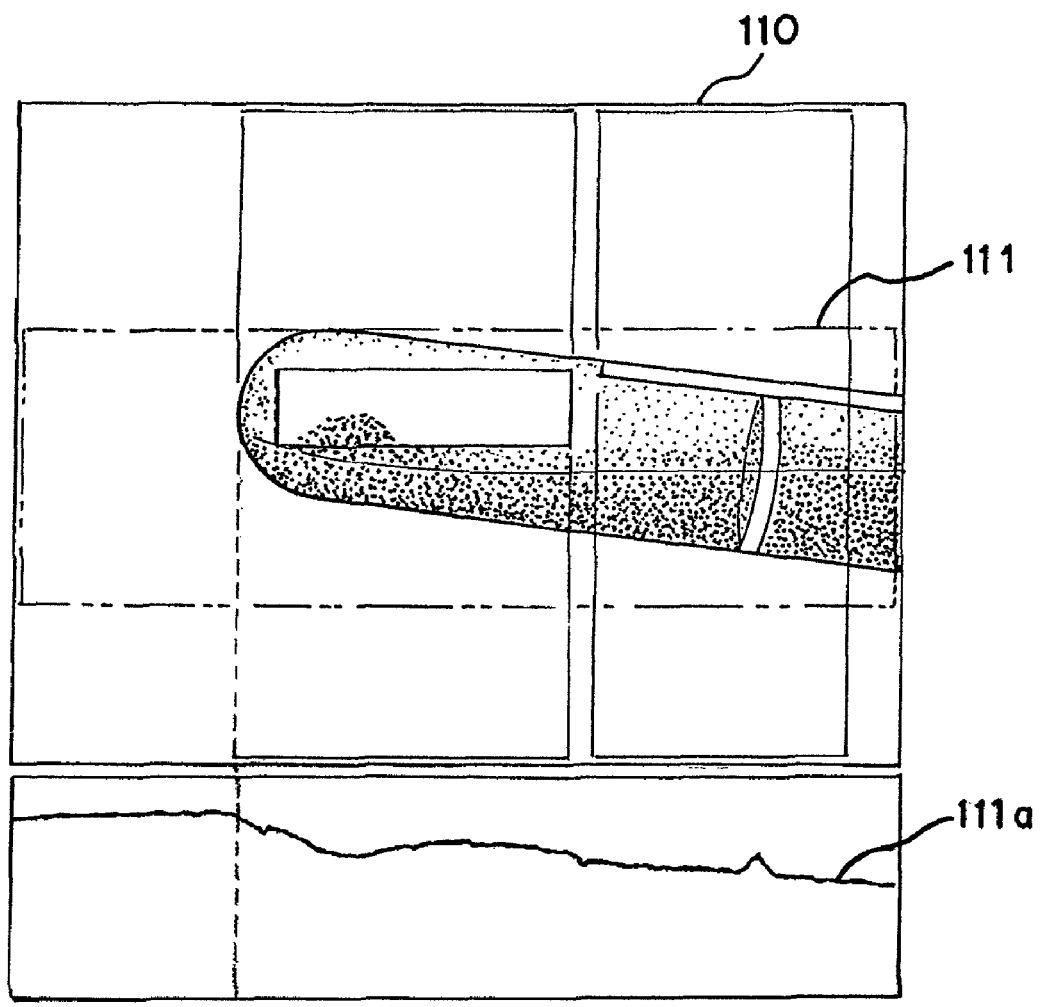
FIG. 21 is a schematic diagram for illustrating a process of detecting a position of the left end of the sample container.

In Step S152, the CPU 71*a* takes the image captured by the camera 225*b* at that time (Step S152). Next, the CPU 71*a* detects the position of the left end of an image of the sample container 8 in the taken image (Step S153). This process will be described in detail. FIG. 21 is a schematic diagram for illustrating a process of detecting the position of the left end of the image of the sample container 8. An image 110 is a color image and has luminance information of RGB of respective pixels. A processing area 111 for obtaining the position of the left end of the image of the sample container 8 in the image 110 is subjected to the following process by the CPU 71*a*. The processing area 111 is a predetermined area, which includes an image of the vicinity of the bottom portion of the sample container 8. For each X coordinate, the CPU 71*a* calculates a B luminance accumulation value in a Y direction in the processing area 111. In the drawing, a graph of the B luminance accumulation value in the processing area 111 is denoted by reference numeral 111*a*. As shown by the graph 111*a*, the B luminance accumulation value related to the image of the sample container is lower than the B luminance accumulation value related to a background image. Accordingly, the CPU 71*a* differentiates the B luminance accumulation value in an X direction and detects as the position of the left end of the image of the sample container a position where the B luminance accumulation value scanned from left to right is lowered.

Figure 22:
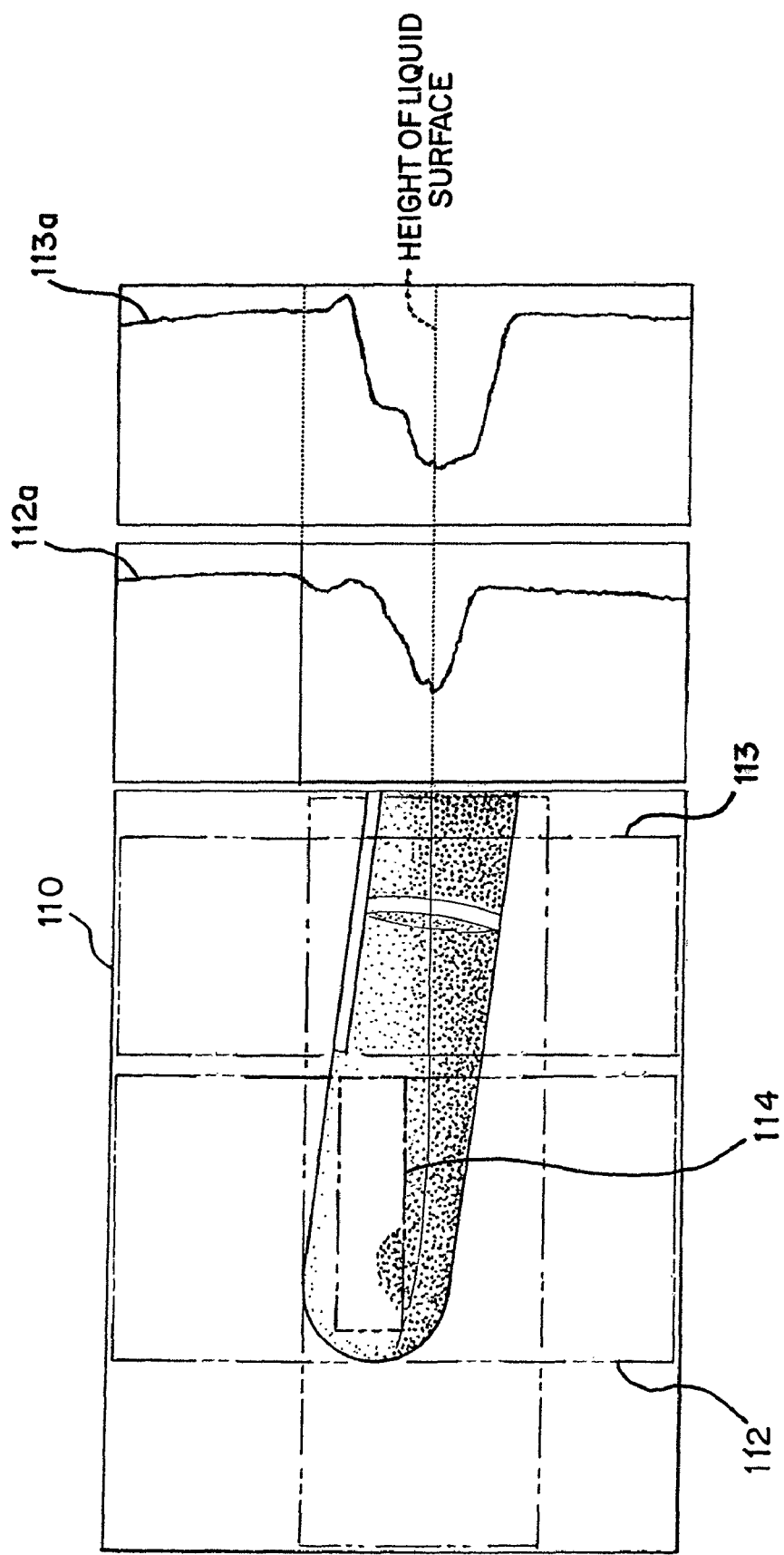
FIG. 22 is a schematic diagram for illustrating a process of detecting a position of the upper end of a bottom portion of the sample container.

Next, the CPU 71*a* detects the position of the upper end of the image of the bottom portion of the sample container (Step S154). This process will be described in detail. FIG. 22 is a schematic diagram for illustrating a process of detecting the position of the upper end of the image of the bottom portion of the sample container. The CPU 71*a* determines a processing area 112 for detecting the position of the upper end of the image of the bottom portion of the sample container in the image 110. The processing area 112 is an area from the position of the left end of the image of the sample container detected in Step S153 to a position positioned on the right side thereof by a predetermined number of pixels. This is because, since the sample container 8 is imaged in a state in which the bottom portion of the sample container 8 is positioned higher than the cap section 8*a* in the image, and it is required that the image of the bottom portion of the sample container is included in the processing area so that the bottom portion of the sample container 8 becomes the upper end of the sample container, the image of the bottom portion of the sample container 8 exists in an area on the right side of the position of the left end.

For each Y coordinate, the CPU 71*a* calculates a B luminance accumulation value in the X direction in the processing area 112. In the drawing, a graph of the B luminance accumulation value in the processing area 112 is denoted by reference numeral 112*a*. As shown by the graph 112*a*, the B luminance accumulation value related to the image of the sample container is lower than the B luminance accumulation value related to the background image. Accordingly, the CPU 71*a* differentiates the B luminance accumulation value in the Y direction, and detects as the position of the upper end of the image of the bottom portion of the sample container a position where the B luminance accumulation value is lowered when the B luminance accumulation value is scanned from the upper side to the lower side.

Next, the CPU 71*a* detects the position of the image of the liquid surface of the blood sample (Step S155). This process will be described in detail. The CPU 71*a* subjects a processing area 113 (see FIG. 22 for reference) for detecting the position of the image of the liquid surface of the blood sample in the image 110 to the following process. The processing area 113 is a predetermined area, which is positioned on the right side in the image 110. When the blood sample contains a clot formed by the aggregation of blood, the clot usually sinks to the bottom portion of the sample container 8 due to the weight thereof. Accordingly, when the sample container 8 is tilted to the second imaging position where the bottom portion of the sample container 8 is positioned on the left side in a front view, the blood sample in the sample container 8 moves toward the cap section 8a (right side) of the sample container 8 and the blood sample in the bottom portion of the sample container 8 decreases. The clot sinking to the bottom of the sample container 8 moves along the inner face of the bottom portion of the sample container 8 and protrudes from the liquid surface of the shallow blood sample. Thus, only the liquid blood exists in the area on the right side in the image 110. The processing area 113 is provided in this portion and thus the processing area 113 includes an image of the liquid blood without an image of the clot. Accordingly, the processing area 113 is suitable for detection of the liquid surface image, which is an image of a surface of liquid. For each Y coordinate value in the processing area 113, the CPU 71a calculates a B luminance accumulation value and an R luminance accumulation value. In the drawing, a graph of the B luminance accumulation value in the processing area 113 is denoted by reference numeral 113a. First, the CPU 71a sequentially checks an R/B accumulation luminance ratio toward the upper side from the lower end of the processing area 113 and determines whether the R/B accumulation luminance ratio is equal to or greater than a predetermined value. Herein, the R/B accumulation luminance ratio is large in the blood image. Accordingly, when the R/B accumulation luminance ratio is equal to or greater than the predetermined value, it can be determined that the blood is in the sample container. When it cannot be determined that the blood is not in the sample container, that is, when the R/B accumulation luminance ratio does not exceed the predetermined value in a direction of a Y axis of the entire processing area 113, it is regarded that detection of the position of the image of the liquid surface of the blood sample failed.

When it can be determined that the blood exists, the CPU 71a checks the B luminance accumulation value toward the upper side from a position (the R/B accumulation luminance ratio is equal to or greater than the predetermined value) where it is considered that the blood exists to detect a position, where a differential value of the B luminance accumulation value is equal to or greater than a predetermined value and the R/B accumulation luminance ratio is equal to or less than a predetermined value, as the position of the image of the blood surface. When there is not such a position, it is regarded that detection of the position of the image of the blood surface failed.

Next, the CPU 71a determines whether the detection of the position of the image of the blood surface in Step S155 succeeded (Step S156). When the detection of the position of the image of the blood surface succeeded (Yes in Step S156), a processing area for determining the presence or absence of blood coagulation is set based on the positions of the left and upper ends of the image of the bottom portion of the sample container and the position of the image of the blood surface (Step S157). This processing area will be described with reference to FIG. 22. In the process of Step S157, a processing area 114, which is positioned on the right side of the left end of the image of the bottom portion of the sample container, on the lower side of the upper end of the image of the bottom portion of the sample container, and on the upper side of the image of the blood surface, is set. As shown in FIG. 22, when the blood is coagulated, the clot protrudes upward from the liquid surface in some cases. In this case, the image of the clot is in the processing area 114 positioned on the upper side of the image of the liquid surface. The processing area 114 is subjected to image processing and thus the coagulation of the blood can be detected.

Figure 23:
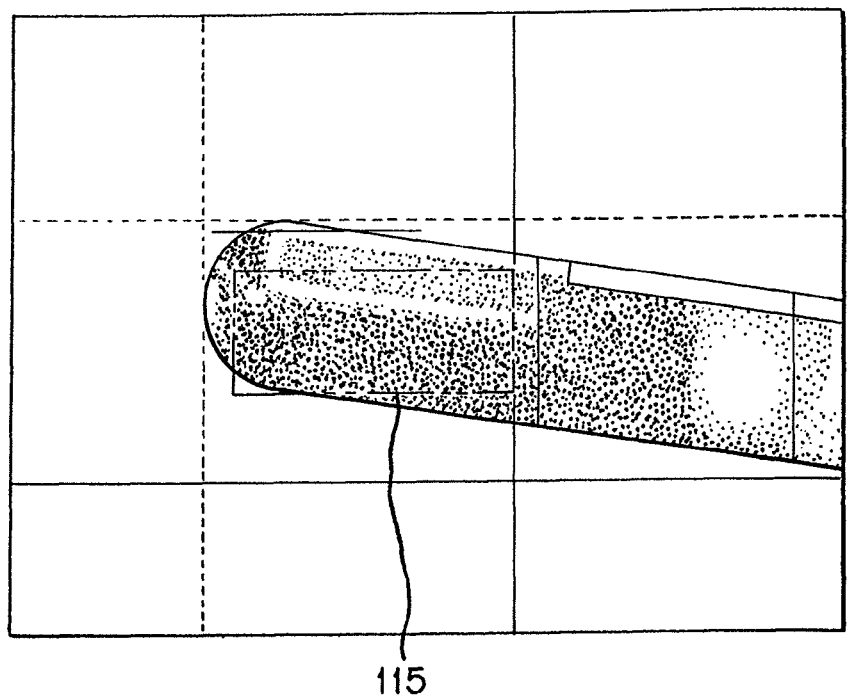
FIG. 23 is a schematic diagram for illustrating a processing area for determining blood coagulation when detection of a position of a blood surface fails.

On the other hand, when the detection of the position of the image of the blood surface fails (No in Step S156), a processing area for determining the presence or absence of blood coagulation is set based on the positions of the left and upper ends of the image of the bottom portion of the sample container (Step S158). FIG. 23 is a schematic diagram for illustrating a processing area for determining blood coagulation when the detection of the position of the image of the blood surface fails. As shown in FIG. 23, a processing area 115 having a predetermined size is positioned on the right side of the left end of the image of the bottom portion of the sample container and on the lower side of the upper end of the image of the bottom portion of the sample container in this case. When it can be determined that the blood exists and the position of the image of the blood surface cannot be detected, the blood has viscosity due to coagulation and adheres to the inner face of the sample container in some cases. In this case, the liquid surface cannot be confirmed even if the sample container 8 is tilted, and the blood image occupies a large portion of the processing area 115. The processing area 115 is subjected to image processing and thus the coagulation of the blood can be detected.

After setting the processing area for detecting blood coagulation, the CPU 71a determines the presence or absence of blood coagulation (Steps S159). This process will be described as follows. For each pixel included in the processing area 114 and the processing area 115, the CPU 71a calculates an R/B luminance ratio which is a ratio of an R value to a B value of a single pixel. In addition, the CPU 71a counts the number of pixels, each of which has the B value equal to or less than a predetermined value and the R/B luminance ratio equal to or less than a predetermined value, among all the pixels included in the processing area 114 or 115. When the number of pixels is equal to or greater than a predetermined value, it is determined that the blood is coagulated. When the number of pixels is less than the predetermined value, it is determined that the blood is not coagulated.

Figure 24A:
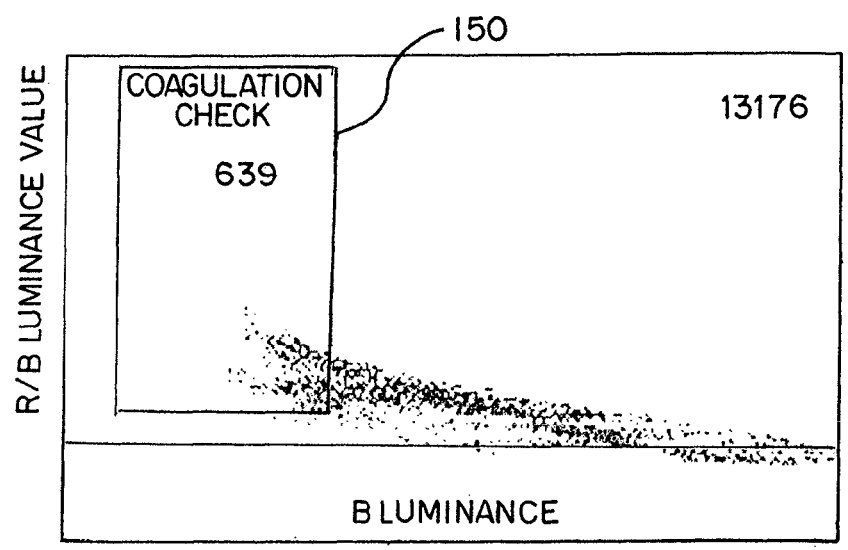
FIG. 24A is a scattergram showing a distribution state related to B values and R/B luminance ratios of pixels in the processing area in the image shown in FIG. 22.
Figure 24B:
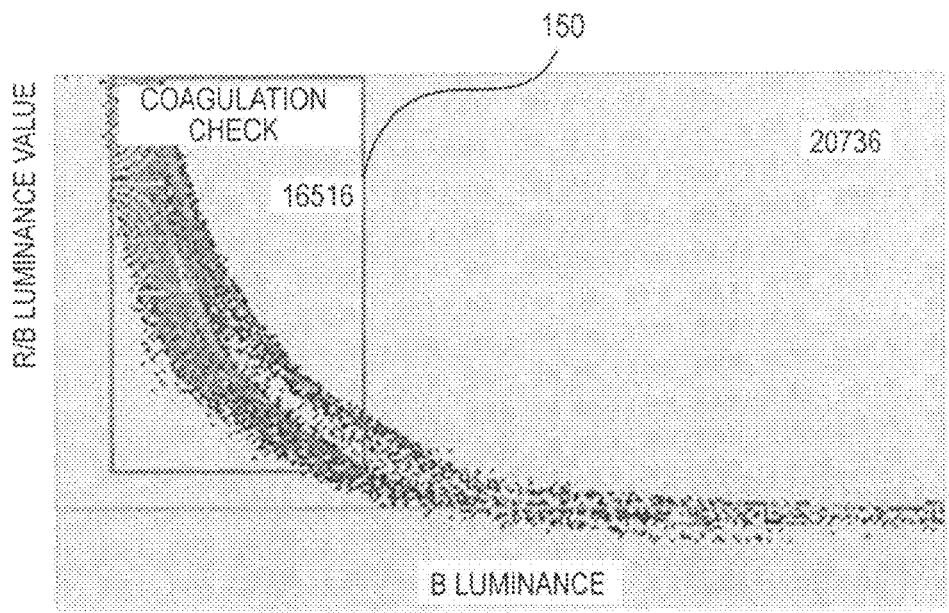
FIG. 24B is a scattergram showing a distribution state related to B values and R/B luminance ratios of pixels in the processing area in the image shown in FIG. 23.
Figure 24C:
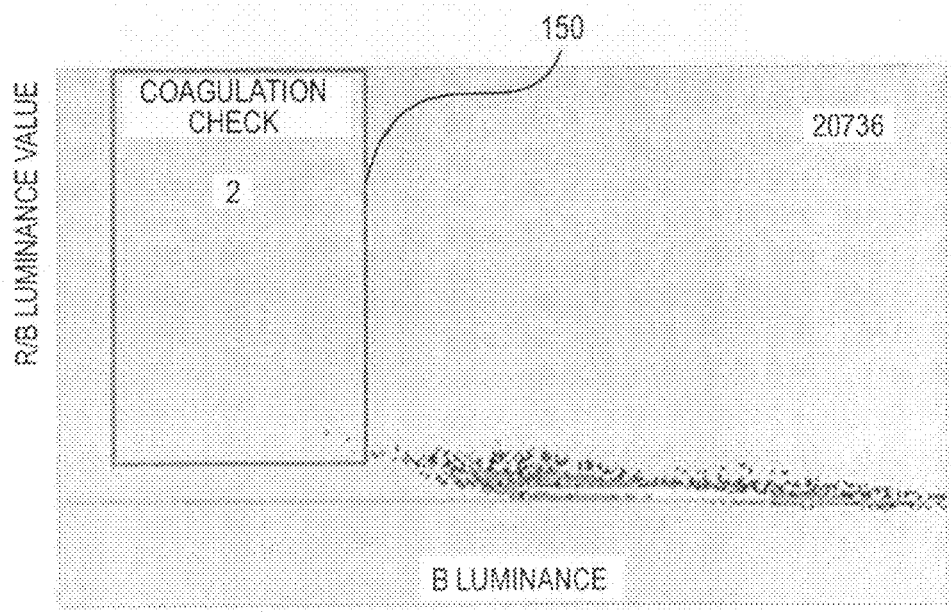
FIG. 24C is a scattergram showing a distribution state related to B values and R/B luminance ratios of pixels in the processing area for blood which is not coagulated.

FIG. 24A is a scattergram showing a distribution state related to the B values and the R/B luminance ratios of the pixels in the processing area 114 in the image shown in FIG. 22, FIG. 24B is a scattergram showing a distribution state related to the B values and the R/B luminance ratios of the pixels in the processing area 115 in the image shown in FIG. 23, and FIG. 24C is a scattergram showing a distribution state related to the B values and the R/B luminance ratios of the pixels in the processing area 114 for the blood which is not coagulated. In these drawings, a range satisfying the condition that the B value is equal to or less than a predetermined value and the R/B luminance ratio is equal to or less than a predetermined value is represented by a rectangular frame 150. As shown in FIG. 24A, when a clot protrudes on a blood surface, a large number of pixels (several hundred pixels or more when the image 100 has a size of 640×480 dots) in all the pixels included in the processing area 114 satisfy the above condition. In addition, as shown in FIG. 24B, when it can be determined that blood exists and the position of an image of a blood surface cannot be detected, a very large number of pixels (10,000 pixels or more when the image 100 has a size of 640×480 dots) in all the pixels included in the processing area 115 satisfy the above condition. On the other hand, as shown in FIG. 24C, when a clot protrudes on a blood surface, only a very small number of pixels (several pixels when the image 100 has a size of 640×480 dots) in all the pixels included in the processing area 114 satisfy the above condition. When a size of an image is 640×480 dots, the above threshold is set to about 100 and thus blood coagulation can be detected with high accuracy.

When determining the presence or absence of blood coagulation, the CPU 71a associates a determination result with the measuring order having the specimen ID of the blood sample as a target of image processing and stores the result in the hard disk 71d (Step S1510), and then completes the process.

<Measuring Order Transmitting Operation of System Control Apparatus 7>

As will be described later, the sample transport apparatus 3 transmits a rack ID to the system control apparatus 7 to request a measuring order corresponding to the rack ID. The system control apparatus 7 transmits the measuring order to the sample transport apparatus 3 in accordance with the request.

Figure 25:
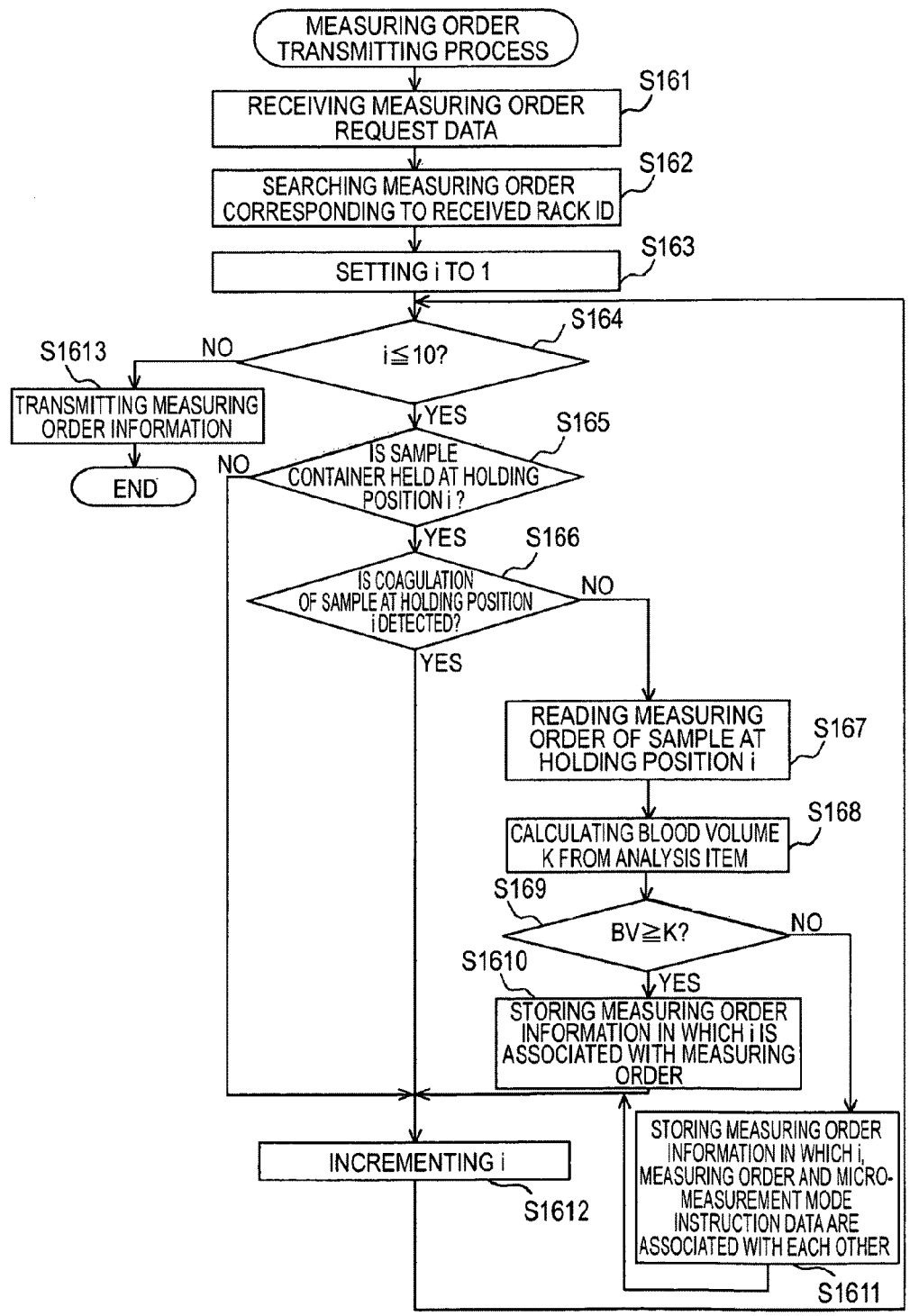
FIG. 25 is a flowchart showing the procedure of a measuring order transmitting process of the system control apparatus according to the first embodiment.

FIG. 25 is a flowchart showing the procedure of a measuring order transmitting process. As shown in FIG. 25, when the request data of the measuring order including the rack ID transmitted from the sample transport apparatus 3 is received by the system control apparatus 7 (Step S161), an interrupt request is generated for the CPU 71a of the system control apparatus 7 and a process of Step S162 is invoked.

In Step S162, the CPU 71a searches the measuring order corresponding to the received rack ID from the hard disk 71d. Next, the CPU 71a sets a variable i indicating a holding position of the sample rack to 1 (Step S163) and determines whether i is equal to or less than 10 (Step S164). When i is equal to or less than 10 (Yes in Step S164), the CPU 71a determines whether the sample container is held at a holding position i (whether there is the measuring order corresponding to the holding position i) (Step S165). When the sample container is not held at the holding position i (No in Step S165), the CPU 71a performs a process of Step S1612.

When the sample container is held at the holding position i (Yes in Step S165), it is determined whether blood coagulation is detected in the sample at the holding position i (Step S166). When the blood coagulation is detected (Yes in Step S166), the CPU 71a performs a process of Step S1612.

On the other hand, when the blood coagulation is not detected in the sample at the holding position i (No in Step S166), the CPU 71a reads the measuring order of the blood sample at the holding position i from the hard disk 71d (Step S167). The CPU 71a determines a blood volume K necessary for analysis from an analysis item included in the measuring order (Step S168) and compares a blood volume BV detected in the blood sample at the holding position i with the necessary blood volume K to determine whether the expression BV≧K is satisfied (Step S169). When the expression BV≧K is satisfied (Yes in Step S169), the CPU 71a stores measuring order information in which the holding position i is associated with the measuring order in the RAM 71c (Step S1610) and performs a process of Step S1612.

On the other hand, when BV is less than K (No in Step S169), the CPU 71a stores measuring order information in which the holding position i, the measuring order and information instructing the micro-measurement mode are associated with each other in the RAM 71c (Step S1611) and performs a process of Step S1612. In Step S1612, the CPU 71a increments i by 1 and returns the process to Step S164. In Step S164, when i is not equal to or less than 10 (No in Step S164), the CPU 71a transmits the measuring order information stored in the RAM 71c to the sample transport apparatus 3 of a measuring order request source (Step S1613) and completes the process.

<Operation of Sample Transport Apparatus 3>

Figure 26:
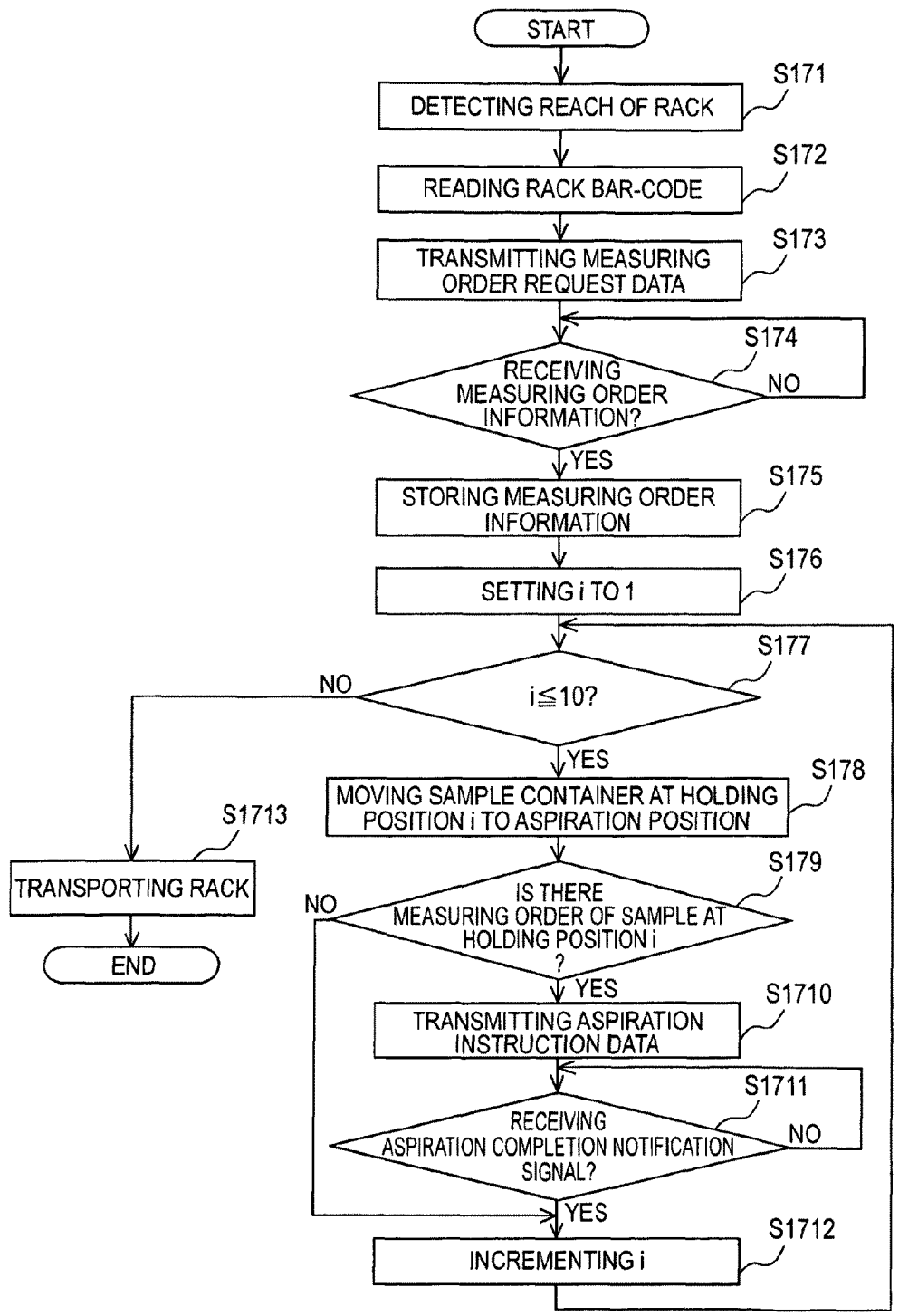
FIG. 26 is a flowchart showing the flow of an operation of a sample transport apparatus according to the first embodiment.

Herein, an operation of the sample transport apparatus 3 disposed in front of the blood cell analyzing apparatus 5 will be described. FIG. 26 is a flowchart showing the flow of the operation of the sample transport apparatus 3. When the sample rack 9 is transported to the rack slider 32 of the sample transport apparatus 3 from the upstream side of transport, a sensor (not shown) detects the arrival of the sample rack 9. When a detection signal of the sample rack 9 is provided to the controller 31c from the sensor (Step S171), an interrupt request is generated for the CPU of the controller 31c and a process of Step S172 is invoked.

In Step S172, the controller 31c reads the rack bar-code of the sample rack 9 by a bar-code reader (not shown) to obtain a rack ID. The controller 31c transmits measuring order request data including the rack ID to the system control apparatus 7 (Step S173). Next, the controller 31c stands by to receive the measuring order information from the system control apparatus 7 (No in Step S174).

When the measuring order information is received by the sample transport apparatus 3 (Yes in Step S174), the controller 31c stores the received measuring order information in the memory of the sample transport apparatus 3 (Step S175). FIG. 27 is a schematic diagram showing the data structure of the measuring order information. The data stored in the memory of the sample transport apparatus 3 by the process of Step S175 is configured by a rack ID 160 and measuring order information 161a to 161j about the blood samples held in the sample rack 9. The measuring order information 161a to 161j includes holding position information, a measuring order and micro-measurement mode instruction data. The measuring order includes a specimen ID and analysis item data.

After storing the measuring order information in the memory, the controller 31c sets a variable i indicating the holding position of the sample rack to 1 (Step S176) and determines whether i is equal to or less than 10 (Step S177). When i is equal to or less than 10 (Yes in Step S177), the controller 31c moves the sample container 8 at the holding position i to an aspiration position, where the blood cell analyzing apparatus 5 aspirates the sample, by the measuring line 31a (Step S178) and determines whether there is measuring order information about the sample at the holding position i in the measuring order information in the memory (Step S179). When there is no measuring order information (No in Step S179), the controller 31c performs a process of Step S1712.

On the other hand, when there is measuring order information about the sample at the holding position i (Yes in Step S179), the controller 31c transmits aspiration instruction data including the analysis item data and the specimen ID included in the measuring order information to the blood cell analyzing apparatus 5 (Step S1710). When micro-measurement mode instruction data is included in the measuring order information, the micro-measurement mode instruction data is included in the aspiration instruction data.

The controller 31c stands by to receive an aspiration completion notification signal from the blood cell analyzing apparatus 5 (No in Step S1711). When the aspiration completion notification signal is received from the blood cell analyzing apparatus 5 (Yes in Step S1711), the controller 31c performs a process of Step S1712.

In Step S1712, the controller 31c increments i by 1 and returns the process to Step S177. In Step S177, when i is not equal to or less than 10 (No in Step S177), the controller 31c conveys the sample rack 9 to the apparatus on the downstream side of transport (Step S1713) and completes the process.

As described above, regarding a blood sample, which is determined to have coagulated and for which measuring order information is not generated, the sample container 8 containing the blood sample is stopped at an aspiration position, and is then transported from the aspiration position without issuing aspiration instruction data. Regarding a blood sample, which is determined not to have coagulated and for which measuring order information is generated, the sample container 8 is stopped at the aspiration position, and then aspiration instruction data is issued. This blood sample is aspirated by the measuring unit 51 as described later, and an aspiration completion notification signal is then issued and the blood sample is transported from the aspiration position. Aspiration of the blood sample requires a predetermined time (for example, two seconds) and the predetermined time is longer than the time (for example, one second) when the sample container of the blood sample which is determined to have coagulated is stopped at the aspiration position. In this manner, by moving the blood sample, which does not require aspiration, from the aspiration position in a short time, a large number of blood samples cam be efficiently analyzed.

<Operation of Blood Cell Analyzing Apparatus 5>

Figure 28:
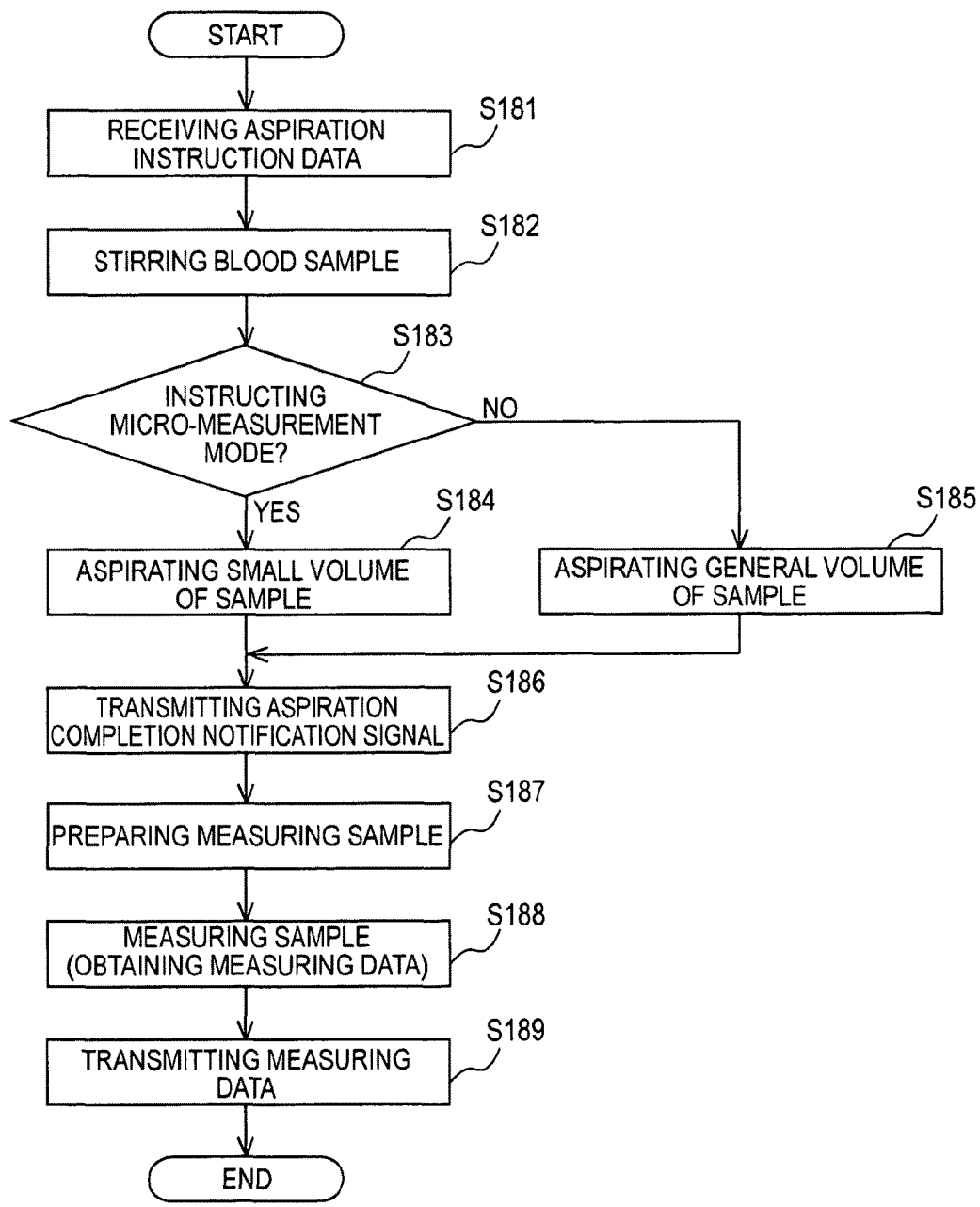
FIG. 28 is a flowchart showing the flow of an operation of the measuring unit of a blood cell analyzing apparatus according to the first embodiment.

Next, an operation of the blood cell analyzing apparatus 5 will be described. FIG. 28 is a flowchart showing the flow of an operation of the measuring unit 51 of the blood cell analyzing apparatus 5. When aspiration instruction data is received from the sample transport apparatus 3 to the measuring unit 51 (Step S181), an interrupt request is generated for the CPU of the controller 515 of the measuring unit 51 and a process of Step S182 is invoked.

In Step S182, the controller 515 stirs a blood sample in the sample container. Then, the controller 515 determines whether the aspiration instruction data includes micro-measurement mode instruction data (Step S183). When the micro-measurement mode instruction data is included (Yes in Step S183), the sample dispensing section 511 aspirates a smaller volume of the blood sample than in the normal-measurement mode (Step S184). When the micro-measurement mode instruction data is not included (No in Step S183), the controller 515 causes the sample dispensing section 511 to aspirate a general volume of the blood sample (Step S185). Next, the controller 515 transmits an aspiration completion notification signal to the sample transport apparatus 3 (Step S186).

Next, the controller 515 causes the measuring sample preparing section 512 to mix the aspirated blood sample with a reagent and a diluent and prepare a measuring sample (Step S187) and then supplies the prepared measuring sample to the optical detecting section 513 to obtain measuring data including parameters such as peaks and pulse widths of a side-scattered light signal, a forward-scattered light signal and a fluorescent signal (Step S188). The controller 515 transmits the measuring data to the information processing unit 52 (Step S189) and completes the process.

The information processing unit 52 analyzes the received measuring data to classify blood cells included in the blood sample and count the number of blood cells for every type of blood cell. Furthermore, the information processing unit 52 creates a scattergram or a histogram and stores the analysis result data including the specimen ID and these analysis results in the hard disk 521$d$. The image display section 522 displays an analysis result screen showing the analysis results. The analysis result data is transmitted from the information processing unit 52 to the host computer and stored by the host computer.

<Operation of Sample Storing Apparatus 4>

The sample rack 9 delivered from the sample transport apparatus 3 on the downmost-stream side of transport is fed to the sample storing apparatus 4. The sample storing apparatus 4 transports the sample rack on the rack placing section and stores the sample rack.

Second Embodiment

[Configuration of Blood Sample Analyzing Apparatus]

Figure 29:
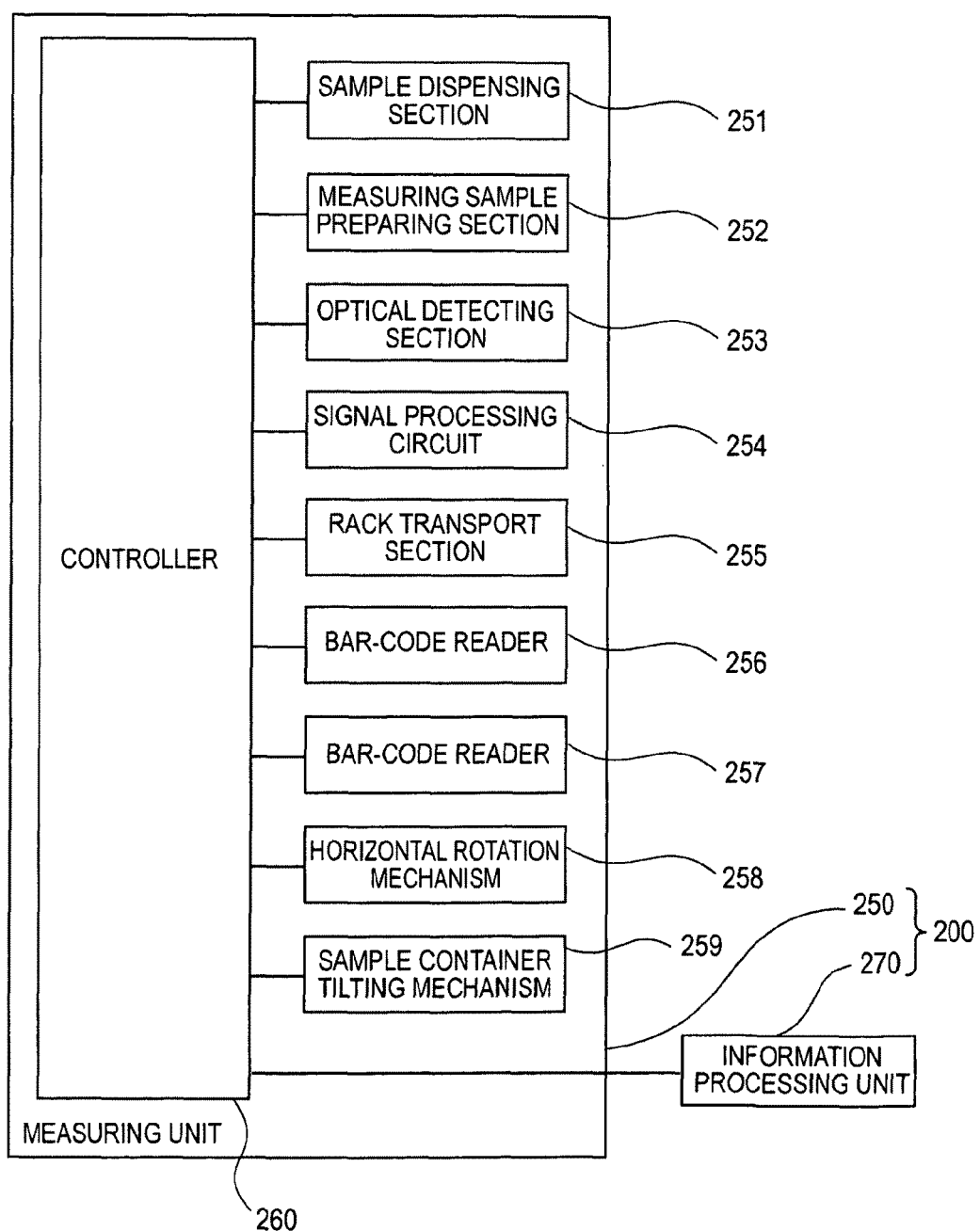
FIG. 29 is a block diagram showing the configuration of a blood sample analyzing apparatus according to a second embodiment.

FIG. 29 is a block diagram showing the configuration of a blood sample analyzing apparatus 200 according to this embodiment. The blood sample analyzing apparatus 200 as an optical flow cytometry type multiple blood cell analyzing apparatus obtains fluorescent intensity, side-scattered light intensity and the like of blood cells included in a blood sample, classifies the blood cells included in the sample on the basis of the above fluorescent intensity, side-scattered light intensity and the like, and counts the number of blood cells for every type. Moreover, the blood sample analyzing apparatus 200 creates and displays a scattergram in which the classified blood cells are color-coded for every type. The blood sample analyzing apparatus 200 includes a measuring unit 250 for measuring a blood sample and an information processing unit 270 for processing measuring data output from the measuring unit 250 and displaying an analysis result of the blood sample.

As shown in FIG. 29, the measuring unit 250 includes a sample dispensing section 251, a measuring sample preparing section 252, an optical detecting section 253, a signal processing circuit 254, a rack transport section 255, bar-code readers 256 and 257, a horizontal rotation mechanism 258, a sample container tilting mechanism 259 and a controller 260. The rack transport section 255 can transport the sample rack 9 and is configured to transport the sample container 8 held in the sample rack 9 to an aspiration position for aspirating the sample in the sample container 8 by the sample dispensing section 251 and to move the sample container 8 in which aspiration is completed from the aspiration position.

The rack transport section 255 is provided with a before-analysis placing table for placing the sample rack 9 storing the sample container 8 before analysis, an after-analysis placing table for storing the sample rack 9 storing the sample container 8 after analysis, and a transport path for the sample rack 9 from the before-analysis placing table to the after-analysis placing table through the aspiration position (not shown). In the transport path, the horizontal rotation mechanism 258 and the sample container tilting mechanism 259 are provided and the bar-code reader 256 for reading a rack bar-code of the sample rack 9 on the transport path and the bar-code reader 257 for reading the specimen bar-code of the sample container 8 are provided.

Two cameras and two white LEDs are disposed in front of the sample container tilting mechanism 259. One of the cameras images the sample container 8 which is taken out from the sample rack 9 and held in a vertical state by the sample container tilting mechanism 259, and the other camera images the sample container 8 which is vertically rotated and held in a state in which a bottom portion of the sample container 8 is positioned higher than a cap section 8$a$ by the sample container tilting mechanism 259. These cameras are connected to the information processing unit 270 by a cable for transmitting the electric signals of captured images. Since the configurations and arrangement of the horizontal rotation mechanism 258, the sample container tilting mechanism 259, the cameras and the white LEDs are the same as in the first embodiment, a description thereof will be omitted.

Since the other configurations of the blood sample analyzing apparatus 200 are the same as the configurations of the blood cell analyzing apparatus 5 described in the first embodiment, a description thereof will be omitted.

<Operation of Blood Sample Analyzing Apparatus>

Figure 30C:
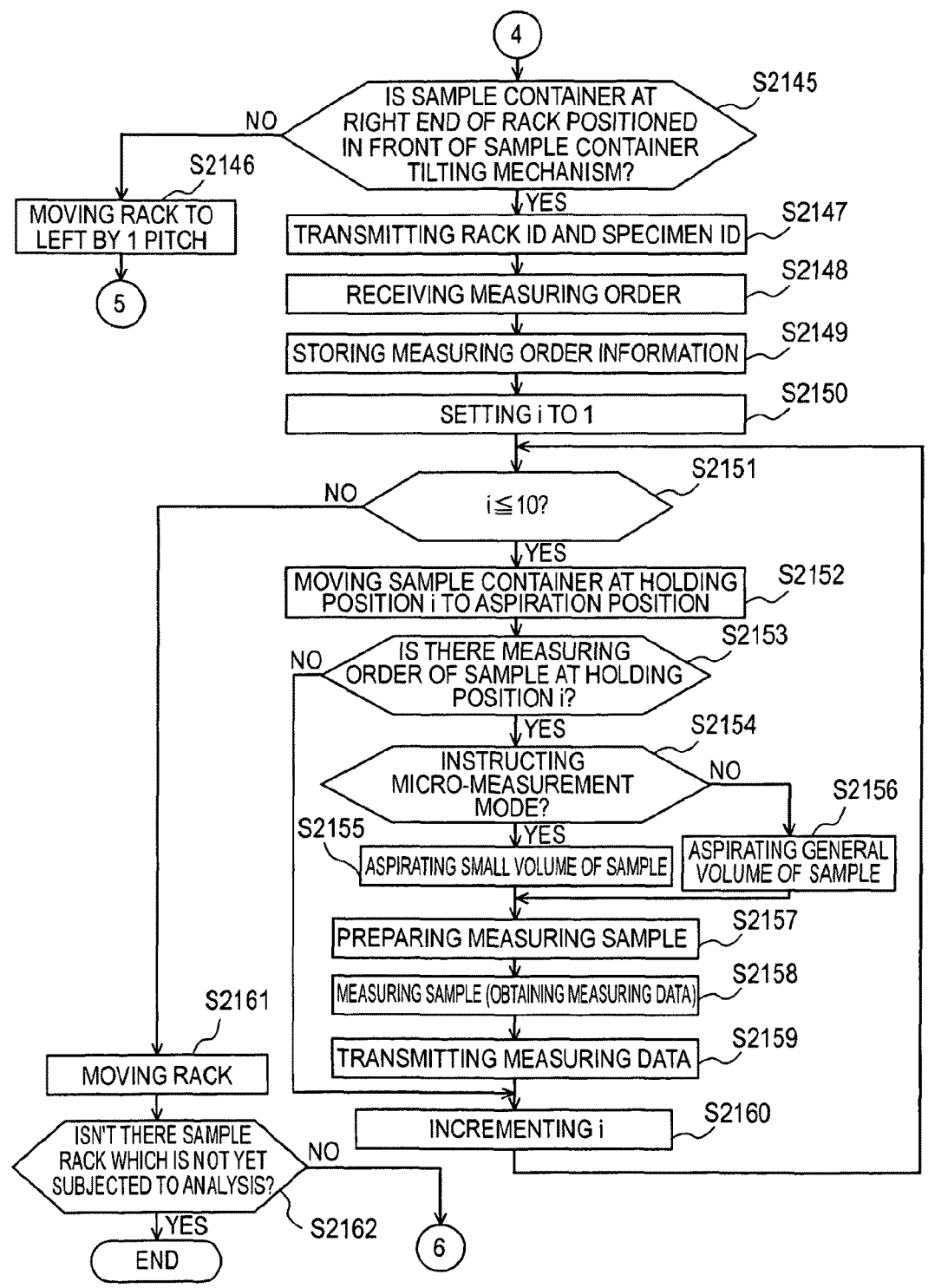
FIG. 30C is a flowchart (second half) showing the flow of the sample measuring operation of the measuring unit according to the second embodiment.

Next, an operation of the blood sample analyzing apparatus according to this embodiment will be described. FIGS. 30A to 30C are flowcharts showing the flow of an operation of the blood sample analyzing apparatus 200 according to this embodiment. FIG. 30A is a flowchart showing the flow of a measurement start instruction operation of the information processing unit 270, and FIGS. 30B and 30C are flowcharts showing the flow of a sample measuring operation of the measuring unit 250 in the sample analysis operation of the blood sample analyzing apparatus 200.

First, when a user starts the blood sample analyzing apparatus 200, an initialization process is executed in the measuring unit 250 and the information processing unit 270, and thus the measuring unit 250 is in a measurement stand-by state and the information processing unit 270 displays a main screen (not shown). A measuring order including a specimen (sample) number, patient information such as the name, age, sex and department of a patient associated with the specimen number and information such as an analysis item is input to the information processing unit 270 in advance by manual input of the user, and the measuring order is stored in a hard disk. In this state, when a start button displayed in the main screen is clicked, that is, when the user performs a start instruction operation, a CPU of the information processing unit 270 receives an instruction to start measurement (Step S2101 of FIG. 30A), and when such an event is generated, a process of Step S2102 is invoked.

In Step S2102, the CPU of the information processing unit 270 generates a measurement start instruction signal and the signal is transmitted to the measuring unit 250 (Step S2102 of FIG. 30A). Then, the CPU completes the process related to the measurement start instruction operation. By issuing the measurement start instruction, the measuring operation of the measuring unit 250 shown in FIG. 30B is started. When the measurement start instruction signal is received by the measuring unit 250 (Step S2131 of FIG. 30B), the controller 260 of the measuring unit 250 controls the rack transport section 255 (Step S2132). The processes of Steps S2132 to S2147 are the same as the processes of Steps S103 to S118 described in the first embodiment, except that the transmission destination of information is the information processing unit 270 in Steps S2141, S2143 and S2147, and thus a description thereof will be omitted.

When receiving a first image taking instruction signal, the information processing unit 270 performs a blood volume detecting process, and when receiving a second image taking instruction signal, the information processing unit performs a blood coagulation determining process. Since the blood volume detecting process and the blood coagulation determining process are the same as in the first embodiment, a description thereof will be omitted. In addition, the information processing unit 270 searches measuring orders corresponding to a rack ID and a specimen ID, determines that a sample in which blood coagulation is detected by the blood coagulation determining process is not measured for each measuring order, and determines whether a sample, in which blood coagulation is not detected, is measured in the normal-measurement mode or in the micro-measurement mode by the measuring order and the blood volume detected by the blood volume detecting process. The processes are the same in Steps S162 to S1613 described in the first embodiment, except that the transmission destination of measuring order information is the measuring unit 250, and thus a description thereof will be omitted.

When an event in which measuring order information is received from the information processing unit 270 occurs (Step S2148), the controller 260 stores the received measuring order information in a memory of the controller 260 (Step S2149). Then, the controller 260 sets a variable i indicating a holding position of the sample rack to 1 (Step S2150) and determines whether i is equal to or less than 10 (Step S2151). When i is equal to or less than 10 (Yes in Step S2151), the controller 260 moves the sample container 8 at the holding position i to an aspiration position where the sample dispensing section 251 aspirates the sample (Step S2152), and determines whether there is a measuring order of the sample at the holding position i from the measuring order information in the memory (Step S2153). When there is no measuring order (No in Step S2153), the controller 260 performs a process of Step S2160.

On the other hand, when there is a measuring order of the sample at the holding position i (Yes in Step S2153), the controller 260 determines whether micro-measurement mode instruction data is included in the measuring order information (Step S2154). When the micro-measurement mode instruction data is included (Yes in Step S2154), the controller causes the sample dispensing section 251 to aspirate a smaller volume of the blood sample than in the normal-measurement mode (Step S2155). When the micro-measurement mode instruction data is not included (No in Step S2154), the controller 260 causes the sample dispensing section 251 to aspirate a general volume of the blood sample (Step S2156).

Next, the controller 260 causes the measuring sample preparing section 252 to mix the aspirated blood sample with a reagent and a diluent and prepare a measuring sample (Step S2157). The controller supplies the prepared measuring sample to the optical detecting section 253 to obtain measuring data including parameters such as peaks and pulse widths of a side-scattered light signal, a forward-scattered light signal and a fluorescent signal (Step S2158). The controller 260 transmits the measuring data to the information processing unit 270 (Step S2159), increments i by 1 (Step S2160) and returns the process to Step S2151. In Step S2151, when i is not equal to or less than 10 (No in Step S2151), the controller 260 moves the sample rack 9 to a storage position on the downstream side of transport (Step S2161). Next, when the sample rack to be analyzed is placed on the before-analysis placing table of the rack transport section 255 (No in Step S2162), the controller 260 returns the process to Step S2132, and when the sample rack to be analyzed is not placed on the before-analysis placing table of the rack transport section 255 (Yes in Step S2162), the controller completes the process.

Third Embodiment

This embodiment is a blood sample analyzing system, which selects an analysis item of an execution object from among analysis items included in a measuring order in accordance with the detected volume of a blood sample, and aspirates a volume of the blood sample necessary to execute the selected analysis item to perform an analysis of the selected analysis item.

[Configuration of Blood Sample Analyzing System]

The configuration of the blood sample analyzing system according to this embodiment is the same as the configuration of the blood sample analyzing system 1 according to the first embodiment, except for a system control apparatus 370 (see FIG. 1 for reference). Accordingly, the same constituent elements are denoted by the same reference numerals and a description thereof will be omitted. The system control apparatus 370 according to this embodiment has the same configuration as the configuration of the system control apparatus 7 according to the first embodiment, except that the CPU 71a is configured to perform the following process by a system control program 374a (see FIG. 12 for reference) stored in the hard disk 71d. Accordingly, the same constituent elements are denoted by the same reference numerals and a description thereof will be omitted.

[Operation of Blood Sample Analyzing System]

The blood sample analyzing system according to this embodiment performs the same operation as the operation of the sample analyzing system 1 described in the first embodiment, except for the operation of the system control apparatus 7. A description of the same operation as the operation of the sample analyzing system 1 according to the first embodiment will be omitted.

<Operation of System Control Apparatus 370>

The system control apparatus 370 according to this embodiment can perform the following measuring order transmitting operation.

FIG. 31A is a flowchart showing the procedure of a measuring order transmitting process of the system control apparatus 370. Since the processes of Steps S361 to S3610 are the same as the processes of Steps S161 to S1610 described in the first embodiment, a description thereof will be omitted. In Step S369, when BV is less than K (No in Step S369), the CPU 71a performs an analysis item selecting process (Step S3611) to be described later.

Figure 31C:
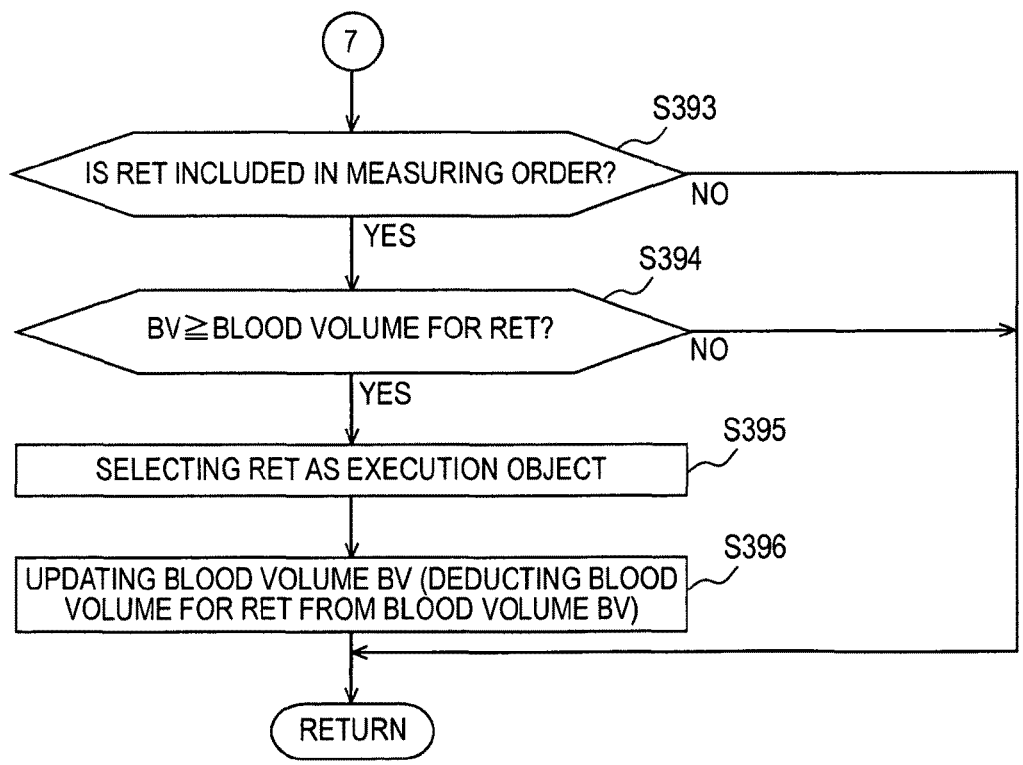
FIG. 31C is a flowchart (second half) showing the procedure of the analysis item selecting process of the system control apparatus according to the third embodiment.

FIGS. 31B and 31C are flowcharts showing the procedure of the analysis item selecting process. The blood cell analyzing apparatus 5 can analyze analysis items including a CBC (complete blood count), DIFF (leukocyte-5-classification), NRBC (nucleated red blood cell) and RET (reticulocyte). These analysis items are prioritized in order of CBC, DIFF, NRBC and RET. In the hard disk 71d of the system control apparatus 370, information about such a priority order and blood sample volumes necessary for the analysis items are stored.

The CPU 71a determines whether the CBC, which is the highest-priority item, is included in the measuring order corresponding to the blood sample at the holding position i (Step S381). When the CBC is not included in the measuring order (No is Step S381), the CPU 71a performs a process of Steps S385. On the other hand, when the CBC is included in the measuring order (Yes in Step S381), the CPU 71a compares the blood volume detected by the blood volume detecting process with the blood volume necessary for the CBC measurement (Step S382). When the detected blood volume is equal to or larger than the blood volume necessary for the CBC measurement (Yes in Step S382), the CBC is selected as an analysis item of the execution object and is stored as the analysis item of the execution object in the RAM 71c (Step S383), and the blood volume obtained by deducting the blood volume necessary for the CBC measurement from the detected blood volume is stored in the RAM 71c (Step S384).

On the other hand, when the detected blood volume is smaller than the blood volume necessary for the CBC measurement (No in Step S382), the CPU 71a performs the process of Step S385.

In Step S385, the CPU 71a determines whether the DIFF, which is the second highest-priority item next to the CBC, is included in the measuring order corresponding to the blood sample at the holding position i (Step S385). When the DIFF is not included in the measuring order (No in Step S385), the CPU 71a performs a process of Step S389. On the other hand, when the DIFF is included in the measuring order (Yes in Step S385), the CPU 71a determines whether the volume of the blood sample (when the blood volume is stored in Step S384, the stored blood volume is used. When the blood volume is not stored in Step S384, the blood volume detected by the blood volume detecting process is used) is equal to or larger than a blood volume necessary for performing the DIFF measurement (Step S386). When the blood volume is equal to or larger than the blood volume necessary for the DIFF measurement (Yes in Step S386), the DIFF is selected as an analysis item of the execution object and is stored as the analysis item of the execution object in the RAM 71c (Step S387). Then, the CPU 71a stores the blood volume obtained by deducting the blood volume necessary for the DIFF measurement from the blood volume at that time point in the RAM 71c, updates the blood volume in the RAM 71c (Step S388), and performs the process of Step S389.

On the other hand, when the blood volume is smaller than the blood volume necessary for the DIFF measurement (No in Step S386), the CPU 71a performs the process of S389.

In Step S389, the CPU 71a determines whether the NRBC, which is the third highest-priority item next to the DIFF, is included in the measuring order corresponding to the blood sample at the holding position i (Step S389). When the NRBC is not included in the measuring order (No in Step S389), the CPU 71a performs a process of Step S393. On the other hand, when the NRBC is included in the measuring order (Yes in Step S389), the CPU 71a determines whether the volume of the blood sample (when the blood volume is updated in Step S384 or S388, the last updated blood volume is used. When the blood volume is not updated, the blood volume detected by the blood volume detecting process is used) is equal to or larger than the blood volume necessary for performing the NRBC measurement (Step S390). When the blood volume is equal to or larger than the blood volume necessary for the NRBC measurement (Yes in Step S390), the NRBC is selected as an analysis item of the execution object and is stored as the analysis item of the execution object in the RAM 71c (Step S391). Then, the CPU 71a stores the blood volume obtained by deducting the blood volume necessary for the NRBC measurement from the blood volume at that time point in the RAM 71c, updates the blood volume in the RAM 71c (Step S392), and performs the process of Step S393.

On the other hand, when the blood volume is smaller than the blood volume necessary for the NRBC measurement (No in Step S390), the CPU 71a performs the process of Step S393.

In Step S393, the CPU 71a determines whether the RET, which is the lowest-priority item, is included in the measuring order corresponding to the blood sample at the holding position i (Step S393). When the RET is not included in the measuring order (No is Step S393), the CPU 71a returns the process to a call address of the analysis item selecting process in the measuring order transmitting process. On the other hand, when the RET is included in the measuring order (Yes in Step S393), the CPU 71a determines whether the volume of the blood sample (when the blood volume is updated in Step S384, S388 or S392, the last updated blood volume is used. When the blood volume is not updated, the blood volume detected by the blood volume detecting process is used) is equal to or larger than the blood volume necessary for performing the RET measurement (Step S394). When the blood volume is equal to or larger than the blood volume necessary for the RET measurement (Yes in Step S394), the RET is selected as an analysis item of the execution object and is stored as the analysis item of the execution object in the RAM 71c (Step S395). Then, the CPU 71a stores the blood volume obtained by deducting the blood volume necessary for the RET measurement from the blood volume at that time point in the RAM 71c, updates the blood volume in the RAM 71c (Step S396), and returns the process to the call address of the analysis item selecting process in the measuring order transmitting process.

On the other hand, when the blood volume is smaller than the blood volume necessary for the RET measurement (No in Step S394), the CPU 71a returns the process to the call address of the analysis item selecting process in the measuring order transmitting process.

After the above-described analysis item selecting process is completed, the CPU 71a stores measuring order information in which the holding position i is associated with the measuring order including only the analysis item selected as the analysis item of the execution object in the analysis item selecting process in the RAM 71c (Step S3612), and performs a process of Step S3613.

Since the processes of Steps S3613 and S3614 are the same as the processes of Steps S1612 and S1613 described in the first embodiment, a description thereof will be omitted.

By performing the above-described measuring order transmitting process, the analysis items which can be executed are selected in descending order of priority when the detected blood volume falls short of the blood volume necessary for executing the analysis items included in the measuring order of the blood sample, and only the selected analysis item is executed by the blood cell analyzing apparatus 5. As a result, the blood sample of a volume necessary for the execution of the selected analysis item is aspirated by the sample dispensing section 511, and thus the generation of an analysis error by the blood cell analyzing apparatus 5 and the stoppage of the blood cell analyzing apparatus 5, which are caused by a sample shortage, can be avoided. Furthermore, since an analysis with respect to the high-priority analysis item is performed, it is possible to obtain an analysis result having high clinical significance.

Fourth Embodiment

This embodiment is a blood sample analyzing system, which determines whether the re-examination of a blood sample for which a re-examination (re-measurement) instruction is made can be performed in accordance with the detected volume of the blood sample, carries out the re-examination when the volume of the blood sample in a sample container is sufficient to carry out the re-examination, and does not carry out the re-examination when the volume of the blood sample in the sample container is insufficient to carry out the re-examination.

[Configuration of Blood Sample Analyzing System]

The configuration of the blood sample analyzing system according to this embodiment is the same as the configuration of the blood sample analyzing system 1 according to the first embodiment, except for a system control apparatus 470 (see FIG. 1 for reference). Accordingly, the same constituent elements are denoted by the same reference numerals and a description thereof will be omitted. The system control apparatus 470 according to this embodiment has the same configuration as the configuration of the system control apparatus 7 according to the first embodiment, except that the CPU 71a is configured to perform the following process by a system control program 474a (see FIG. 12 for reference) stored in the hard disk 71d. Accordingly, the same constituent elements are denoted by the same reference numerals and a description thereof will be omitted.

[Operation of Blood Sample Analyzing System]

The blood sample analyzing system according to this embodiment performs the same operation as the operation of the sample analyzing system 1 described in the first embodiment, except for the operation of the system control apparatus 7. A description of the same operation as the operation of the sample analyzing system 1 according to the first embodiment will be omitted.

<Operation of System Control Apparatus 470>

The system control apparatus 470 according to this embodiment can perform the following re-examination order transmitting operation.

After blood samples in all the sample containers held in one sample rack 9 are analyzed by the blood cell analyzing apparatus 5, the sample rack 9 is stopped on the measuring line 31a. The analysis result data of a blood sample generated by the blood cell analyzing apparatus 5 is transmitted to a host computer from the information processing unit 52 and then the host computer determines whether the redetection of the blood sample is required based on the analysis result data. In this manner, when it is determined that the re-examination is required, a re-examination order including a rack ID of the sample rack 9, a specimen ID of the blood sample and an analysis item as an object of the re-examination is transmitted to the system control apparatus 470 from the host computer. Such a re-examination order is transmitted for each rack ID. That is, among the sample containers 8 held in one sample rack 9, re-examination orders of all the blood samples, for which a determination that the re-examination is required is made, are transmitted.

FIG. 32 is a flowchart showing the procedure of the re-examination order transmitting process of the system control apparatus 470. The system control apparatus 470 receives a re-examination order transmitted from the host computer (Step S401). When an event in which such a re-examination order is received occurs, a process of the following Step S402 is invoked by the CPU 71a.

The CPU 71a sets a variable i indicating a holding position of the sample rack to 1 (Step S402) and determines whether i is equal to or less than 10 (Step S403). When i is equal to or less than 10 (Yes in Step S403), the CPU 71a determines whether a re-examination order corresponding to the holding position i is received (whether there is a re-examination order corresponding to the holding position i) (Step S404). When there is no re-examination order corresponding to the holding position i (No in Step S404), the CPU 71a performs a process of Step S409.

When there is a re-examination order corresponding to the holding position i (Yes in Step S404), the CPU 71a determines the volume of the blood sample necessary for carrying out the re-examination based on the analysis items included in the re-examination order (Step S405). For example, when the re-examination order includes a CBC and a DIFF as analysis items of the re-examination object, the volume of the blood sample necessary for carrying out the re-examination is calculated by adding the volume of the blood sample necessary for the CBC measurement to the volume of the blood sample necessary for the DIFF measurement. Next, the CPU 71a reads a volume of the blood sample remaining in the sample container held at the holding position i (Step S406) and determines whether a remaining volume RV of the blood sample in the sample container is equal to or larger than a volume RK of the blood sample necessary for carrying out the re-examination (Step S407). During the measuring order transmitting operation, when a blood volume BV in the sample container before the measurement and a blood volume K necessary for the measurement satisfy the expression BV□K, the system control apparatus 470 calculates a remaining volume of the blood sample which is obtained by deducting the necessary blood volume K from the blood volume BV, associates the remaining volume with a specimen ID (or a rack ID and a holding position), and stores the remaining volume. The remaining volume is the volume of the blood sample remaining in the sample container after the measurement of the analysis item included in the measuring order is performed by the blood cell analyzing apparatus 5. In Step S406, the remaining volume of the blood sample stored in this manner is read. In Step S407, when RV is less than RK, that is, when the remaining volume of the blood sample falls short of the volume necessary for the re-examination (No in Step S407), the CPU 71a performs a process of Step S409.

On the other hand, when RV is equal to or greater than RK, that is, when the remaining volume of the blood sample is equal to or larger than the volume necessary for the re-examination (Yes in Step S407), the CPU 71a stores re-examination order information in which the holding position i and the re-examination order are associated with each other in the RAM 71c (Step S408) and performs a process of Step S409.

In Step S409, the CPU 71a increments i by 1 and returns the process to Step S403. When i is not equal to or less than 10 in Step S403 (No in Step S403), the CPU 71a transmits the re-examination order information stored in the RAM 71c to the sample transport apparatus 3 (Step S410) and completes the process.

The sample transport apparatus 3 receiving the re-examination order information transports the sample rack 9 stopped in the measuring line 31a when the re-examination order is included in the re-examination order information, and stops the sample container containing the blood sample as an object of the re-examination at an aspiration position. In addition, the sample transport apparatus 3 transmits aspiration instruction data including information of the analysis items included in the re-examination order of the blood sample to the blood cell analyzing apparatus 5, and thus the re-examination of the blood sample is carried out.

With the above-described configuration, the measurement is performed by the blood cell analyzing apparatus 5. As a result, when the remaining volume of the blood sample falls short of the volume necessary for the re-examination, the re-examination is not performed, and when the remaining volume of the blood sample is equal to or larger than the volume necessary for the re-examination, the re-examination is performed. Accordingly, the re-examination of the blood sample can be efficiently carried out.

Fifth Embodiment

This embodiment is a blood sample analyzing system, which determines whether the re-examination of analysis items of a blood sample for which a re-examination (re-measurement) instruction is made can be performed in descending order of priority in accordance with a detected volume of the blood sample, and re-examines a high-priority analysis item capable of being measured when only the volume of the blood sample falling short of the volume necessary for measuring all the analysis items for which a re-examination instruction is made is left.

[Configuration of Blood Sample Analyzing System]

The configuration of the blood sample analyzing system according to this embodiment is the same as the configuration of the blood sample analyzing system according to the fourth embodiment, except for a system control apparatus 570 (see FIG. 1 for reference). Accordingly, the same constituent elements are denoted by the same reference numerals and a description thereof will be omitted. The system control apparatus 570 according to this embodiment has the same configuration as the configuration of the system control apparatus 470 according to the fourth embodiment, except that the CPU 71a is configured to perform the following process by a system control program 574a (see FIG. 12 for reference) stored in the hard disk 71d. Accordingly, the same constituent elements are denoted by the same reference numerals and a description thereof will be omitted.

[Operation of Blood Sample Analyzing System]

The blood sample analyzing system according to this embodiment performs the same operation as the operation of the sample analyzing system described in the fourth embodiment, except for the operation of the system control apparatus 470. A description of the same operation as the operation of the sample analyzing system according to the fourth embodiment will be omitted.

<Operation of System Control Apparatus 570>

The system control apparatus 570 according to this embodiment can perform the following re-examination order transmitting operation.

Figure 33A:
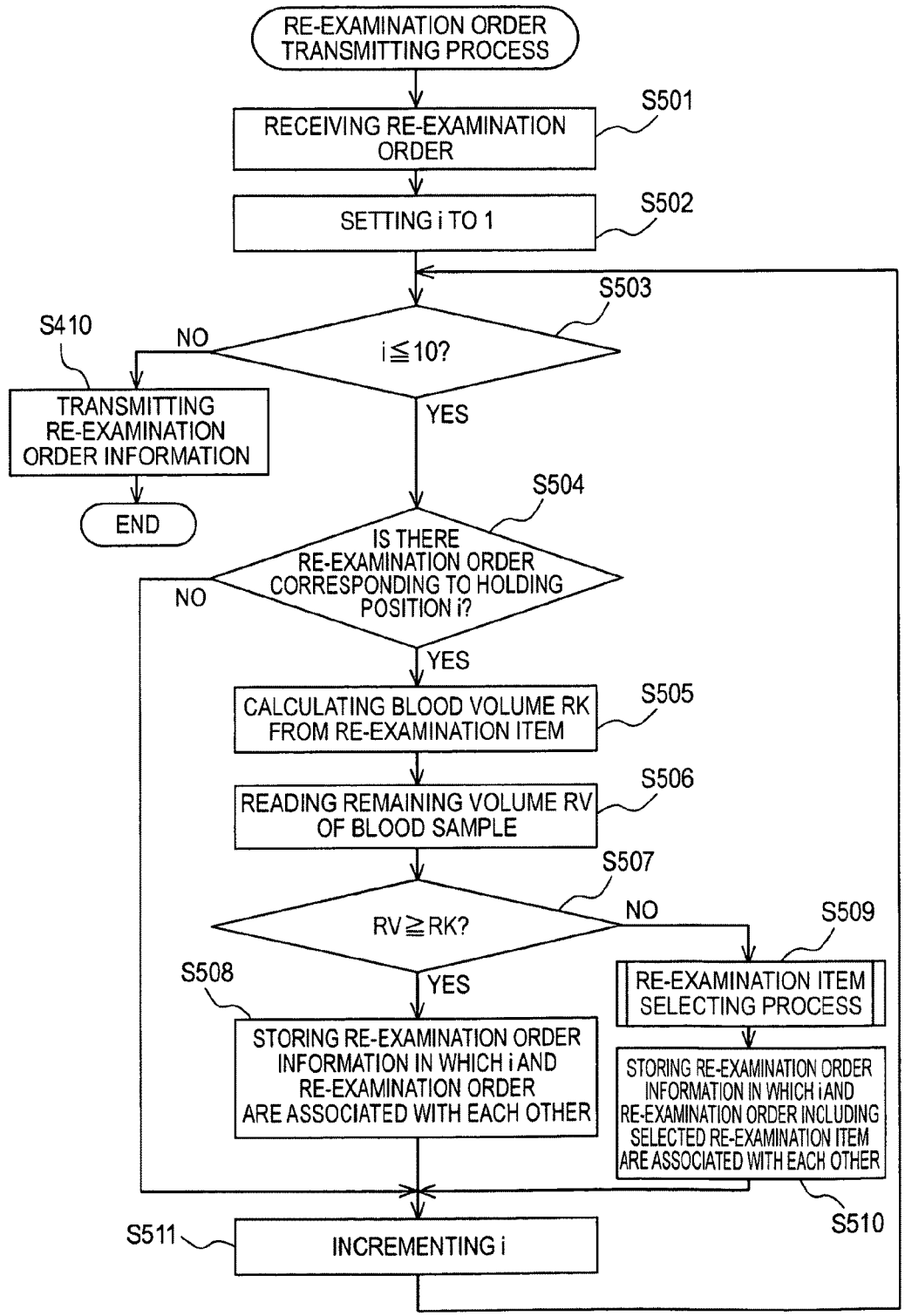
FIG. 33A is a flowchart showing the procedure of a re-examination order transmitting process of a system control apparatus according to a fifth embodiment.

FIG. 33A is a flowchart showing the procedure of a re-examination order transmitting process of the system control apparatus 570. Re-examination items are prioritized in order of CBC, DIFF, NRBC, RET and a smear examination. In the hard disk 71d of the system control apparatus 570, information about such a priority order and blood sample volumes necessary for the re-examination items are stored.

Since the processes of Steps S501 to S507 are the same as the processes of Steps S401 to S407 described in the fourth embodiment, a description thereof will be omitted. In Step S507, when RV is equal to or greater than RK, that is, when a remaining volume of a blood sample is equal to or larger than a volume necessary for the re-examination (Yes in Step S507), the CPU 71a stores re-examination order information in which a holding position i and a re-examination order are associated with each other in the RAM 71c (Step S508), and performs a process of Step S511.

In Step S507, when RV is less than RK, that is, when a remaining volume of a blood sample falls short of a volume necessary for the re-examination (No in Step S507), the CPU 71a performs a re-examination item selecting process (Step S509).

Figure 33C:
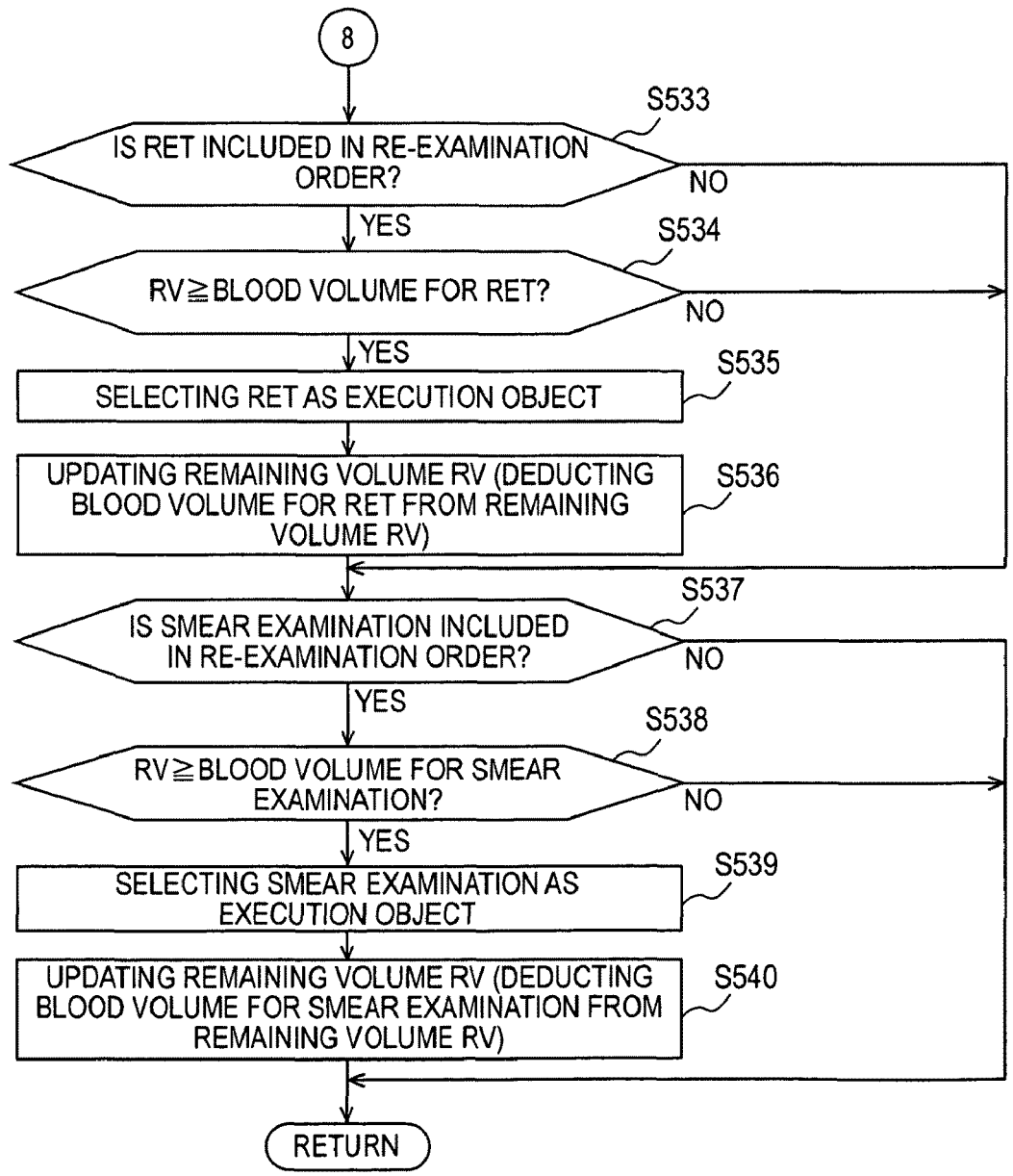
FIG. 33C is a flowchart (second half) showing the procedure of the re-examination item selecting process of the system control apparatus according to the fifth embodiment.

FIGS. 33B and 33C are flowcharts showing the procedure of the re-examination item selecting process. First, the CPU 71a determines whether the CBC, which is the highest-priority item, is included in the re-examination order corresponding to the blood sample at the holding position i (Step S521). When the CBC is not included in the re-examination order (No is Step S521), the CPU 71a performs a process of Steps S525. On the other hand, when the CBC is included in the re-examination order (Yes in Step S521), the CPU 71a determines whether the remaining volume RV of the blood sample in the sample container is equal to or larger than the volume of the blood sample necessary for performing the CBC measurement (Step S522). When the remaining volume RV of the blood sample is equal to or larger than the blood volume necessary for the CBC measurement (Yes in Step S522), the CPU 71a selects the CBC as a re-examination item of the execution object and stores the CBC as the re-examination item of the execution object in the RAM 71c (Step S523), stores, as an updated remaining volume of the blood sample, the blood volume obtained by deducting the blood volume necessary for the CBC measurement from the remaining volume of the blood sample in the RAM 71c (Step S524), and performs the process of Step S525. In addition, in Step S522, when the remaining volume of the blood sample is smaller than the volume of the blood sample necessary for the CBC measurement (No in Step S522), the CPU 71a performs the process of Step S525.

In Step S525, the CPU 71a determines whether the DIFF, which is the second highest-priority item next to the CBC, is included in the re-examination order corresponding to the blood sample at the holding position i (Step S525). When the DIFF is not included in the re-examination order (No in Step S525), the CPU 71a performs a process of Step S529. On the other hand, when the DIFF is included in the re-examination order (Yes in Step S525), the CPU 71a determines whether the remaining volume of the blood sample is equal to or larger than the volume of the blood sample necessary for performing the DIFF measurement (Step S526). When the remaining volume of the blood sample is equal to or larger than the blood volume necessary for the DIFF measurement (Yes in Step S526), the CPU 71a selects the DIFF as a re-examination item of the execution object and stores the DIFF as the re-examination item of the execution object in the RAM 71c (Step S527), stores, as an updated remaining volume of the blood sample, the blood volume obtained by deducting the blood volume necessary for the DIFF measurement from the remaining volume of the blood sample in the RAM 71c (Step S528), and performs the process of Step S529. In addition, in Step S526, when the remaining volume of the blood sample is smaller than the volume of the blood sample necessary for the DIFF measurement (No in Step S526), the CPU 71a performs the process of Step S529.

In Step S529, the CPU 71a determines whether the NRBC, which is the third highest-priority item next to the DIFF, is included in the re-examination order corresponding to the blood sample at the holding position i (Step S529). When the NRBC is not included in the re-examination order (No in Step S529), the CPU 71a performs a process of Step S533. On the other hand, when the NRBC is included in the re-examination order (Yes in Step S529), the CPU 71a determines whether the remaining volume of the blood sample is equal to or larger than the volume of the blood sample necessary for performing the NRBC measurement (Step S530). When the remaining volume of the blood sample is equal to or larger than the blood volume necessary for the NRBC measurement (Yes in Step S530), the CPU 71a selects the NRBC as a re-examination item of the execution object and stores the NRBC as the re-examination item of the execution object in the RAM 71c (Step S531), stores, as an updated remaining volume of the blood sample, the blood volume obtained by deducting the blood volume necessary for the NRBC measurement from the remaining volume of the blood sample in the RAM 71c (Step S532), and performs the process of Step S533. In addition, in Step S530, when the remaining volume of the blood sample is smaller than the volume of the blood sample necessary for the NRBC measurement (No in Step S530), the CPU 71a performs the process of Step S533.

In Step S533, the CPU 71a determines whether the RET, which is the fourth-priority item next to the NRBC, is included in the re-examination order corresponding to the blood sample at the holding position i (Step S533). When the RET is not included in the re-examination order (No is Step S533), the CPU 71a performs a process of Step S537. On the other hand, when the RET is included in the re-examination order (Yes in Step S533), the CPU 71a determines whether the remaining volume of the blood sample is equal to or larger than the volume of the blood sample necessary for performing the RET measurement (Step S534). When the remaining volume of the blood sample is equal to or larger than the blood volume necessary for the RET measurement (Yes in Step S534), the CPU 71a selects the RET as a re-examination item of the execution object and stores the RET as the re-examination item of the execution object in the RAM 71c (Step S535), stores, as an updated remaining volume of the blood sample, the blood volume obtained by deducting the blood volume necessary for the RET measurement from the remaining volume of the blood sample in the RAM 71c (Step S536), and performs the process of Step S537. In addition, in Step S534, when the remaining volume of the blood sample is smaller than the volume of the blood sample necessary for the RET measurement (No in Step S534), the CPU 71a perform the process of Step S537.

In Step S537, the CPU 71a determines whether the smear examination, which is the lowest-priority item, is included in the re-examination order corresponding to the blood sample at the holding position i (Step S537). When the smear examination is not included in the re-examination order (No in Step S537), the CPU 71a returns the process to a call address of the re-examination item selecting process in the re-examination order transmitting process. On the other hand, when the smear examination is included in the re-examination order (Yes in Step S537), the CPU 71a determines whether the remaining volume of the blood sample is equal to or larger than the volume of the blood sample necessary for performing the smear examination (Step S538). When the remaining volume of the blood sample is equal to or larger than the blood volume necessary for the smear examination (Yes in Step S538), the CPU 71a selects the smear examination as a re-examination item of the execution object and stores the smear examination as the re-examination item of the execution object in the RAM 71c (Step S539), stores, as an updated remaining volume of the blood sample, the blood volume obtained by deducting the blood volume necessary for the smear examination from the remaining volume of the blood sample in the RAM 71c (Step S540), and returns the process to the call address of the re-examination item selecting process in the re-examination order transmitting process. In addition, in Step S538, when the remaining volume of the blood sample is smaller than the volume of the blood sample necessary for the smear examination (No in Step S538), the CPU 71a returns the process to the call address of the re-examination item selecting process in the re-examination order transmitting process.

After the above-described re-examination item selecting process is completed, the CPU 71a re-examination order information in which the holding position i is associated with the re-examination order including only the re-examination item selected as the re-examination item of the execution object in the re-examination item selecting process in the RAM 71c (Step S510), and performs a process of Step S511.

Since the processes of Steps S511 and S512 are the same as the processes of Steps S409 and S410 described in the fourth embodiment, a description thereof will be omitted.

The sample transport apparatus 3 installed in front of the blood cell analyzing apparatus 5 receives the re-examination order information. When at least one of the analysis items (CBC, DIFF, NRBC and RET) of the blood cell analyzing apparatus 5 is included as a re-examination item in the re-examination order information, the sample transport apparatus transports the sample rack 9 stopped in the measuring line 31a and stops the sample container containing the blood sample as an object of the re-examination at an aspiration position. In addition, the sample transport apparatus 3 transmits aspiration instruction data including information of the analysis item included in the re-examination order of the blood sample to the blood cell analyzing apparatus 5 to carry out the re-examination of the blood sample.

When the smear examination is included as a re-examination item in the re-examination order information, after the completion of the re-examination of the blood cell analyzing apparatus 5, the sample transport apparatus 3 installed in front of the blood cell analyzing apparatus 5 transports the sample rack to the sample transport apparatus 3 installed in front of the smear preparing apparatus 6. The sample transport apparatus 3 installed in front of the smear preparing apparatus 6 transports the sample rack 9 in the measuring line 31*a* and stops the sample container containing the blood sample as an object of the re-examination at an aspiration position. In addition, the sample transport apparatus 3 transmits aspiration instruction data to the smear preparing apparatus 6 to prepare a smear. The prepared smear is used for a microscopic examination by an automatic smear imaging device or a manual method.

Due to the above-described configuration, even when the remaining amount of the blood sample falls short of the amount necessary for the re-examination, the possibility of carrying out the re-examination is determined in descending order from the highest-priority analysis item. In this manner, a high-priority analysis item which can be measured is re-examined and an analysis item which cannot be measured or a low-priority analysis item is not re-examined. Accordingly, the re-examination of the blood sample can be efficiently carried out.

Other Embodiments

In the above-described first, second, fourth and fifth embodiments, the configuration, in which the detected blood volume is compared with the blood volume necessary for the measurement to perform the measurement in a normal mode when the detected blood volume is equal to or larger than the blood volume necessary for the measurement, and to perform the measurement in a micro-amount mode when the detected blood volume is less than the blood volume necessary for the measurement, has been described. However, the invention is not limited to this. A configuration, in which the aspiration of the sample by the sample dispensing section 511 is performed to measure the sample when the detected blood volume is equal to or larger than the blood volume necessary for the measurement, and the aspiration of the sample by the sample dispensing section 511 is not performed not to measure the sample when the detected blood volume is less than the blood volume necessary for the measurement, also may be employed. In this case, the sample container in which the detected blood volume falls short of the blood volume necessary for the measurement may be stopped at an aspiration position for a shorter time than in the case of performing a blood aspiration operation, or may pass the aspiration position without being stopped. Further, the sample container in which the detected blood volume is equal to or larger than the blood volume necessary for the measurement may be transported in the measuring line 31*a* of the sample transport apparatus 3, and the sample container in which the detected blood volume is smaller than the blood volume necessary for the measurement may be transported in the skip line 31*b* of the sample transport apparatus 3. In a stand-alone sample analyzer, a transport section may be provided with a measuring line and a skip line to switch a transport path as described above.

In addition, without comparing the detected blood volume with the blood volume necessary for the measurement, a blood volume (hereinafter, referred to as "effective blood volume") may be obtained by deducting a predetermined volume from the detected blood volume and be compared with the blood volume necessary for the measurement to exclude an influence such as an error in detection of the blood volume. When the effective blood volume is equal to or larger than the blood volume necessary for the measurement, the measurement may be performed in a normal mode, and when the effective blood volume is smaller than the blood volume necessary for the measurement, the measurement may be performed in a micro-amount mode.

In the above-described first to fifth embodiments, the configuration, in which an image obtained by imaging the sample container in a vertical state is processed and the width of the sample container, a position of the bottom of the sample container and a position (height) of a blood surface are detected to detect a blood volume based on the detection results, has been described. However, the invention is not limited to this. A configuration, in which an image obtained by imaging the sample container 8 in a vertical state is binarized to obtain an area of a blood portion specified by the binarized image and thus a blood volume is obtained from the area by, for example, a look-up table or a calculation formula, also may be employed.

In the above-described first and third to fifth embodiments, the configuration, in which the measuring order information is generated by the system control apparatuses 7, 370, 470 and 570 and the aspiration instruction data is issued by the controller 31*c* of the sample transport apparatus 3 provided separately from the system control apparatuses 7, 370, 470 and 570, has been described. However, the invention is not limited to this. A configuration, in which the generation of the measuring order information and the issuing of the aspiration instruction data are performed by one CPU, also may be employed.

In the above-described first and third to fifth embodiments, the configuration, in which the controller 31*c* of the sample transport apparatus 3 issues the aspiration instruction data and controls the transport operation of the sample rack 9, has been described. However, the invention is not limited to this. A configuration, in which a CPU (for example, the CPU 71*a* of the system control apparatuses 7, 370, 470 and 570 or a CPU of the computer provided separately from this) provided separately from the controller 31*c* issues the aspiration instruction data, also may be employed. In addition, a configuration, in which, the issuing of the aspiration instruction data and the control of the transport operation of the sample rack 9 are performed by, for example, the CPU 71*a* of the system control apparatuses 7, 370, 470 and 570 without providing the controller 31*c* in the sample transport apparatus 3, also may be employed.

In addition, a configuration, in which the sample transport apparatus 3 transmits aspiration instruction data to the blood cell analyzing apparatus 5 or the smear preparing apparatus 6 in the case of the blood sample of which the amount satisfies the amount necessary for the measurement and transmits aspiration prohibition data to the blood cell analyzing apparatus 5 or the smear preparing apparatus 6 in the case of the blood sample of which the amount falls short of the amount necessary for the measurement, and the measuring unit 51 performs the aspiration operation of the blood sample when receiving the aspiration instruction data and does not perform the aspiration operation when receiving the aspiration prohibition data, may be employed.

In the above-described first to fifth embodiments, the configuration, in which an image process is performed using a value related to the B value of the R/B luminance ratio, the R/B accumulation luminance ratio, the B luminance accumulation value and the B value to perform the detection of a blood amount and the determination of blood coagulation, has been described. However, the invention is not limited to this. A G value may be used in place of the B value.

In the above-described first and third to fifth embodiments, the configuration, in which the blood sample analyzing system 1 is provided with the blood cell analyzing apparatus 5 and the smear preparing apparatus 6, has been described. However, the invention is not limited to this. In place of the blood cell analyzing apparatus 5 and the smear preparing apparatus 6, other blood analyzing apparatuses such as a blood coagulation measuring apparatus, an immunity analyzing apparatus and a biochemical analyzing apparatus may be provided. Moreover, the blood sample analyzing system may be configured to include one sample analyzing apparatus or may be configured to include an arbitrary number of the sample analyzing apparatuses among the sample analyzing apparatuses.

In the above-described first to fifth embodiments, the configuration, in which the computer performs the blood volume detecting process and the blood coagulation determining process of the image processing program and thus the computer which is operated as the system control apparatus 7 and the information processing unit 270 detects a blood volume in a sample container and determines whether a blood sample in the sample container is coagulated, has been described. However, the invention is not limited to this. A configuration, in which the blood volume detecting process and the blood coagulation determining process are performed by a dedicated hardware such as FPGA or ASIC which can perform the same process as the image processing program, also may be employed.

In the above-described first embodiment, the configuration, in which the blood volume detecting process and the blood coagulation determining process are performed by the system control apparatus 7 provided independently from the sample check unit 22, has been described. However, the invention is not limited to this. A configuration, in which the blood volume detecting process and the blood coagulation determining process are performed by an image processing section composed of a CPU and the like and incorporated in the sample check unit 22 provided with the cameras 225a and 225b, also may be employed. A configuration, in which the system control apparatus 7 receiving a measuring order and transmitting the measuring order to the sample transport apparatus 3 does not perform the blood volume detecting process and the blood coagulation determining process and a dedicated image processing apparatus performing the blood volume detecting process and the blood coagulation determining process is provided separately from the system control apparatus 7, also may be employed.

In the above-described first embodiment, the configuration, in which all the processes of the system control program 74a are performed by the single computer 7a, has been described. However, the invention is not limited to this. A distribution system for distributing the same process as the above-described system control program 74a to plural apparatuses (computers) and performing the process also may be employed.

In the above-described embodiment, the sample dispensing section 511 inserts the aspiration tube into the sample container 8 transported to a predetermined position on the measuring line 31a in order to aspirate a blood sample from the sample container 8. However, the invention is not limited to this. The measuring unit 51 may bring the sample container 8 transported to a predetermined position into the measuring unit 51 and the dispensing section 511 may insert the aspiration tube into the sample container 8 which has been brought into the measuring unit 51 in order to aspirate a blood sample from the sample container 8.

What is claimed is:

1. A sample analyzer, comprising:
   an imaging device for imaging a sample container which has translucency and contains a sample;
   a measuring device for aspirating the sample contained in the sample container and measuring the aspirated sample;
   a transporting device for transporting the sample container to a supply position for supplying the sample contained in the sample container to the measuring device, wherein the transporting device is capable of transporting the sample container in a transport path which includes the supply position; and
   a controller for performing operations comprising
   obtaining sample volume information relating to volume of the sample in the sample container, based on an image obtained by imaging the sample container by the imaging device,
   obtaining sample volume information relating to necessary volume of the sample for the measurement by the measuring device, and
   performing a first transport control operation for controlling the transporting device so as to transport the sample container via the supply position such that the sample in the sample container is supplied to the measuring device when the volume of the sample in the sample container and the necessary volume of the sample are in a first relationship, and performing a second transport control operation for controlling the transporting device so as to transport the sample container via the supply position such that the sample in the sample container is not supplied to the measuring device when the volume of the sample in the sample container and the necessary volume of the sample are in a second relationship different from the first relationship.

2. The sample analyzer of claim 1, wherein the transporting device transports the sample container which contains a first volume of the sample when the first transport control operation is performed, and the transporting device transports the sample container which contains a second volume of the sample, the second volume being smaller than the first volume, when the second transport control operation is performed.

3. The sample analyzer of claim 1, wherein the transporting device stops the sample container at the supply position for a first time when the first transport control operation is performed, and the transport device stops the sample container at the supply position for a second time shorter than the first time when the second transport control operation is performed.

4. The sample analyzer of claim 1, wherein the transporting device stops the sample container at the supply position when the first transport control operation is performed, and the transport device does not stop the sample container at the supply position when the second transport control operation is performed.

5. The sample analyzer of claim 1, wherein the controller obtains measuring order information including a measuring item of the sample, and obtains the sample volume information relating to the necessary volume of the sample, based on the measuring order information.

6. The sample analyzer of claim 5,
   wherein the measuring order information includes a plurality of measuring items of the sample; and wherein the controller performs operations comprising:

selecting a measuring item which is a measurement execution object by the measuring device from the plurality of measuring items, based on a measuring item included in the measuring order information and the sample volume information relating to the volume of the sample in the sample container; and controlling the measuring device so as to aspirate the sample in the sample container by a volume according to the selected measuring item.

7. The sample analyzer of claim 1, wherein: the controller performs operations comprising:

obtaining remaining volume information relating to remaining volume of the sample contained in the sample container after the measurement of the sample by the measuring device; and determining whether the sample is able to be re-measured based on the remaining volume information.

8. The sample analyzer of claim 1, further comprising a sample processing device for performing a process, different from the measurement by the measuring device, to the sample contained in the sample container, wherein the controller performs operations comprising:

obtaining remaining volume information relating to remaining volume of the sample contained in the sample container after the measurement of sample by the measuring section; and determining whether the process of the sample by the sample processing device is possible based on the remaining volume information.

9. A sample analyzer, comprising an imaging device for imaging a sample container which has translucency and contains a sample;

a measuring device for aspirating the sample contained in the sample container and measuring the aspirated sample;

a transporting device for transporting the sample container to a supply position for supplying the sample contained in the sample container to the measuring device, wherein the transporting device is capable of transporting the sample container in a first transport path for transporting the sample container to the supply position and a second transport path for not transporting the sample container to the supply position; and a controller for performing operations comprising obtaining sample volume information relating to volume of the sample in the sample container, based on an image obtained by imaging the sample container by the imaging device, obtaining sample volume information relating to necessary volume of the sample for the measurement by the measuring device; and performing a first transport control operation for controlling the transporting device so as to transport the sample container in the first transport path when the volume of the sample in the sample container and the necessary volume of the sample are in a first relationship, and performing a second transport control operation for controlling the transporting device so as to transport the sample container in the second transport path when the volume of the sample in the sample container and the necessary volume of the sample are in a second relationship different from the first relationship.

10. The sample analyzer of claim 1, wherein the controller detects a width of the sample container in the image, a position of a bottom portion of the sample container in the image and a position of a liquid surface of the sample in the image, and obtains the sample volume information based on the detection results.

11. The sample analyzer of claim 10, wherein the image includes information relating to color components of blue, green and red for each pixel; and the controller detects the width of the sample container in the image and the position of the bottom portion of the sample container in the image based on information relating to a color component of blue or green in the image, and detects the position of the liquid surface of the sample in the image based on information relating to a color component of red in the image.

12. The sample analyzer of claim 10, wherein a bar-code label is adhered to the sample container; and the controller detects the position of the liquid surface of the sample in the sample container, based on an image of an area excluding the bar-code label in the image.

13. The sample analyzer of claim 10, wherein the sample is a blood sample; and the controller performs operations comprising:

determining whether a blood plasma portion and a blood cell portion of the blood sample in the sample container are separated based on the image; and detecting the position of the liquid surface of the blood sample by performing a first liquid surface position detecting process when it is determined that the blood plasma portion and the blood cell portion of the blood sample are separated, and detecting the position of the liquid surface of the blood sample by performing a second liquid surface position detecting process different from the first liquid surface position detecting process, when it is determined that the blood plasma portion and the blood cell portion of the blood sample are not separated.

14. The sample analyzer of claim 1, wherein the transporting device is configured to transport a rack holding a plurality of sample containers such that the plurality of sample containers are sequentially transported to the supply position one by one.

15. The sample analyzer of claim 14, wherein the transport controller controls the transporting device so as to transport the rack to the supply position after the imaging device has imaged all the sample containers held by the rack.

16. The sample analyzer of claim 1, further comprising an identification information reading device for reading identification information of the sample container, wherein the imaging device images the sample container after the identification information reading device has read the identification information of the sample container.

17. A sample analyzer, comprising:

an imaging device for imaging a sample container which has translucency and contains a sample;

a measuring device for aspirating the sample contained in the sample container and measuring the aspirated sample;

a transporting device for transporting the sample container to a supply position for supplying the sample contained in the sample container to the measuring device; and a controller for performing operations comprising obtaining sample volume information relating to volume of the sample in the sample container, based on an image obtained by imaging the sample container by the imaging device;

obtaining sample volume information relating to necessary volume of the sample for the measurement by the measuring device, and controlling the measuring device so as to perform an aspirating operation for aspirating the sample contained in the sample container when the volume of the sample in the sample container is equal to or larger than the necessary volume of the sample, and controlling the measuring device so as not to perform the aspirating operation when the volume of the sample in the sample container is smaller than the necessary volume of the sample.

18. The sample analyzer of claim 17, wherein
the controller detects a width of the sample container in the image, a position of a bottom portion of the sample container in the image and a position of a liquid surface of the sample in the image, and obtains the sample volume information based on the detection results.

19. A sample analyzer, comprising:
a volume information obtaining device for obtaining sample volume information relating to volume of a sample contained in a sample container;
a measuring device for aspirating the sample contained in the sample container and measuring the aspirated sample;
a transporting device for transporting the sample container to a supply position for supplying the sample contained in the sample container to the measuring device, wherein the transporting device is capable of transporting the sample container in a transport path which includes the supply position; and
a controller for performing operations comprising
obtaining sample volume information relating to necessary volume of the sample for the measurement by the measuring device, and
performing a first transport control operation for controlling the transporting device so as to transport the sample container via the supply position such that the sample in the sample container is supplied to the measuring device when the volume of the sample in the sample container and the necessary volume of the sample are in a first relationship, and performing a second transport control operation for controlling the transporting device so as to transport the sample container via the supply position such that the sample in the sample container is not supplied to the measuring device when the volume of the sample in the sample container and the necessary volume of the sample are in a second relationship different from the first relationship.

20. A sample analyzer, comprising
a volume information obtaining device for obtaining sample volume information relating to volume of a sample contained in a sample container;
a measuring device for aspirating the sample contained in the sample container and measuring the aspirated sample;
a transporting device for transporting the sample container to a supply position for supplying the sample contained in the sample container to the measuring device, wherein the transporting device is capable of transporting the sample container in a first transport path for transporting the sample container to the supply position and a second transport path for not transporting the sample container to the supply position; and
a controller for performing operations comprising
obtaining sample volume information relating to necessary volume of the sample for the measurement by the measuring device; and
performing a first transport control operation for controlling the transporting device so as to transport the sample container in the first transport path when the volume of the sample in the sample container and the necessary volume of the sample are in a first relationship, and performing a second transport control operation for controlling the transporting device so as to transport the sample container in the second transport path when the volume of the sample in the sample container and the necessary volume of the sample are in a second relationship different from the first relationship.

21. A sample analyzer, comprising:
a volume information obtaining device for obtaining sample volume information relating to volume of a sample contained in a sample container;
a measuring device for aspirating the sample contained in the sample container and measuring the aspirated sample;
a transporting device for transporting the sample container to a supply position for supplying the sample contained in the sample container to the measuring device; and
a controller for performing operations comprising
obtaining sample volume information relating to a necessary volume of the sample for the measurement by the measuring device, and
controlling the measuring device so as to perform an aspirating operation for aspirating the sample contained in the sample container when the volume of the sample in the sample container is equal to or larger than the necessary volume of the sample, and controlling the measuring device so as not to perform the aspirating operation when the volume of the sample in the sample container is smaller than the necessary volume of the sample.

* * * * *